US011572542B2

(12) United States Patent
Biondi et al.

(10) Patent No.: US 11,572,542 B2
(45) Date of Patent: Feb. 7, 2023

(54) METHOD FOR THE GENERATION OF GENETICALLY MODIFIED CELLS

(71) Applicant: FONDAZIONE MATILDE TETTAMANTI E MENOTTI DE MARCHI ONLUS, Monza (IT)

(72) Inventors: Andrea Biondi, Monza (IT); Ettore Biagi, Monza (IT); Chiara Francesca Magnani, Monza (IT); Sarah Tettamanti, Monza (IT)

(73) Assignee: FONDAZIONE MATILDE TETTAMANTI E MENOTTI DE MARCHI ONLUS, Monza (IT)

( * ) Notice: Subject to any disclaimer, the term of this patent is extended or adjusted under 35 U.S.C. 154(b) by 580 days.

(21) Appl. No.: 15/524,225

(22) PCT Filed: Nov. 6, 2015

(86) PCT No.: PCT/EP2015/075980
§ 371 (c)(1),
(2) Date: May 3, 2017

(87) PCT Pub. No.: WO2016/071513
PCT Pub. Date: May 12, 2016

(65) Prior Publication Data
US 2017/0355957 A1 Dec. 14, 2017

(30) Foreign Application Priority Data
Nov. 7, 2014 (EP) ..................................... 14192371

(51) Int. Cl.
C12N 5/0783 (2010.01)
A61K 35/17 (2015.01)
A61K 35/12 (2015.01)

(52) U.S. Cl.
CPC ............ *C12N 5/0638* (2013.01); *A61K 35/17* (2013.01); *C12N 5/0636* (2013.01); *A61K 2035/124* (2013.01); *C12N 2502/99* (2013.01)

(58) Field of Classification Search
None
See application file for complete search history.

(56) References Cited

U.S. PATENT DOCUMENTS

| 5,693,622 A | 12/1997 | Wolff et al. |
| 2007/0036773 A1 | 2/2007 | Cooper et al. |
| 2010/0087001 A1* | 4/2010 | Hope ...................... A61P 35/00 435/377 |

FOREIGN PATENT DOCUMENTS

| WO | WO-9946365 A1 | 9/1999 |
| WO | WO-2011103882 A1 | 9/2011 |

OTHER PUBLICATIONS

Cichoki et al. Front. Immunol., Aug. 29, 2019, vol. 10:2078 (Year: 2019).*
Elia et al., Blood 2011, 118 (21)1917 (Year: 2011).*
Jensen et al., Mol. Ther. 2000, 1:49-55 (Year: 2000).*
International Search Report dated Jan. 21, 2016 issued in International Patent Application No. PCT/EP2015/075980.
Manuri et al., "piggyBac Transposon/Transposase System to Generate CD19-Specific T Cells for the Treatment of B-Lineage Malignancies", Human Gene Therapy 21:427-437 (Apr. 2010).
Nakazawa et al., "Optimization of the PiggyBac Transposon System for the Sustained Genetic Modification of Human T-Lymphocytes" J. Immunother. Oct. 2009; 32(8): 826-836.
Singh et al., "Manufacture of Clinical Grade CD19-Specific T Cells Stably Expressing Chimeric Antigen Receptor Using Sleeping Beauty System and Artificial Antigen Presenting Cells", PLOS One, vol. 8, Iss. 5 (May 2013).
Aiuti, A., et al., "Lentiviral hematopoietic stem cell gene therapy in patients with Wiskott-Aldrich syndrome," Science 341(6148):1233151, American Association for the Advancement of Science, United States (Aug. 2013).
Alter, G., et al., "CD107a as a functional marker for the identification of natural killer cell activity," Journal of Immunological Methods 294(1-2): 15-22, Elsevier, Netherlands (2004).
Andolfi, G., et al., "Enforced IL-10 expression confers type 1 regulatory T cell (Trl) phenotype and function to human CD4+ T cells," Molecular Therapy 20(9): 1778-1790, Cell Press, United States (2012).
Bene, M.C., et al., "Proposals for the immunological classification of acute leukemias. European Group for the Immunological Characterization of Leukemias (EGIL)," Leukemia 9(10):1783-1786, Nature Publishing Group, United Kingdom (1995).
Biffi, A., et al., "Lentiviral hematopoietic stem cell gene therapy benefits metachromatic leukodystrophy," Science 341(6148): 1233158, American Association for the Advancement of Science, United States (Aug. 2013).

(Continued)

*Primary Examiner* — James D Schultz
*Assistant Examiner* — J. Douglas Schultz
(74) *Attorney, Agent, or Firm* — Sterne, Kessler, Goldstein & Fox P.L.L.C.

(57) ABSTRACT

The invention provides a method for the improved generation of genetically modified cells in vitro, in order to obtain a population of effector cells with immunotherapeutic activity and methods of using such cells in protocols for adoptive cell therapy. The invention further provides non-viral genetically modified cells, cell populations and cell cultures and the use thereof in the treatment or prevention of diseases and disorders.

18 Claims, 14 Drawing Sheets

Specification includes a Sequence Listing.

(56) References Cited

OTHER PUBLICATIONS

Boch, J., et al., "Breaking the code of DNA binding specificity of TAL-type III effectors," Science 326(5959):1509-1512, American Association for the Advancement of Science, United States (2009).
Brentjens, R.J., et al., "Safety and persistence of adoptively transferred autologous CD 19-targeted T cells in patients with relapsed or chemotherapy refractory B-cell leukemias," Blood 118(18):4817-4828, American Society of Hematology, United States (2011).
Christian, M., et al., "Targeting DNA double-strand breaks with TAL effector nucleases," Genetics 186(2):757-761, Genetics Society of America, United States (2010).
Cong, L., et al., "Multiplex genome engineering using CRISPR/Cas systems," Science 339(6121):819-823, American Association for the Advancement of Science, United States (Feb. 2013).
De Jong, J., et al., "Chromatin landscapes of retroviral and transposon integration profiles," PLoS Genetics 10(4):e1004250, Public Library of Science, United States (Apr. 2014).
Ding, S., et al., "Efficient transposition of the piggyBac (PB) transposon in mammalian cells and mice," Cell 122(3):473-483, Cell Press, United States (2005).
Di Stasi, A., et al., "Inducible apoptosis as a safety switch for adoptive cell therapy," New England journal of Medicine 365(18):1673-1683, Massachusetts Medical Society, United States (2011).
Dotti, G., and Heslop, H.E., "Current status of genetic modification of T cells for cancer treatment," Cytotherapy 7(3):262-272, Elsevier Inc., United States (2005).
Field, A-C., et al., "Comparison of lentiviral and sleeping beauty mediated alphabeta T cell receptor gene transfer," PLoS One 8(6):e68201, Public Library of Science, United States (Jun. 2013).
Fraser, M.J., et al., "Precise excision of TTAA-specific lepidopteran transposons piggyBac (IFP2) and tagalong (TFP3) from the baculovirus genome in cell lines from two species of Lepidoptera," Insect Molecular Biology 5(2):141-51, Wiley-Blackwell Publishing Ltd., United Kingdom (1996).
Gagliani, N., et al., "Coexpression of CD49b and LAG-3 identifies human and mouse T regulatory type 1 cells," Nature Medicine 19(6):739-746, Nature Publishing Group, United Kingdom (Jun. 2013).
Geurts, A.M., et al., "Gene transfer into genomes of human cells by the Sleeping Beauty transposon system," Molecular Therapy 8(1):108-117, Cell Press, United States (2003).
Grupp, S.A., et al., "Chimeric antigen receptor-modified T cells for acute lymphoid leukemia," The New England Journal of Medicine, 368(16):1509-1518, Massachusetts Medical Society, United States (Apr. 2013).
Hackett, P.B., et al., "A transposon and transposase system for human application," Molecular Therapy 18(4):674-683, Cell Press, United States (2010).
Hasan, A.N., et al., "Artificial Antigen Presenting Cells: An Off the Shelf Approach for Generation of Desirable T-Cell Populations for Broad Application of Adoptive Immunotherapy," Advancements in Genetic Engineering 4(3):130, Longdom Publishing, Belgium (Oct. 2015).
Heeg, K., et al., "A rapid colorimetric assay for the determination of IL-2-producing helper T cell frequencies," Journal of Immunological Methods 77(2):237-246, Elsevier, Netherlands (1985).
Hombach, A.A., et al., "Arming cytokine-induced killer cells with chimeric antigen receptors: CD28 outperforms combined CD28-OX40 'super-stimulation,'" Molecular Therapy 21(12):2268-77, Cell Press, United States (Dec. 2013).
Huang, X., et al., "Sleeping Beauty transposon-mediated engineering of human primary T cells for therapy of CD 19+ lymphoid malignancies," Molecular Therapy 16(3):580-589, Cell Press, United States (2008).
Ivics, Z., et al., "Molecular reconstruction of Sleeping Beauty, a Tel-like transposon from fish, and its transposition in human cells," Cell 91(4):501-510, Cell Press, United States (1997).
Kay, M.A., et al., "Viral vectors for gene therapy: the art of turning infectious agents into vehicles of therapeutics," Nature Medicine 7(1):33-40, Nature Publishing Group, United Kingdom (2001).
Kebriaei, P., et al., "Infusing CD19-directed T cells to augment disease control in patients undergoing autologous hematopoietic stem-cell transplantation for advanced B-lymphoid malignancies," Human Gene Therapy 23(5):444-450, Mary Ann Liebert Inc., United States (2012).
Lee, D.W., et al., "T cells expressing CD19 chimeric antigen receptors for acute lymphoblastic leukaemia in children and young adults: a phase 1 dose-escalation trial," Lancet 385(9967):517-528, Elsevier Ltd., United Kingdom (Feb. 2015).
Lu, P.H., and Negrin, R.S., "A novel population of expanded human CD3+CD56+ cells derived from T cells with potent in vivo antitumor activity in mice with severe combined immunodeficiency," J Immunol 153(4):1687-1696, American Association of Immunologists, United States (1994).
Magnani, C.F., et al., "Killing of myeloid APCs via HLA class I, CD2 and CD226 defines a novel mechanism of suppression by human Tr1 cells," European Journal of Immunology 41(6):1652-1662, Wiley-VCH Verlag, United Kingdom (2011).
Magnani, C.F., et al., "Stable Expression Of Chimeric Antigen Receptors (CARs) By Sleeping Beauty-Mediated Gene Transfer and Efficient Expansion Of Leukemia-Specific Cytokine-Induced Killer (CIK) Cells," Blood 122(21): 1663, American Society of Hematology, United States (Nov. 2013a).
Magnani, C.F., et al., "Advanced targeted, cell and gene-therapy approaches for pediatric hematological malignancies: results and future perspectives," Frontiers in Oncology 3(106):1-7, Frontiers Media S.A., Switzerland (Apr. 2013b).
Mali, P., et al., "RNA-Guided Human Genome Engineering via Cas9," Science 339(6121):823-826, American Association for the Advancement of Science, United States (Feb. 2013).
Marin, V., et al., "Characterization of in vitro migratory properties of anti-CD19 chimeric receptor-redirected CIK cells for their potential use in B-ALL immunotherapy," Experimental Hematology 34(9):1218-1228, Elsevier Inc., Netherlands (2006).
Marin, V., et al., "Comparison of different suicide-gene strategies for the safety improvement of genetically manipulated T cells," Human Gene Therapy Methods 23(6):376-386, Mary Ann Liebert Inc., United States (2012).
Maude, S.L., et al., "Chimeric antigen receptor T cells for sustained remissions in leukemia," The New England Journal of Medicine 371(16):1507-1517, Massachusetts Medical Society, United States (Oct. 2014).
Morgan, R.A., et al., "Cancer regression in patients after transfer of genetically engineered lymphocytes," Science 314(5796):126-129, American Association for the Advancement of Science, United States (2006).
Nakazawa, Y., et al., "PiggyBac-mediated Cancer Immunotherapy Using EBV-specific Cytotoxic T-cells Expressing HER2-specific Chimeric Antigen Receptor," Molecular Therapy 19(12):2133-2143, Cell Press, United States (2011).
Naldini, L., "Ex vivo gene transfer and correction for cell-based therapies," Nature Reviews Genetics 12(5):301-315, Nature Publishing Group, United Kingdom (2011).
Neumann, E., et al., "Gene transfer into mouse lyoma cells by electroporation in high electric fields," The EMBO Journal 1(7):841-845, IRL Press Ltd., United Kingdom (1982).
Nicholson, I.C., et al., "Construction and characterisation of a functional CD19 specific single chain Fv fragment for immunotherapy of B lineage leukaemia and lymphoma," Molecular Immunology 34(16-17):1157-1165, Elsevier Science Ltd., United Kingdom (1997).
Oliveira, G., et al., "Use of TK-cells in haploidentical hematopoietic stem cell transplantation," Current Opinion in Hematology 19(6):427-433, Lippincott Williams and Wilkins Ltd., United States (2012).
Passerini, L., et al., "CD4+ T cells from IPEX patients convert into functional and stable regulatory T cells by FOXP3 gene transfer," Science Translational Medicine 5(215):215ra174, American Association for the Advancement of Science, United States (Dec. 2013).
Peng, P.D., et al., "Efficient nonviral Sleeping Beauty transposon-based TCR gene transfer to peripheral blood lymphocytes confers antigen-specific antitumor reactivity," Gene Therapy 16(8):1042-1049, Nature Publishing Group, United Kingdom (2009).

(56) References Cited

OTHER PUBLICATIONS

Pievani, A., et al., "Dual-functional capability of CD3+CD56+ CIK cells, a T-cell subset that acquires NK function and retains TCR-mediated specific cytotoxicity," Blood 118(12):3301-3310, American Society of Hematology, United States (2011).

Pizzitola, I., et al., "Chimeric antigen receptors against CD33/CD123 antigens efficiently target primary acute myeloid leukemia cells in vivo," Leukemia 28:1596-1605, Nature Publishing Group, United Kingdom (Feb. 2014).

Robbins, P.F., et al., "Tumor Regression in Patients With Metastatic Synovial Cell Sarcoma and Melanoma Using Genetically Engineered Lymphocytes Reactive With NY-ESO-1," Journal of Clinical Oncology 29(7):917-924, American Society of Clinical Oncology, United States (2011).

Schmidt, M., et al., "High-resolution insertion-site analysis by linear amplification-mediated PCR (LAM-PCR)," Nature Methods 4(12): 1051-1057, Nature Publishing Group, United Kingdom (2007).

Schmidt-Wolf, I.G.H., et al., "Use of a SCID mouse/human lymphoma model to evaluate cytokine-induced killer cells with potent antitumor cell activity," Journal of Experimental Medicine 174(1):139-149, The Rockefeller University Press, United States (1991).

Silva, G., et al., "Meganucleases and other tools for targeted genome engineering: perspectives and challenges for gene therapy," Current Gene Therapy 11(1):11-27, Bentham Science Publishers B.V., United Arab Emirates (2011).

Singh, H., et al., "Redirecting specificity of T cell populations for CD 19 using the Sleeping Beauty system," Cancer Res 68(8): 2961-2971, American Association for Cancer Research, United States (2008).

Soiffer, R., et al., "Vaccination with irradiated autologous melanoma cells engineered to secrete human granulocyte-macrophage colony-stimulating factor generates potent antitumor immunity in patients with metastatic melanoma," Proc Natl Acad Sci USA 95(22):13141-6, National Academy of Science, United States (1998).

Sun, Q., et al., "Monoclonal antibody 7G3 recognizes the N-terminal domain of the human interleukin-3 (IL-3) receptor alpha-chain and functions as a specific IL-3 receptor antagonist," Blood 87(1):83-92, American Society of Hematology, United States (1996).

Tettamanti, S., et al., "Targeting of acute myeloid leukaemia by cytokine-induced killer cells redirected with a novel CD123-specific chimeric antigen receptor," British Journal of Haematology 161(3):389-401, Wiley-Blackwell Publishing Ltd., United Kingdom (Feb. 2013).

Van De Loosdrecht, A.A., et al., "A tetrazolium-based colorimetric MTT assay to quantitate human monocyte mediated cytotoxicity against leukemic cells from cell lines and patients with acute myeloid leukemia," Journal of Immunological Methods 174(1-2):311-320, Elsevier, Netherlands (1994).

Van Dongen, J.J.M., et al., "Design and standardization of PCR primers and protocols for detection of clonal immunoglobulin and T-cell receptor gene recombinations in suspect lymphoproliferations: Report of the BIOMED-2 Concerted Action BMH4-CT98-3936," Leukemia 17(12):2257-2317, Nature Publishing Group, United Kingdom (2003).

Vigdal, T.J., et al., "Common Physical Properties of DNA Affecting Target Site Selection of Sleeping Beauty and other Tc1/mariner Transposable Elements," J Mol Biol 323(3):441-452, Academic Press Inc., United States (2002).

Wilber, A., et al., "RNA as a source of transposase for Sleeping Beauty-mediated gene insertion and expression in somatic cells and tissues," Molecular Therapy 13(3):625-630, Cell Press, United States (2006).

Wilber, A., et al., "Efficient non-viral integration and stable gene expression in multipotent adult progenitor cells," Stem Cells International 2011(717069):1-14, Hindawi Publishing Corporation, Egypt (2009).

Wilson, M.H., et al., "PiggyBac Transposon-mediated Gene Transfer in Human Cells," Molecular Therapy 15(1):139-145, Cell Press, United States (2007).

Wu, S. C-Y., et al. "piggyBac is a flexible and highly active transposon as compared to Sleeping Beauty, Tol2, and Mos1 in mammalian cell," Proc Natl Acad Sci USA 103(41):15008-15013, National Academy of Science, United States (2006).

Yant, S.R., et al., "High-resolution genome-wide mapping of transposon integration in mammals," Molecular and Cellular Biology 25(6):2085-2094, American Society for Microbiology, United States (2005).

\* cited by examiner

A

B

SEQUENCE LISTING

<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 1
aagccgaaga acaccatcc                                                    19

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 2
agcaccccca caacatga                                                     18

<210> SEQ ID NO 3
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 3
gcttgtggaa ggctactcga aatgtttgac cc                                     32

<210> SEQ ID NO 4
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 4
ccactgggaa tgtgatgaaa gaaataaaag c                                      31

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 5
gacccgggag atctgaattc                                                   20

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 6
agacagggaa tctttactcg ga                                                22

<210> SEQ ID NO 7
<211> LENGTH: 21
<212> TYPE: DNA
<213> ORGANISM: Artificial Sequence

```
<220> FEATURE:
<223> OTHER INFORMATION: Oligonucleotide primer

<400> SEQUENCE: 7
gatctgaatt cagtggcaca g                                              21
```

METHOD FOR THE GENERATION OF GENETICALLY MODIFIED CELLS

CROSS-REFERENCE TO RELATED APPLICATIONS

This application is a National Stage entry of International Application No.: PCT/EP2015/075980, filed Nov. 6, 2015, which claims priority to European Patent Application No. 14192371.4, filed Nov. 7, 2014. The disclosure of the priority applications are hereby incorporated in their entirety by reference.

The present invention refers to a method for the improved generation of genetically modified cells in vitro, in order to obtain a population of effector cells with immunotherapeutic activity and methods of using such cells in protocols for adoptive cell therapy. Cells modified and activated according to the method described in the present invention may find application in the treatment of human diseases such as leukemias, solid tumors, viral infections and autoimmune diseases.

BACKGROUND OF THE INVENTION

The development of immunotherapy protocols based on the adoptive transfer of genetically modified blood cells is currently considered an advanced therapeutic approach for the treatment of severe diseases such as recurrent cancers, viral infections and autoimmune diseases. The main applications exploit methods of genetic modifications through the stable integration into the target cell genome, to replace a compromised functionality or to allow de novo expression of an additional functional protein. Integration of the transgene expression cassettes is recommended in order to stably modify the genome of the target cells and to guarantee its transmission to the progeny. In recent years, several innovative methods have been developed to genetically engineer mononuclear cells (e.g., T cells, PBMCs), antigen presenting cells (APCs) or tumor cells in order to produce cytokines or co-stimulating molecules to potentiate the immune response, leading to a specific and long lasting response. For instance, several clinical trials have demonstrated that allogeneic or autologous irradiated tumor cell vaccines, GM-CSF-modified, were able to stimulate a long lasting immune response for the treatment of solid tumors such as melanoma (1). Specifically, the ectopic expression of proteins with immunotherapeutic activity is used to potentiate effector cells of the immune system with a novel function such as the expression of immunomodulating molecules, cytokines and their receptors (2), engineered receptors that redirect cell recognition specificity towards the target disease, such as artificial T cell receptors (TCRs), tumor-specific chimeric antigen receptors (CARs) (3), and suicide genes that control the activity of genetically modified cells in case of adverse events (4). For example, the modification of CD4$^+$ lymphocytes with IL-10 or FOXP3, has allowed the generation of a stable cell population having phenotype and typical functions of regulatory T cells, T regulatory type 1 cells (Tr1) and FOXP3$^+$ regulatory T (Treg) cells (2, 5, 6). In recent years, the modification of T cells with artificial TCRs (T-TCR) and CARs (T-CAR) has found a strong rationale as a therapeutic approach against several tumor types. T cells engineered with artificial TCRs have been used in various clinical trials for the treatment of melanoma and synovial sarcoma, having MART 1 (7) or NY-ESO-1 as target antigens (8). CARs are artificial receptors made by an extracellular antigen-binding domain, derived from variable light and heavy (VL and VH) regions of a monoclonal antibody, linked together to form a single chain Fragment variable (scFv), a transmembrane domain and an intracellular signal transduction domain, made by the γ chain of Fc fragment of immunoglobulins, or by the ζ chain of the TCR/CD3 complex. Therefore, modification of T cells with CARs has allowed the antigenic recognition properties typical of monoclonal antibodies to be combined with the functional characteristics of T cells, such as migration, cytotoxicity, cytokine release, persistence and consequent amplification of immune response. This has produced various advantages over artificial TCRs: non HLA-restricted recognition of target cells; a large variety of tumor antigens that can be recognized as represented not only by peptides, but also by carbohydrates and glycolipids; and, finally, technically less complex production of the CAR, since it does not require the isolation of tumor-specific Cytotoxic T Lymphocyte (CTL) clones to identify high affinity TCRs. Compared with the use of monoclonal antibodies, genetic manipulation of T cells with TCRs or CARs confers improved biodistribution and immunological memory, thus granting a long lasting response. Moreover, with second and third generation CARs, it is possible to include one or two co-stimulatory molecules in the intracellular domains improving the survival and persistence of the cells in a hostile environment such as the tumor microenvironment. The promising preclinical results obtained with TCR and CAR modified T cells have prompted the development of clinical protocols that have shown to be effective in the control of solid and hematologic tumors. In the context of anti-cancer immunotherapy, the use of TCR and CAR-modified T cells demonstrates the improved efficacy in recent clinical trials for high risk, recurrent leukemias and lymphomas following treatment with chemotherapeutic agents and hematopoietic stem cell transplant (9-12). With the purpose to optimize the safety profile of adoptive cell therapy strategies, suicide genes allow the selective elimination of the modified cells upon prodrug administration, by encoding for enzymes leading to functional active toxic products that favor the activation of apoptosis or inhibit cell proliferation. The herpes simplex virus thymidine kinase (HSV-TK) has been shown to be effective in patients by rendering T cells susceptible to gancyclovir (13). Currently, several suicide gene systems are available and, in particular, the recently developed inducible Caspase 9 system (iC9), triggering apoptosis processes by conditional dimerization, displays an efficacy similar to the historical suicide system HSV-TK, with the advantage of a faster action and less immunogenicity (14). Currently, the feasibility and efficacy of gene transfer methods, coupled with the required manufacturing under GMP conditions and the safety concerns, represent critical aspects for the successful clinical application of cell-based immunotherapy approaches. Historically, the clinical application of gene transfer exploits the use of clinical-grade retroviral vectors, γ-retro, lenti, foamy and α-retro viruses, characterized by a high efficiency and stable gene transfer in primary cells (15, 16). However, non-viral methods of stable gene transfer have recently been developed, as alternatives to viral vectors, with the purpose to overcome cost, manufacturing and safety issues including insertional genotoxicity, which limit the clinical application of cells transduced with viral vectors to only few specialized centers and to a limited number of patients. The ex vivo use of plasmid DNA vectors associated with stable integration into the human genome, by transposons, Zn-finger nucleases (17) and integrases such as PhiC3 phage integrase (18), offers a valid alternative to viral methods, being easy to purify, less immunogenic and, in some cases, safer in terms of integration patterns (19). The coupled use of nucleic acids and the electroporation technique (20) or nucleofection technique, which facilitates the entry of macromolecules in the cell by means of exposure to an electromagnetic field, has been used to transfer genetic material in mammalian cells with high efficiency. For instance, transfecting cells with the Sleeping Beauty (SB) transposon and transposase system is less expensive, being plasmid DNA easier to produce and easier to purify compared to viral vector systems, and the expression cassette is integrated by a non-homologous recombinant mechanism with a safer close-to-random distribution compared to γ-retro viral vectors that display a marked tendency to target gene promoters and an increased probability to deregulate the expression of the targeted genes (21). Other transposon systems have been evaluated as alternatives to SB, such as the PiggyBac (PB) transposon, which has a large cargo capacity and a higher transposition activity (22-24). However, in order to obtain highly efficient electroporation and/or nucleofection, strong magnetic fields are used together with high quantities of DNA. This procedure reduces cell survival and limits the possibility of obtaining sufficient numbers of efficiently modified cells, which represents a main requirement for conducting multicenter clinical trials and the subsequent commercial scale manufacturing of TCR or CAR cells for use in adoptive cell therapy. Significant efforts have been undertaken by various groups to render the SB system useful for the development of TCR and CAR-expressing T cells for clinical use (25-27).

Specifically, for the development of CAR therapies derived from Cytokine Induced Killer (CIK) cell cultures (28-30), the CIK cell cultures comprise heterogeneous populations of effector lymphocytes with acquired NK-like cytotoxicity generated by culturing peripheral blood mononuclear cells (PBMCs) in the presence of IFN-γ, IL-2 and monoclonal antibodies (mAbs) against CD3 enriched in highly efficient cytotoxic $CD3^+CD56^+$ cells, herein CIK cells. However, none of the currently published methods for T cell or NK cell stimulation and expansion following non-viral vector based nucleofection apply to CIK cells, as those methods were not designed to facilitate cell differentiation into the CIK cells (27, 31-33). The administration of irradiated PBMCs to a cell population undergoing cell expansion after nucleofection was previously described (25, 31, 33). The administration of irradiated PBMCs was reported to have taken place at varying time points in the respective studies, after nucleofected cells already had undergone stimulation/activation, substantial differentiation and/or expansion over the course of several days or several weeks. However, the methods of stimulation and expansion of CIK cells/CIK cell populations and T cells/T cell populations upon nucleofection with plasmidic DNA vectors to generate T-TCR, T-CAR, CIK cells modified with TCRs (CIK-TCR) or CIK cells modified with CARs (CIK-CAR) or cell populations modified with TCRs (CIK-TCR cell populations) or CARs (CIK-CAR cell populations), such as CIK cell cultures, reported to date are not optimal for efficient cell stimulation and expansion, sufficient to support large scale utility TCR, CAR therapies in multi-center clinical trials or in the commercial market place.

In particular, the inventors have found that addition of irradiated PBMCs after nucleofection by the Sleeping Beauty system encoding two distinct CD19- and CD123-specific CARs in differentiated CIK cell cultures leads to an average transfection at 24 hours of 16.7% and a mean survival percentage of 15% and 18.8% for CD19.CAR and CD123.CAR, respectively (n=4). The $CD3^+/CD56^+$ phenotype of CIK cells was affected, with a percentage at the end of differentiation of only 20.5% and 21.3% for CD19.CAR and CD123.CAR respectively, and the cell expansion was 9.3 and 8.2 respectively, measured as fold increase within 3 weeks. CIK cell cultures expressed the CAR molecules with a frequency of 6.0% and 4.5% for CD19.CAR and CD123.CAR respectively, and the viability of the final cell product was 4.9% and 3.9% respectively (data not published). Although these results provide pre-clinical evidence that transfection and expansion of CIK cells expressing CAR molecules is possible, they also show that transfection and expansion of CIK cells expressing CAR molecules is not sufficient to support large scale, clinically useful platforms for CAR therapy.

Accordingly, there is therefore a strong interest in developing methods of non-viral modification of mononuclear cells coupled with more efficient cell stimulation and expansion platforms for the development of T-TCR, T-CAR, CIK-TCR and CIK-CAR cells and cell populations for immunotherapeutic applications, which would require limited manipulation and/or stimulation and allow for the simple scale-up and automation of related manufacturing processes.

The present invention offers a solution to this problem, making available highly efficient and commercially viable methods to obtain the stable expression of nucleic acids in cells by non-viral gene transfer coupled with the efficient stimulation and expansion of the transfected cells.

All references to patents, patent applications and publications are incorporated herein by reference in their entirety.

DESCRIPTION OF THE INVENTION

The present invention relates to improved methods of generating cells, cell cultures and/or cell populations by: a) non-viral transfer of nucleic acids into mononuclear cells; a) addition of antigen presenting cells ("APCs"), such as irradiated or Mitomycin-C treated mononuclear cells, within a specified window of time before, during or after the transfer of nucleic acids; c) addition of one or more antigen stimulating agents, such as T cell receptor (TCR) stimulating agents, within a specified window of time before, during or after the transfer of nucleic acids or the addition of the antigen presenting cells; d) optional addition of differentiating agents; and/or e) optional addition of stimulating and expanding agents. As such, the methods of the present invention provide for the highly efficient modification, differentiation, stimulation and/or expansion of mononuclear cells in cell cultures. The collective steps of: a) modification of mononuclear cells through nucleofection and/or electroporation; b) addition of antigen presenting cells, such as irradiated or Mitomycin-C treated mononuclear cells; c) addition of antigen stimulating agents, such as TCR stimulating agents; d) optional addition of differentiating agents; and e) optional addition of stimulating and expanding agents each taking place within the limited time windows, translate into an efficient modification, differentiation, stimulation and/or expansion of modified cells and/or cell populations and the stable expression of transgenes in a manner that allows for scale-able manufacturing of genetically modified cells and/or cell populations supportive of multi-center clinical trials and commercialization. This method represents a simplified and efficient process for the generation of genetically modified cells, without the need for certain manufacturing steps, such as the selection of cells with drugs, purification by cell sorting or repeated stimulation, for example, through beads or artificial antigen presenting cells (aAPCs) (e.g., the method of the present invention preferably incorporates only one stimulation step, for example, addition of antigen presenting cells and/or stimulating agents once during the culture period). Specifically, the invention provides methods to genetically modify, differentiate, stimulate, and/or expand in vitro, mononuclear cells, preferably mammalian and more preferably human peripheral blood mononuclear cells (PBMCs) for human use, to generate cells and/or cell populations comprising artificial T cell receptor T cells (T-TCR) or chimeric antigen receptor T cells (T-CAR), which comprises the following steps, which collectively would take place within a 10 day time window, preferably 24 hours, irrespective of the sequence by which these steps are initiated:

a) non-viral transfer of one or more nucleic acids, preferably encoding T cell receptors and/or chimeric antigen receptors or combinations thereof into a population of mononuclear cells in a cell culture;

b) addition of antigen presenting cells, preferably irradiated and/or Mitomycin-C treated mononuclear cells, or combinations thereof, to the cell culture before, during or within about 10 days after the transfer of nucleic acids; and c) addition of one or more antigen stimulating agents to the culture, preferably TCR stimulating agents such as OKT3 or other agents or proteins known to support the stimulation of T cells (e.g., $CD3^+$ cells), before, during or after the transfer of nucleic acids or the addition of antigen presenting cells.

Preferably, with regards to the generation of genetically modified CIK cells and/or cell populations comprising such cells (e.g., the heterogeneous population of effector lymphocytes generated by culturing PBMCs in the presence of IFN-γ, IL-2 and monoclonal mAbs against CD3 and enriched in highly efficient cytotoxic $CD3^+CD56^+$ cells, herein CIK cells), the invention provides a method to genetically modify, differentiate, stimulate and/or expand in vitro mononuclear cells, preferably mammalian and more preferably human peripheral blood mononuclear cells for human use, to generate CIK-TCR cells and CIK-CAR cells and/or cell populations comprising such cells, which comprises the following steps, which collectively would take place within a 10 days time window, preferably 24 hours, irrespective of the sequence by which these steps are initiated:

a. non-viral transfer of one or more nucleic acids, preferably encoding T cell receptors or chimeric antigen receptors, into a population of mononuclear cells in a cell culture;

b. addition of one or more differentiating agents, preferably interferon gamma (IFN-gamma), to the cell culture before, during or after the transfer of nucleic acids, wherein the differentiating agent differentiates the mononuclear cells in the cell culture into cytokine induced killer cells (CIKs) and/or cell populations comprising such cells;

c. addition of antigen presenting cells, preferably irradiated and/or Mitomycin-C treated mononuclear cells, or combinations thereof, to the cell culture before, during or within about 10 days after the transfer of nucleic acids or addition of differentiating agents; and d. addition of one or more antigen stimulating agents to the cell culture, preferably TCR stimulating agents such as OKT3 or similar agent known to support the stimulation of CIK cells and/or cell populations comprising such cells, before, during or after the transfer of nucleic acids, the addition of differentiating agents or the addition of antigen presenting cells.

Preferably, CIK cell populations comprise the $CD3^+CD56^+$ CIK cells, the $CD3^+CD56^-$ cells, the $CD3^-CD56^+$ cells or combinations thereof.

The transfer of nucleic acids (e.g., genetic transfer) occurs preferably by electroporation, causing a temporary formation of pores in the cell membranes through electric pulses, or more preferably by nucleofection, a specific electroporation method that facilitates the entry of nucleic acids not only in the cytoplasm but also in the nucleus. In a preferred embodiment, electroporation and/or nucleofection of mononuclear cells is performed in the presence of nucleic acids, such as purified or "naked" DNA by means of Amaxa™ 4D Nucleofector™ System, Neon® Transfection System or comparable systems known in the art. Other non-viral methods of genetic transfer of nucleic acids such as purified DNA or naked DNA (e.g., as described in U.S. Pat. No. 5,693,622) can be used. Nucleic acids, preferably exogenous, can contain sequences encoding T cell receptors (TCRs) or chimeric antigenic receptors (CARs). Specifically, exogenous nucleic acid can contain sequences encoding an expression cassette able to stably integrate into the target cell genome by a mechanism of integration based on non-viral vectors, such as transposons, Zn-finger nucleases, integrases, transcription activator-like effectors (TALEs) (34, 35), clustered regularly interspaced short palindromic repeats (CRISPR/Cas) systems (36, 37) or any other method known in the art. In a preferred embodiment, the expression cassette is part of a two-component system, the plasmid or, alternatively, RNA encoding a transposase enzyme, and one or more plasmids containing the transposon consensus sequence, such as Sleeping Beauty ("SB") (38) and PiggyBac (39, 40), to obtain efficient non-viral gene transfer. For instance, the expression cassette can include the SB integrase, the transposase SB11, cloned, modified and under the control of a cytomegalovirus (CMV) promoter and can be enclosed in the sequence SB inverted repeats/directed repeats (IR/DR) (41).

Mammalian, preferably human, for human use, mononuclear cells, or the T cells derived from these precursors, used in the method described in the present invention can be isolated and/or purified by known methods from any known source, including for example, bone marrow, blood, peripheral blood mononuclear cells, cord blood, blood derived products obtained from leukapheresis, lymphoid tissues, lymph nodes, thymus, spleen or other organs such as pancreas, eye, heart, liver, gut, skin or muscle. Mammalian, preferably human, mononuclear cells can be selected and isolated by any known method, including for example, by using labeled antibodies or ligands and applying FACS sorting, magnetic technologies, beads, gradient based centrifugation or the rosette method.

The sources of mononuclear cells and methods for the isolation of specific populations of mononuclear cells or T cells (for instance $CD3^+CD56^-$, $CD4^-CD8^+$, $CD4^+CD8^-$, $CD4^-CD8^-$, $CD4^+CD8^-$, $CD3^+CD56^+$, $CD3^-CD56^-$) that can be used according to the present invention are well known and described in the literature.

The mononuclear cells and/or cell populations can include peripheral blood mononuclear cells, bone marrow derived mononuclear cells, umbilical cord blood derived mononuclear cells, lymphocytes, monocytes, dendritic cells, macrophages, T lymphocytes, naïve T cells (Tn), memory T cells like central memory T cells (Tcm), effector memory T cells (Tem), memory stem cells (Tscm), natural killer cells (NK), hematopoietic stem cells, embryonic pluripotent stem cells (ES) and induced pluripotent stem cells (IPS) and combinations thereof. Mononuclear cells can be a mixed population or a population derived from a single clone.

Mononuclear cells as a source of antigen presenting cells (which may also be referred to as "accessory cells" or "feeder cells") are known in the art and can be irradiated by any known method, for example using a source of cesium137 (60Gy) or other known ionizing radiation sources, or alternatively treated with Mitomycin-C to be rendered mitotically incompetent in order to prevent overgrowth of target cells by the antigen presenting cells. Generally, cells are treated with Mitomycin-C for a period varying from about thirty (30) minutes to about two (2) hours at a concentration of about 10-40 µg/ml, followed by washes. Gamma irradiation is preferable to Mitomycin-C treatment of such cells to eliminate the toxic effect of the residual drug to the target cells. Gamma irradiation, or treatment with Mitomycin-C, is preferably performed before the addition of these cells to the cell culture of mononuclear cells of the above-mentioned methods of the present invention. The use of irradiated mononuclear cells, and particularly irradiated PBMCs is preferred.

The population of antigen presenting cells, for example, irradiated or Mitomycin-C treated mononuclear cells, can also contain cells such as monocytes, dendritic cells and/or artificial antigen presenting cells ("aAPCs"), which may optionally be irradiated or treated with Mitomycin-C. Moreover, antigen presenting cells, and particularly irradiated or Mitomycin-C treated mononuclear cells, can be obtained from a source genetically non-identical, partially identical or familiar in respect to the source providing the mononuclear cells for transfer of nucleic acids (e.g., the patient) or, preferably, from a genetically identical source or the same source.

The addition of irradiated or Mitomycin-C treated mononuclear treated cells is performed before, during or within about ten (10) days after the transfer of nucleic acids, preferably after and more preferably within 2 hours after the transfer of nucleic acids. Although the present invention is not intended to be bound or limited by theory, it is believed that the addition of antigen presenting cells to the cell culture, preferably irradiated or Mitomycin-C treated mononuclear cells, re-establishes accessory populations that have been lost during the process of transferring nucleic acids, for example by nucleofection/electroporation, and thus allows for the stimulation of mononuclear cells (e.g., PBMCs) via a receptor, such as the TCR, with stimulating agents such as OKT3.

The stimulating agents, such as one that stimulates the TCR, are also known in the art and may also induce the differentiation and activation of genetically modified T cells such as $CD3^+CD4^-CD8^+$, $CD3^+CD4^+CD8^-$, but also $CD8^+$, $CD4^+$, $CD4^-CD8^-$, $CD3^+CD56^+$, $CD3^+CD56^-$ or NK $CD3^-CD56^+$, T lymphocytes, naïve T cells (Tn), memory T cells such as central memory T cells (Tcm), effector memory T cells (Tem) and memory stem cells (Tscm). The population of genetically modified, differentiated and/or activated cells can also include T cells polarized toward alpha/beta Th1, Th2, Th17, Thf, Treg, Tr1, CD8 CTL, NKT and/or gamma/delta and stably express the gene of interest. Preferably such stimulating agents are selected from TCR stimulating agents, for example antibodies, such as anti-CD3 (e.g., OKT3), anti-CD28 or other anti-TCR receptor antibodies.

The stimulating agent, preferably a TCR stimulating agent, can be added to the cell culture before, during or after the addition of the antigen presenting cells, such as irradiated or Mitomycin-C treated mononuclear cells, and is preferably added after the addition of irradiated or Mitomycin-C treated mononuclear cells or their derivatives. If added before, the stimulating agent preferably remains present in the cell culture at the time of addition of the antigen presenting cells and preferably remains present during the stimulation of the mononuclear cells.

The methods of the present invention also allow for the generation of a sufficient number of modified cells and/or cell populations, preferably cells and/or cell populations comprising effector cells, able to mount an effector immune response, preferably cells and/or cell populations comprising T cells expressing CAR molecules (T-CAR) and/or CIK cells expressing CAR molecules (CIK-CAR), for in vivo infusion, which would allow for a simple and efficient scale-up, with the possibility for automation of related manufacturing processes. The methods can be used either for the generation of modified cells and/or modified cell populations of such cells to be used for research purposes, or for clinical use by administration to mammalian subjects with diseases or disorders that can benefit from immunotherapy, preferably humans, having cancers, such as leukemia, in particular acute lymphoblastic leukemia expressing endogenous CD19, and acute myeloid leukemia expressing endogenous CD123, as well as lymphomas, solid tumors, viral infections and autoimmune diseases.

According to this protocol, IFN-γ was added on D0 and γ-irradiated PBMCs from the same source of the nucleofected PBMCs were also added on D0 to reconstitute the myeloid fraction of PBMCs that was lost after the modification procedure.

On Day 1 (D1) the expansion protocol was started with OKT3 and IL-2 and cells were cultivated in the presence of IL-2 until Day 21.

Figure 2:
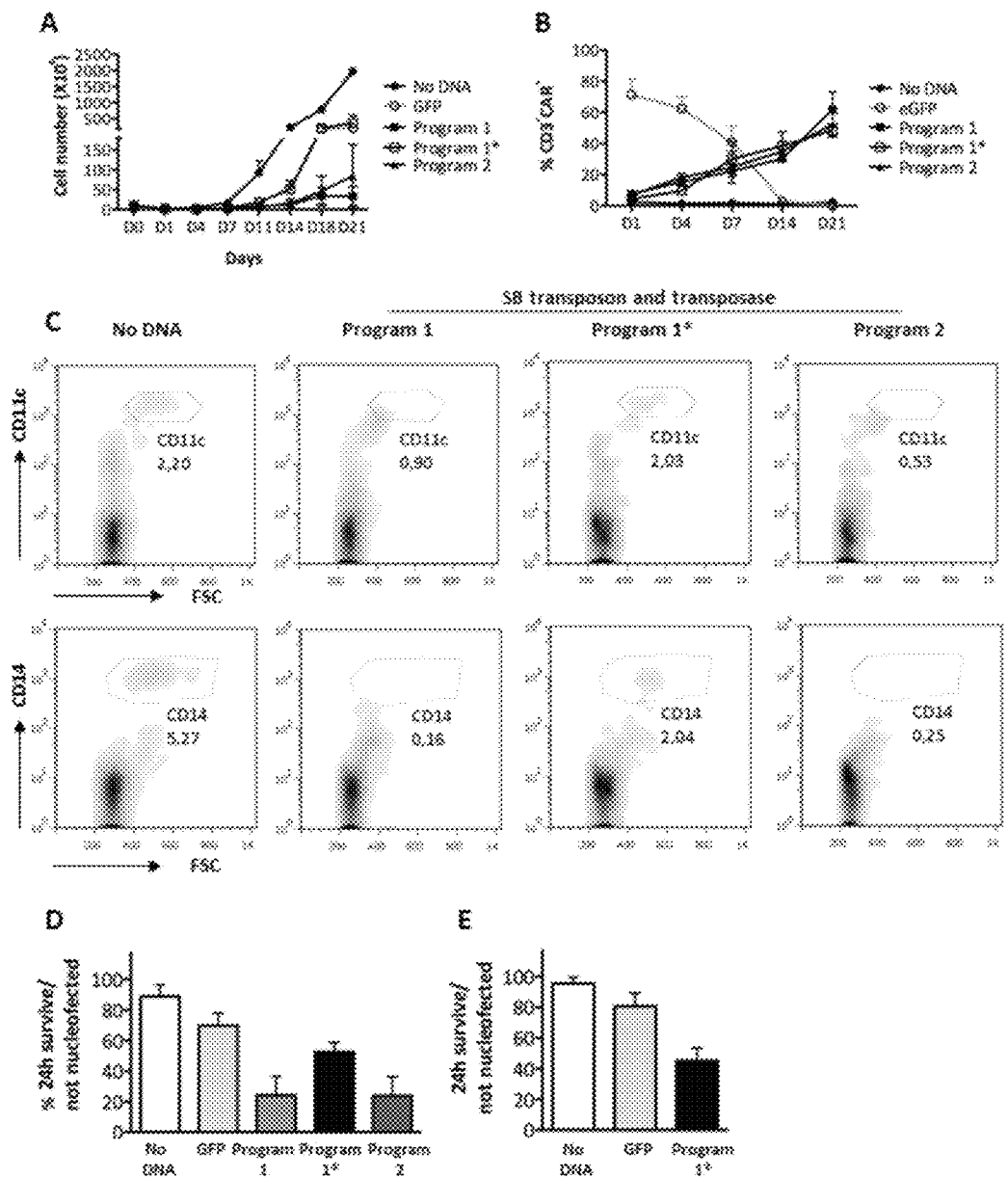

FIG. 2 includes FIGS. 2A, B, C, D and E and describes the optimization of the clinical-grade protocol of modification of mononuclear cells by nucleofection with the Sleeping Beauty transposon system and the expansion procedure of the CIK cell populations. (A) Cell count was performed over time to determine the proliferation following nucleofection according to program 1 of nucleofection in the absence of DNA, or with GFP plasmid, or with nucleic acids encoding for the transposon CD123.CAR in the presence or absence of the simultaneous addition of γ-irradiated PBMCs (Program 1*) or, alternatively, with Program 2. Mean±standard error (SE) of 3 donors are reported. (B) Modification was determined over time by flow-cytometric analysis of CD3 and CAR expression. (C) The presence of CD11c+ dendritic cells and CD14+ monocytes was determined by cytofluorimetric analysis at D1 of the protocol. Data from one donor representative of 2 donors tested are shown. Numbers represent the percentage of positive cells. (D, E) The percentage of survival at 24 h of CD3+ cells after nucleofection was determined by cell count and normalized to cells that were not nucleofected. Mean±SE of 3 donors are reported according to program 1 and 2 of 10 donors for GFP, and of 13 donors from No DNA and Program 1* conducted using the construct CD123.CAR (D). Mean±SE of 6 donors for No DNA, of 5 donors for GFP and of 7 donors for Program 1* conducted using the construct CD19.CAR (E).

Figure 3:
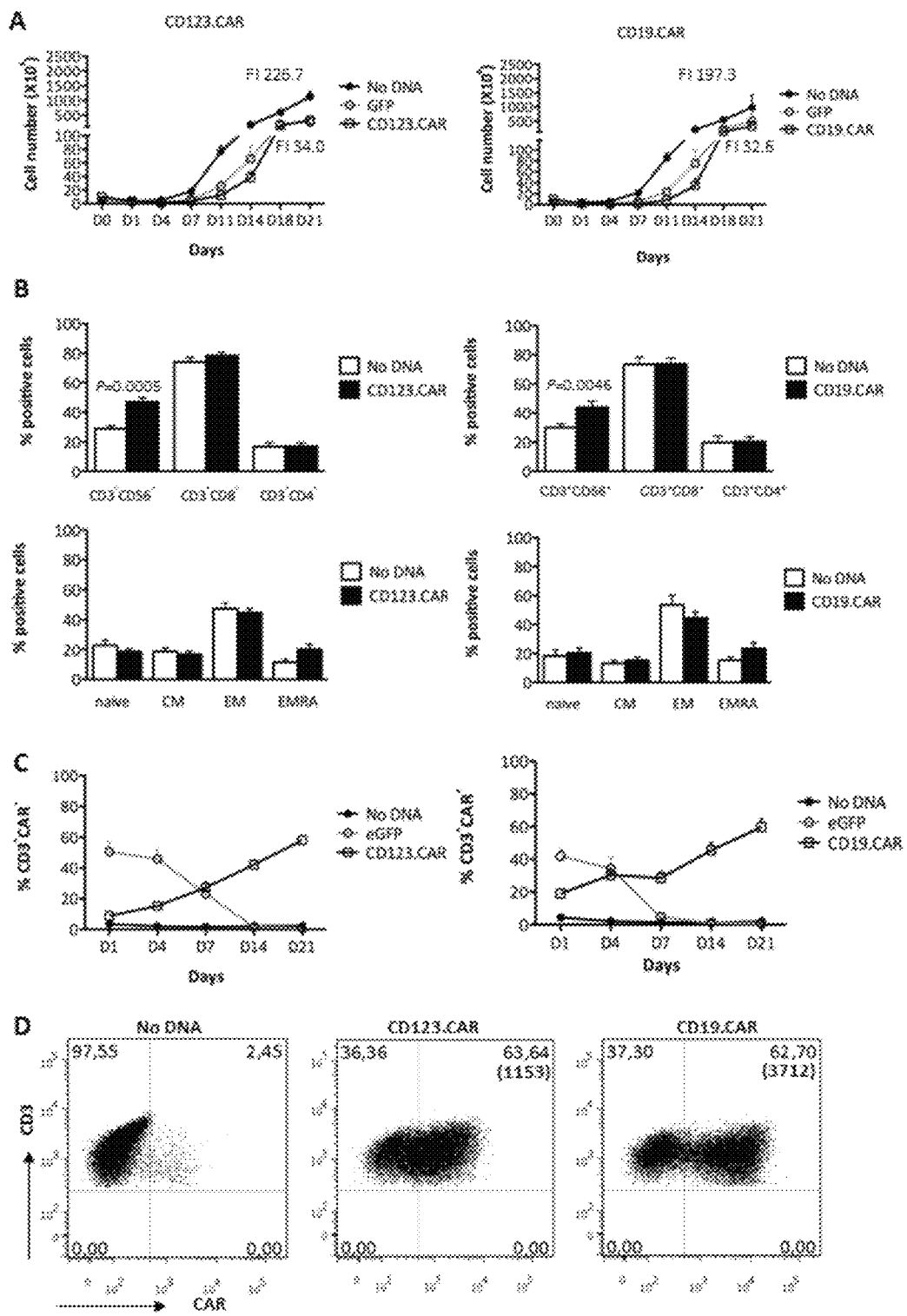

FIG. 3, including FIGS. 3A, B, C and D, describes the genetic modification through the transposon Sleeping Beauty system, the subsequent expansion of CIK-CAR cell populations, their phenotype and their transgene expression. (A) The proliferation of CD3+ cells nucleofected in the absence of DNA with GFP and with transposon encoding for CD123.CAR (left panel) or CD19.CAR (right panel) was followed over time through cell count. (B) The memory phenotype and CD56/CD8/CD4 of CIK CD3+ cell populations after nucleofection of mononuclear cells and differentiation was determined by cytofluorimetric analysis on Day 21. (C) The expression of peptides by genic modification was determined overtime by cytofluorimetric analysis of CD3 and CAR. Mean±SE from 13 donors performed for No DNA and CD123.CAR and for 8 donors for GFP are reported. Mean±SE from 7 donors for No DNA, CD19.CAR and from 5 donors for GFP. (D) The expression of CAR was determined on Day 21 of differentiation. An example representative of 14 donors tested for CD123.CAR and 8 donors tested for CD19.CAR is shown. Numbers represent the percent of positive cells and WI in parenthesis. Coupled two-tail t-test was applied and p values are reported.

Figure 4:
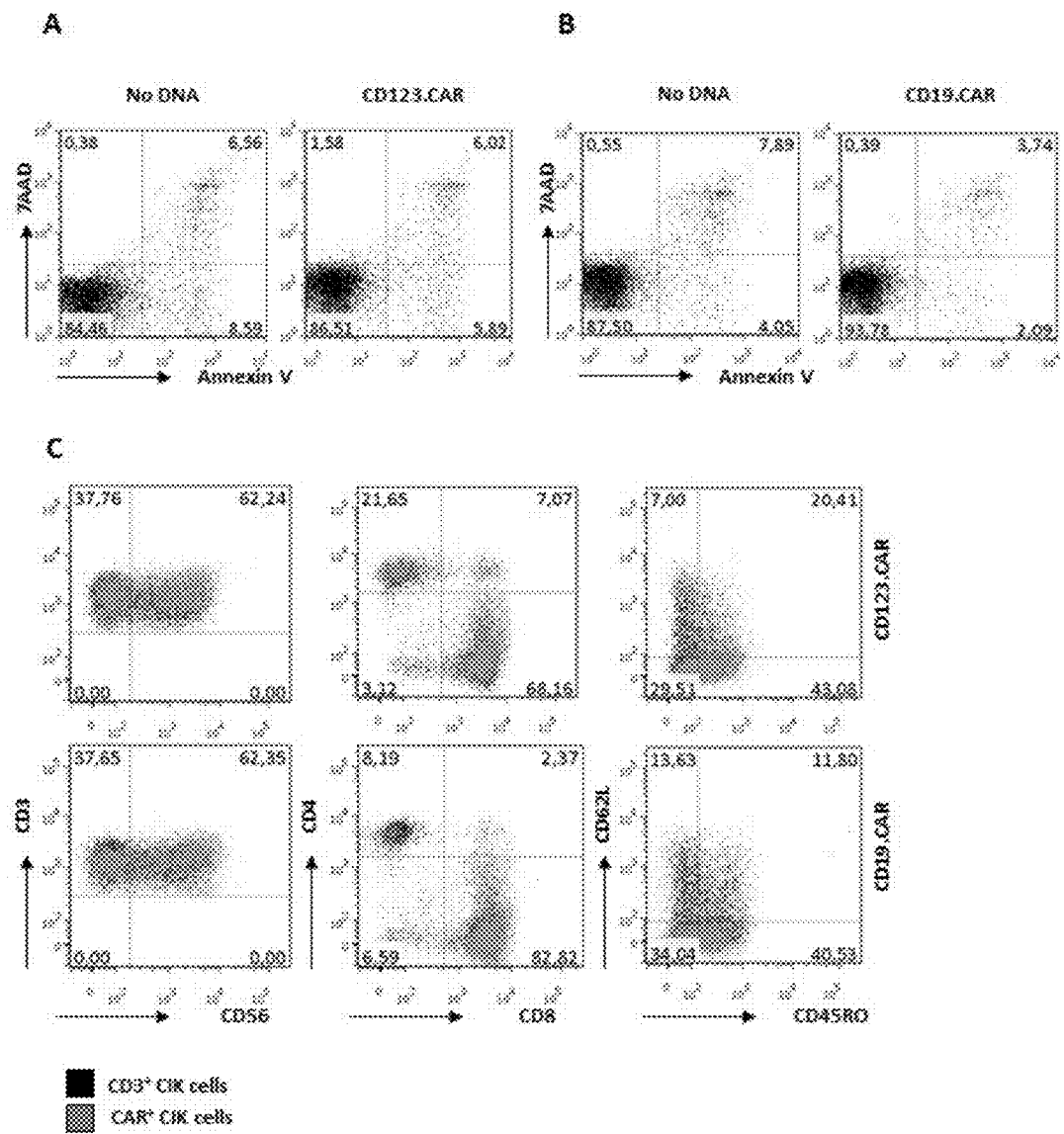

FIG. 4 includes FIGS. 4A, B and C, and describes cell vitality and the homogeneous expression of CAR on T/NK-like and memory subsets of CIK-CAR cell populations modified through the Sleeping Beauty transposon system. (A-B) Vitality of CIK cell cultures was determined as percentage of Annexin V-7-AAD by flow cytometry labeling with PE-conjugated AnnexinV and 7-AAD. An example representative of the 13 donors tested for CD123.CAR and of 8 donors for CD19.CAR is shown. Numbers represent the percentage of positive cells. (C) CAR expression in CD3+CD56+, CD3+CD8+/CD4+ and CD3+CD62L+/CD45RO+ cell populations was determined on Day 21 of differentiation and overlapped as grey dot plot to the total of CD3+ CIK cell populations (black dot plot). An example representative of the 14 donors tested for CD123.CAR and of the 8 donors tested for CD19.CAR is shown. Numbers represent the percentage of CAR positive cells.

Figure 5:
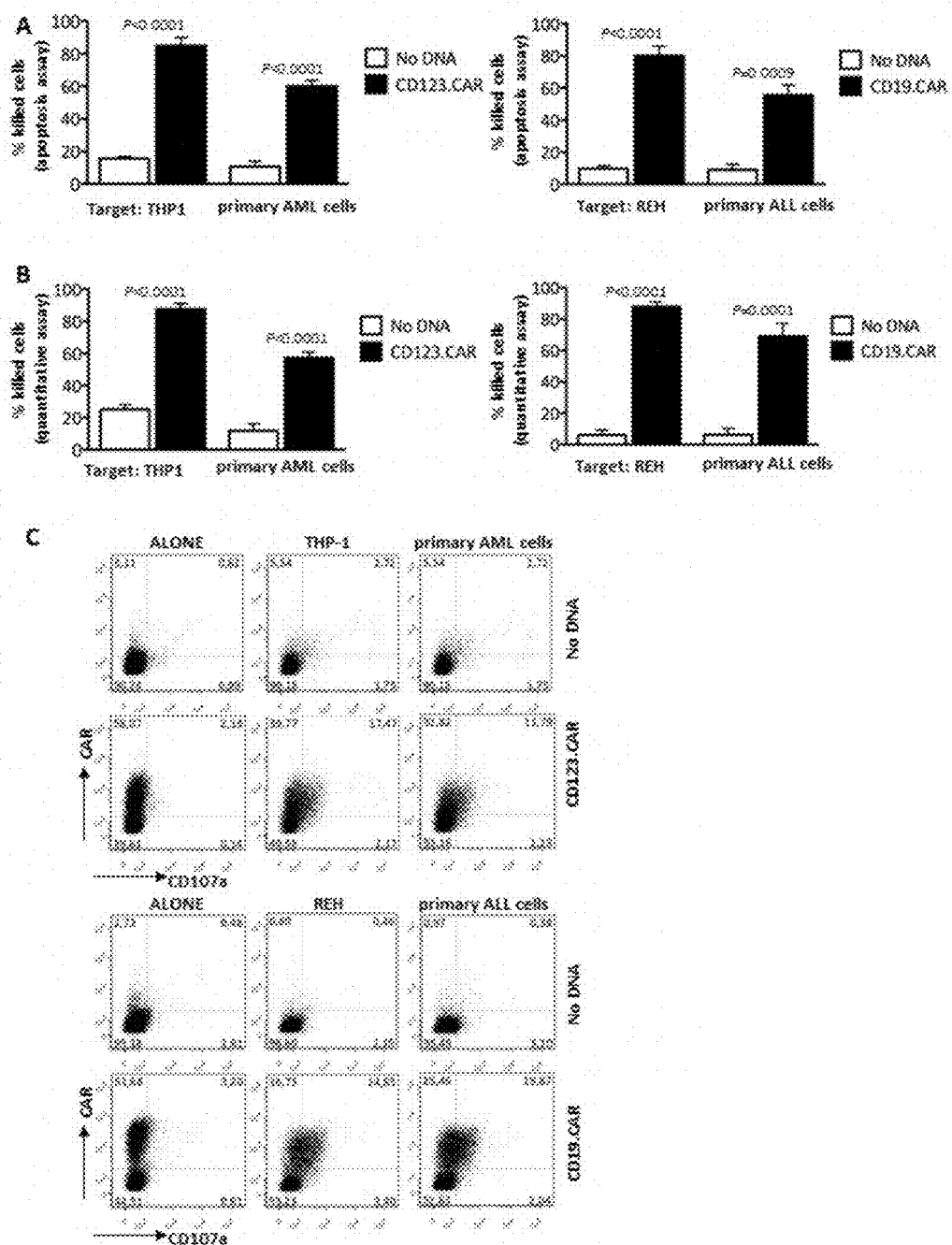

FIG. 5 includes FIGS. 5A, B and C and shows how nucleofection with transposon encoding CD123.CAR and CD19.CAR redirects the activity of CIK-CAR cell populations toward CD123+ and CD19+ cells. (A) The cytotoxic activity of CD123.CAR or CD19.CAR CIK cell populations and of control No DNA against cell lines of acute myeloid leukemia (AML) and acute lymphoblastic leukemia (ALL), THP1 and REH, respectively, and against primary myeloid and lymphoblastic leukemia was determined by apoptosis quantification. CIK-CAR effector cell populations were incubated with target cells in a 5:1 ratio (Effector:Target (E:T)). Dead cells were determined as percentage of (Annexin V+7-AAD−)+(Annexin V+7-AAD+) in CFSE+ (5-(and 6)-carboxyfluorescein diacetate succinimidyl ester, CFDA SE) target cells, by staining with PE-conjugated Annexin V and 7-AAD. Mean±SE from 6 and 8 donors conducted for THP-1 and REH cell lines, and from 10 and 6 donors performed for primary AML and ALL cell lines, respectively, are reported. (B) Cytotoxic activity has been determined in parallel by quantitative determination (E:T ratio=5:1). Dead cells were determined by staining with CD19 FITC for ALL cells and with CD33 FITC or, alternatively, CFSE, for AML cells and quantitative determination of viable cells. Mean±SE from 7 donors performed for THP-1 and for REH, and from 8 and 7 primary cell lines of AML and ALL, respectively, are shown. (C) CD123.CAR or CD19.CAR CIK cell populations were co-cultured with target cells in a E:T ratio of 1:1. Degranulation was measured by CD107a expression in CD3+ T cells stained for the expression of CAR. An example representative of the 9 donors performed for THP-1, of the 7 donors for primary AML cell line and of the 5 donors for REH and primary ALL is shown. Numbers represent the percentage of CD107a+ cells. Two-tail paired t-test was applied and p values are reported.

Figure 6:
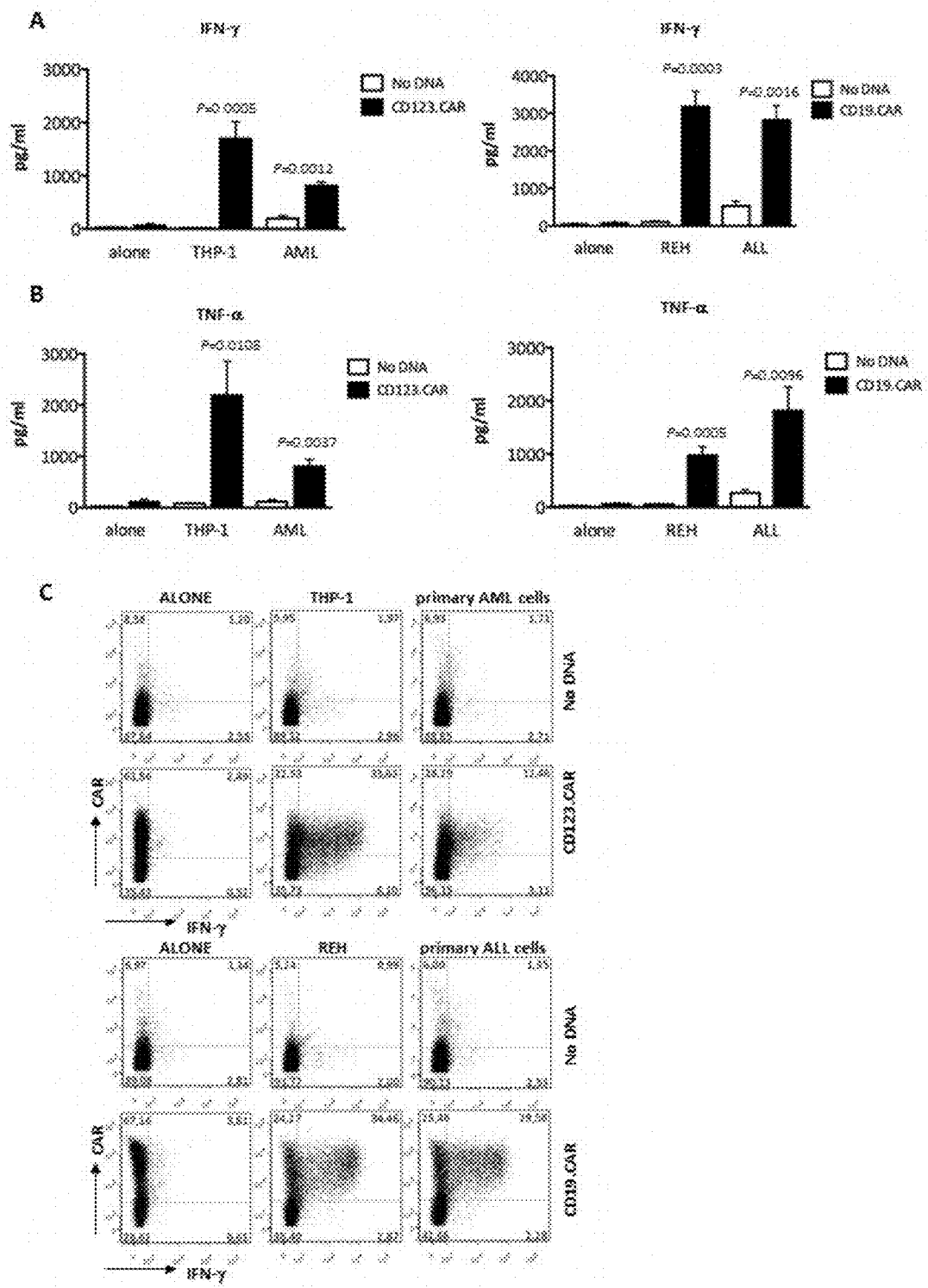

FIG. 6 includes FIGS. 6A, B and C and reports the specific cytokine production by CD123.CAR and CD19.CAR CIK cell populations towards CD123+ and CD19+ cells. The production of IFN-γ (A) and TNF-α (B) from CD123.CAR and CD19.CAR CIK cell populations and from control No DNA was determined by ELISA after stimulation with AML or ALL cell lines, THP-1 and REH, respectively, and with primary AML or ALL cells. Mean±SE from 10 and 8 donors performed for THP-1 and REH respectively, and from 7 donors performed for primary AML and ALL are reported. (C) The expression of IFN-γ was determined in No DNA, CD123.CAR and CD19.CAR cells by intracytoplasmic staining coupled with surface staining for CAR, after stimulation with AML or ALL cell lines, THP-1 and REH, respectively, and primary AML or ALL cells. An example representing the 9 donors performed for CD123.CAR and for CD19.CAR is reported. Numbers represent the percentage of positive cells. Two-tail paired t-test was applied and p values are reported.

Figure 7:
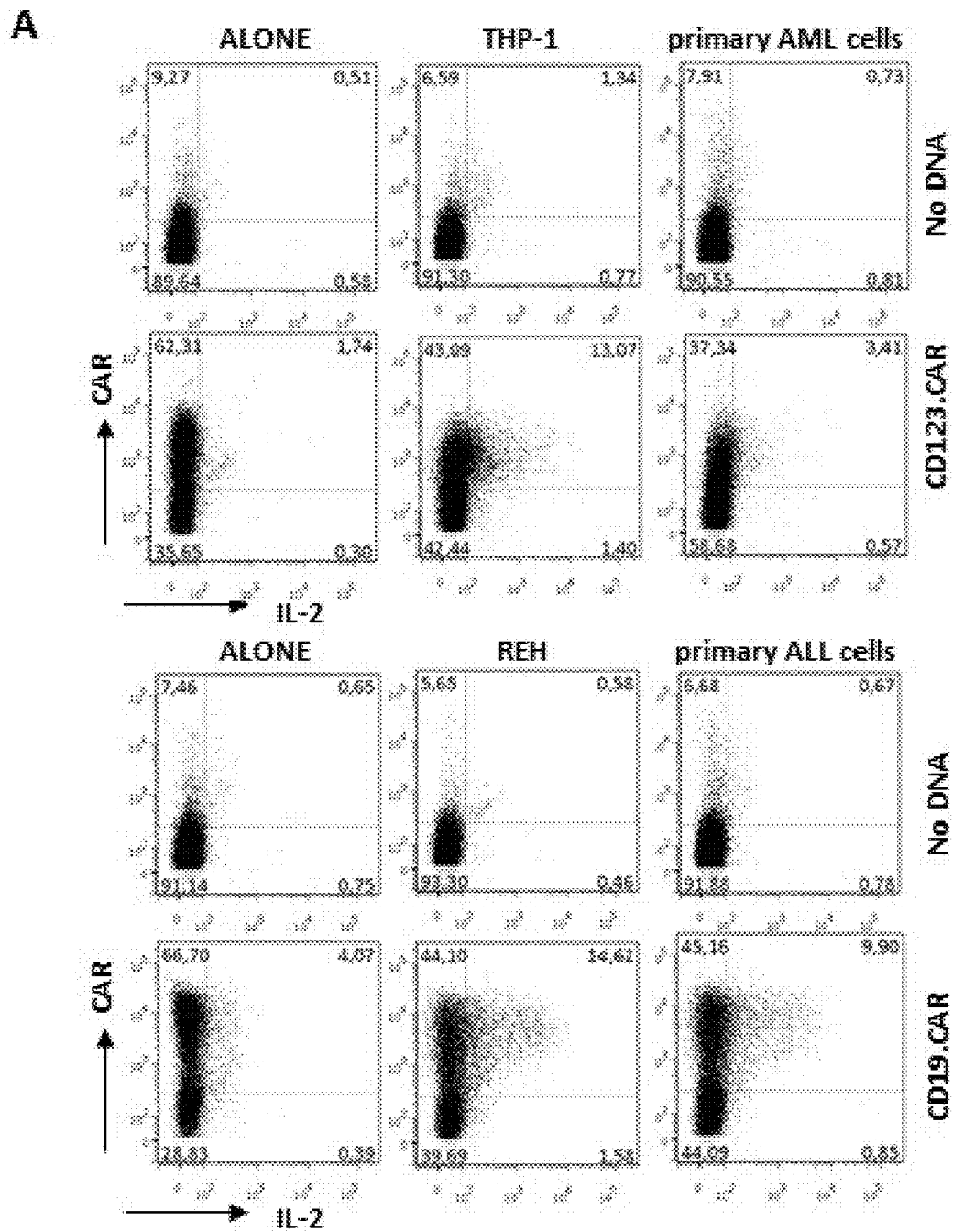

FIG. 7 shows the specific IL-2 production by CD123.CAR and CD19.CAR CIK cell populations towards CD123+ and CD19+ cells. The IL-2 production from CD123.CAR or CD19.CAR CIK cells and from No DNA control was determined by intracytoplasmic staining coupled with surface staining for CAR, after stimulation with the AML or ALL cell lines, THP-1 and REH, respectively, and with primary AML or ALL cells. An example representing the 9 donors performed for CD123.CAR and the 8 donors performed for CD19.CAR is reported. Numbers represent the percentage of positive cells.

Figure 8:
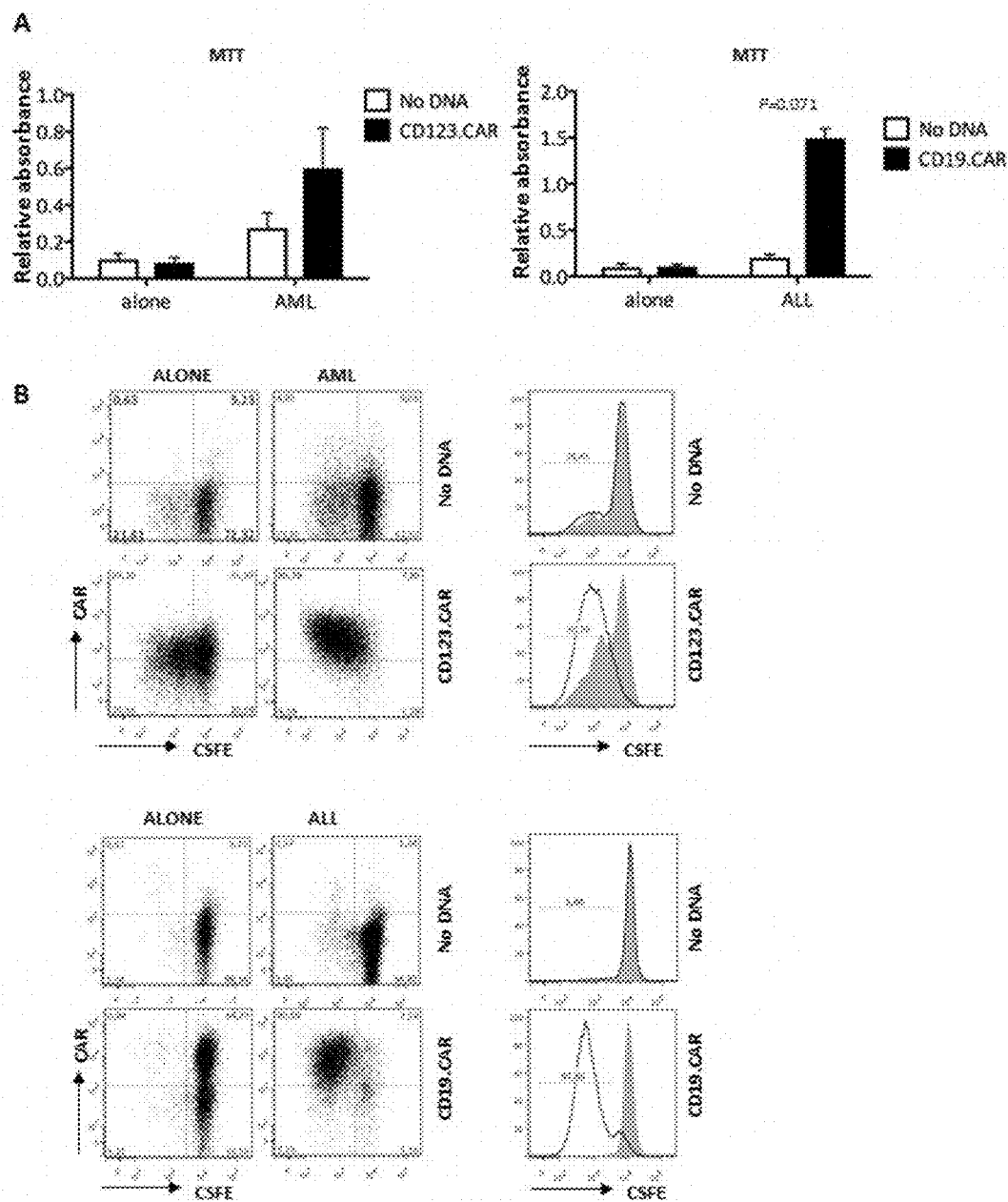

FIG. 8 including FIGS. 8A and B, describes the proliferation of CIK-CAR cell populations modified by SB transposon to express CD123.CAR and CD19.CAR molecules in response to CD123+ and CD19+ cells. (A) Proliferation of No DNA control, CD123.CAR and CD19.CAR CIK cell populations after stimulation with AML or ALL cell lines was determined by the 3-(4,5-dimethylthiazol-2-yl)-2,5-diphenyltetrazolium bromide (MTT) assay. Mean±SE from 5 donors is reported. (B) Proliferation of control No DNA cells, CD123.CAR and CD19.CAR CIK cell populations after stimulation with AML or ALL cell lines was determined by CFSE assay. Data from one donor representative of 5 donors is shown. Numbers represent the percentage of positive cells. Two-tail paired t-test was applied and p values are reported.

Figure 9:
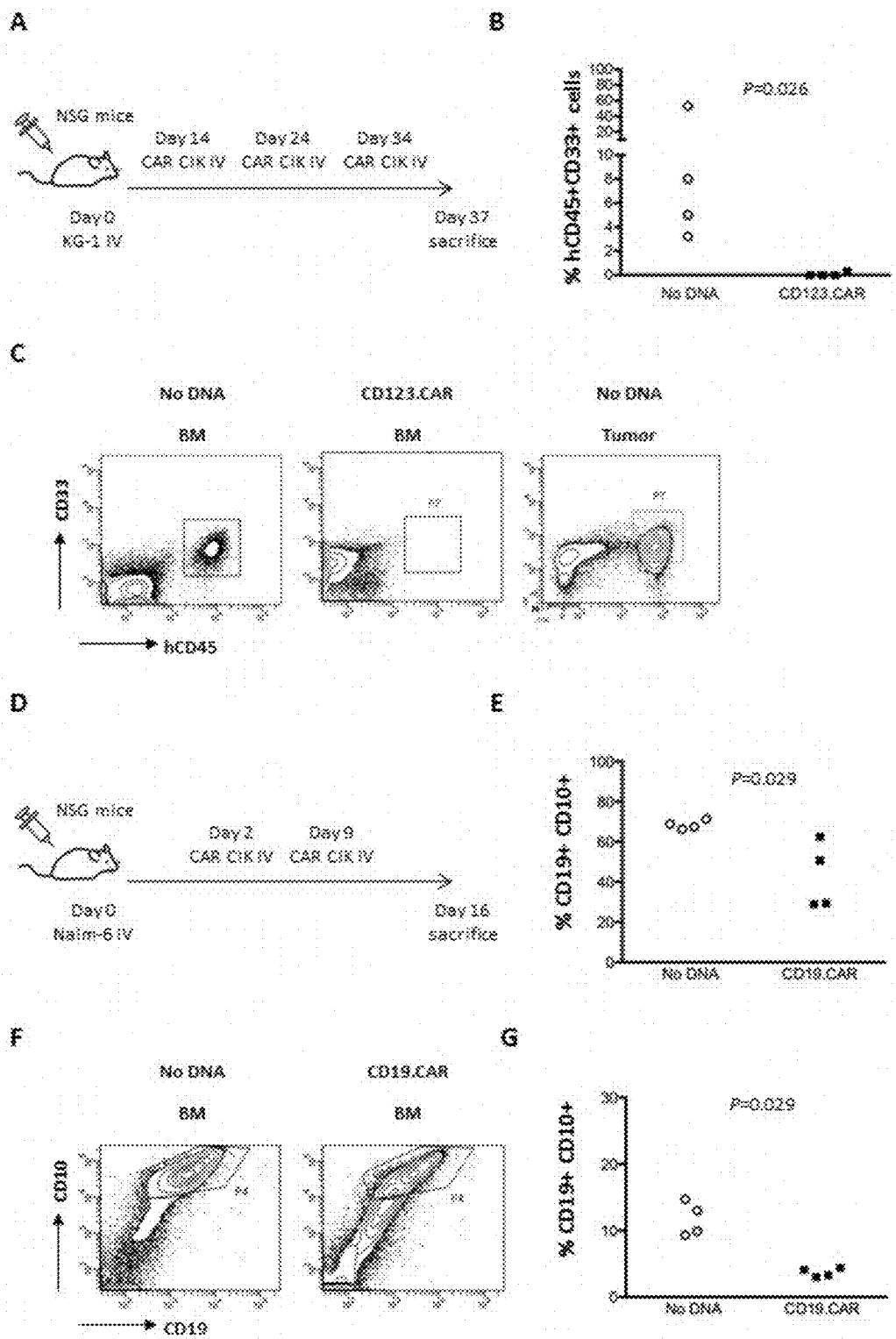

FIG. 9 includes FIGS. 9A, B, C, D, E and F and describes the in vivo antitumor activity of CD123.CAR and CD19.CAR CIK cell populations. (A) Schematic representation of the xenograft experiment. 5×10⁶ KG-1 cells were injected in NSG mice (NOD-SCID-γchain−/−) in the tail vein on day 0. Engraftment was confirmed by cytofluorimetric measurement of mouse CD45⁻ human CD45dim human CD33⁺ cells following bone marrow biopsy. 1×10⁶ cells from CIK cell populations were injected intravenously on day 14, 24 and 34. Mice were sacrificed 37 days after KG-1 injection and bone marrow samples were analyzed by flow cytometry. (B) Engraftment of KG-1 cells in the bone marrow or in extramedullary tumors (rhombus) is shown as presence of mouse CD45⁻ human CD45dim CD33⁺ cells by flow cytometry. Each dot represents a single mouse. (C) Bone marrow and extramedullary tumor analysis in mice at the time of sacrifice. A single donor representative for CD123.CAR CIK cell populations and No DNA control CIK cell populations is shown. (D) Schematic representation of xenograft experiment. 1×10⁶ NALM-6 cells were injected in NSG mice (NOD-SCID-γchain−/−) in the tail vein on day 0. Engraftment was confirmed by cytofluorimetric measurement of mouse CD45⁻ CD10⁺ CD19⁺ cells after bone marrow biopsy. 1×10⁶ cells from CIK cell populations were injected intravenously on day 2 and 9. Mice were sacrificed 16 days after NALM-6 injection and bone marrow samples were analyzed by flow cytometry. (E) Engraftment of NALM-6 in bone marrow was determined as presence of mouse CD45⁻CD10⁺ CD19⁺ cells by flow cytometry. Each dot represents a single mouse. (F) Bone marrow analysis of mice at the time of sacrifice. A donor representative for CD19.CAR CIK cell populations and No DNA control CIK is shown. Two-tail Mann Whitney test was used and p values are reported. (G) Engraftment of NALM-6 in spleen was determined as presence of mouse CD45⁻ CD10⁺ CD19⁺ cells by flow cytometry. Each dot represents a single mouse.

Figure 10:
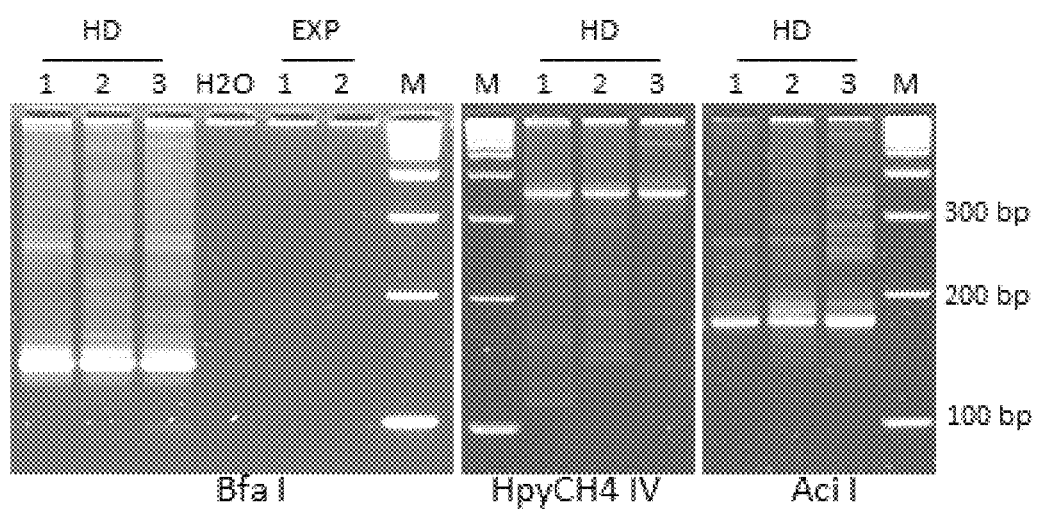

FIG. 10 includes FIG. 10A and describes the LAM PCR analysis in transduced CIK cell populations. (A) Spreadex gel electrophoresis of LAM PCR products obtained from the genomic DNA of SB-marked CIK cell populations form 3 healthy donors (HD). The different restriction enzymes used for each amplification are indicated below each gel. H2O and EXP lanes are negative controls for the LAM PCR steps of linear, first and second exponential amplifications respectively. M, molecular weight marker (fragment size are indicated in bp).

Figure 11:
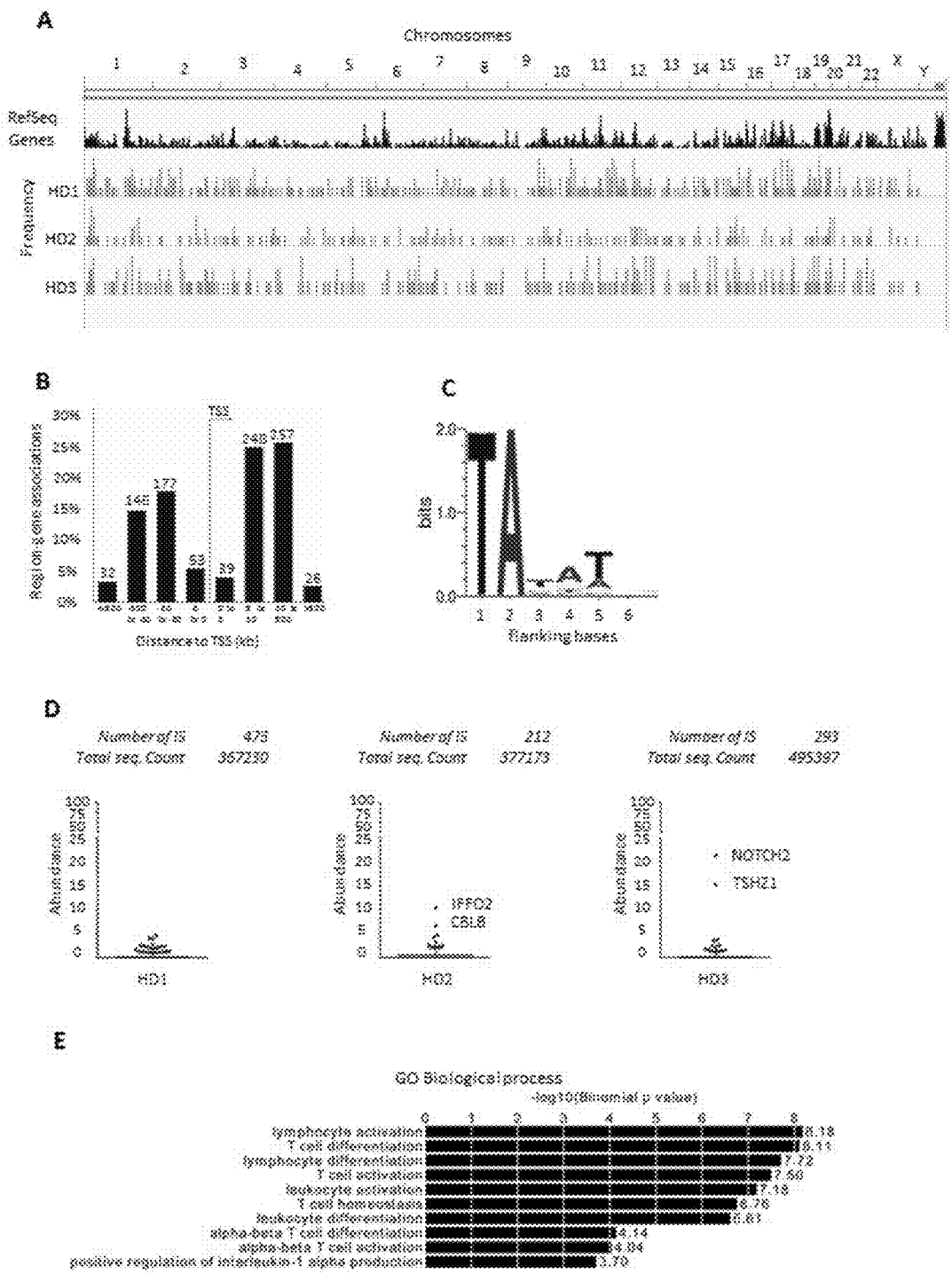

FIG. 11 includes FIGS. 11A, B, C, D and E and describes the integration site analysis in transduced CIK cell populations. (A) Graphic representation of the distribution of integrations at chromosome level in the genome of each HDs. (B) Frequency distribution of SB integrations around the TSS (intervals in Kb, x-axis) of the nearest targeted gene (in %, y-axis). The number of integrations mapping in each genomic interval are indicated above each bar. (C) logo-plot representation of the bases flanking the SB integration sites (position of the bases after the SB integration site are indicated in the X-axis) showing the characteristic TA motif present at each SB integration. (D) Relative clonal abundance of clones harboring specific integration sites (y-axis, % of sequencing reads with respect the total sequencing reads found for each sample). The name of the nearest targeted gene is indicated. (E) Overrepresented gene classes of the Gene Ontology (GO) Biological process targeted by SB integrations.

Figure 12:
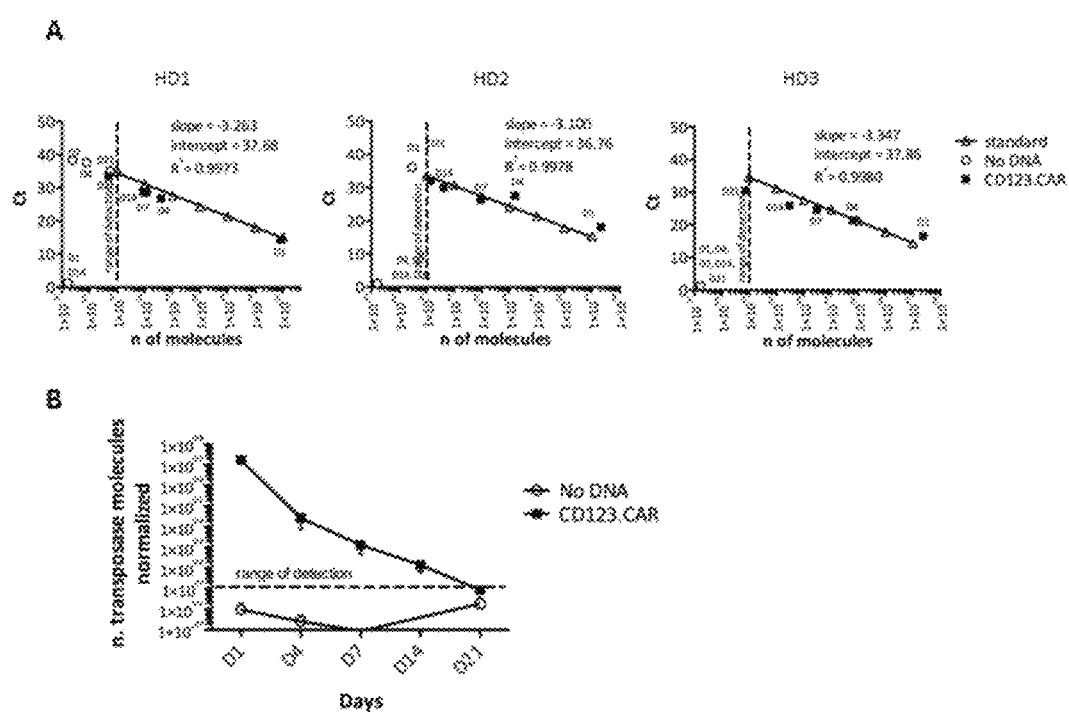

FIG. 12 includes FIGS. 11A and B and describes the transposase clearance in transduced CIK cell populations. (A) Expression analysis of transposase by Quantitative Real Time PCR (Q-RT-PCR) in No DNA control cells and CD123.CAR cells on days 1, 4, 7, 14, 21 from 3 different HD during differentiation. The reactions of standards and samples were performed in the same 96-plate. Slope, Coefficient of determination (R2) and intercept of the standard curve are shown. (B) Evaluation of the transposon expression in CIK cell populations overtime by Q-RT-PCR, as number of transposase molecules normalized to 10⁴ GUS copies. Mean±SE from 3 donors are reported.

Figure 13:
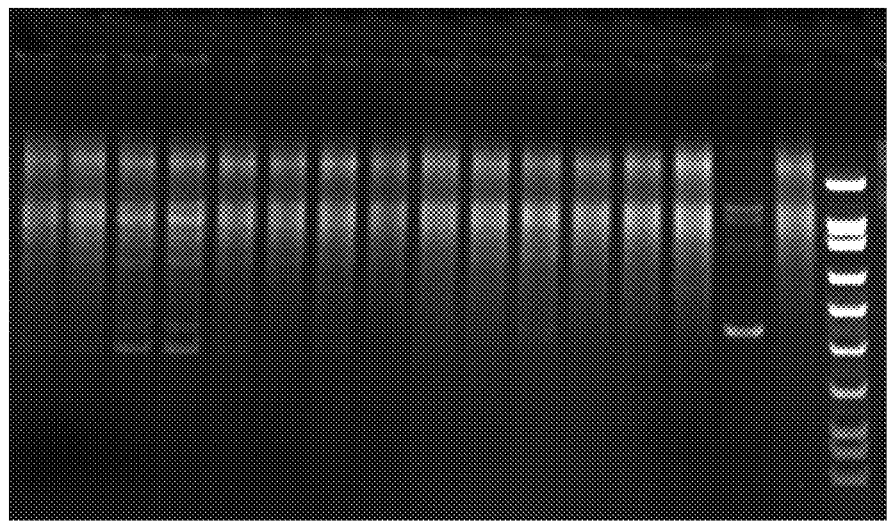
Figure 13:
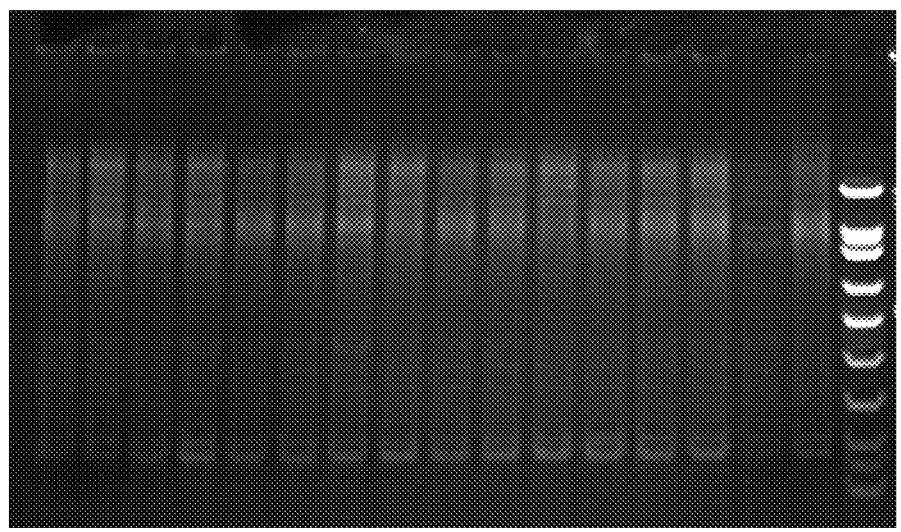

FIG. 13 includes FIGS. 13A and B and describes the TCR-Vβ PCR in CIK-CAR cell populations modified by SB. Diffuse smears are present in CD123.CAR and CD19.CAR CIK cell populations at different times during differentiation, which reflects absence of detectable dominant TCR-Vβ gene rearrangements. (A) PCR for the identification the TCR-Vβ rearrangements (mix 1). (B) PCR for the identification of TCR-VP rearrangements (mix 2). A representative example of a donor of the 3 tested is shown in the figure.

Figure 14:
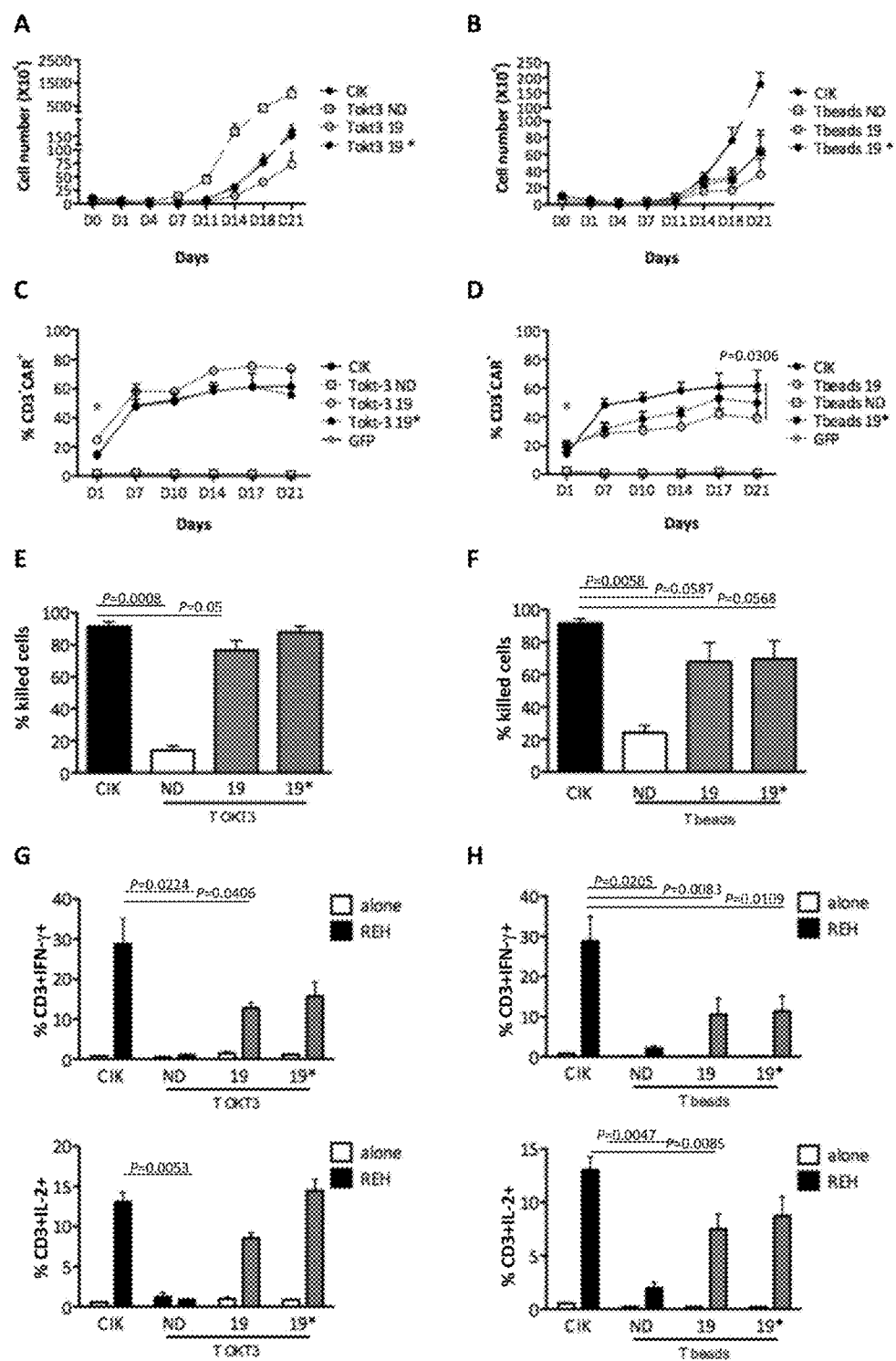

FIG. 14. Comparison of CIK-cell SB transposon platform method with existing methods. (A and B) In comparison with CIK cells, proliferation of cells nucleofected in the absence of DNA (ND), with transposase and transposon encoding CD19.CAR construct in the absence or presence of simultaneous addition of γ-irradiated autologous PBMC (19 and 19*, respectively) stimulated as OKT3-activated (Tokt3, A) or beads-activated (Tbeads, B) conventional T cells, was followed over time until day 21 by cell count. (C and D) PBMC modification was determined over time until day 21 by flow-cytometric analysis of CD3 and CAR expression in Tokt3 (C) or Tbeads (D) cells. As positive control of modification, the Amaxa GFP plasmid was employed. (E and F) Cytotoxic activity of modified Tokt3 (E) or Tbeads (F) cells against REH target cells was determined by apoptosis detection assay. The E:T ratio was 5:1. (G and H) IFN-γ (upper panel) and IL-2 (lower panel) expression of modified Tokt3 (G) or Tbeads (H) cells was determined upon stimulation with REH by intracytoplasmic staining. P-values of the Paired t test (one-tailed) are indicated. Mean±SE are relative to 3 donors.

DETAILED DESCRIPTION OF THE INVENTION

One embodiment of the present invention is a method of generating genetically modified cells in culture comprising:
(a) non-viral transfer of one or more nucleic acids into a population of mononuclear cells in a cell culture;
(b) addition of antigen presenting cells to the cell culture before, during or within about 10 days after the transfer of nucleic acids;
(c) addition of one or more stimulating agents to the cell culture before, during or after the transfer of nucleic acids or the addition of antigen presenting cells;
optionally step (d), addition of one or more stimulating and expanding agents to the cell culture before, during or after the transfer of nucleic acids, the addition of antigen presenting cells or the addition of the stimulating agents;
optionally step (e) addition of one or more differentiating agents to the cell culture before, during or after the transfer of nucleic acids, wherein the differentiating agent differentiates the mononuclear cells in the cell culture; and/or
optionally step (f) isolating the cells from the cell culture to obtain a cell population comprising the modified cells.

One aspect of the present invention is a method of generating genetically modified T cell receptor T cells (e.g., T-TCR), chimeric antigen receptor T cells (e.g., T-CAR) or combinations thereof in culture comprising:

(a) non-viral transfer of one or more nucleic acids encoding one or more T cell receptors or one or more chimeric antigen receptors into a population of mononuclear cells in a cell culture;
(b) addition of antigen presenting cells to the cell culture before, during or within about 10 days after the transfer of nucleic acids;
(c) addition of one or more stimulating agents to the cell culture before, during or after the addition of antigen presenting cells;
optionally step (d), addition of one or more stimulating and expanding agents to the cell culture before, during or after the transfer of nucleic acids, the addition of antigen presenting cells or the addition of stimulating agents; and optionally step (e) addition of one or more differentiating agents to the cell culture before, during or after the transfer of nucleic acids, wherein the differentiating agent differentiates the mononuclear cells in the cell culture; and/or optionally step (f) isolating the cells from the cell culture to obtain cell a cell population comprising the modified cells.

Another aspect of the invention is a method of generating genetically modified cytokine induced killer cells or cell populations expressing T cell receptors (CIK-TCR), chimeric antigen receptors (CIK-CAR) or combinations thereof in culture comprising:
(a) non-viral transfer of one or more nucleic acids encoding one or more T cell receptors, one or more chimeric antigen receptors or combinations thereof into a population of mononuclear cells in a cell culture;
(b) addition of one or more differentiating agents to the cell culture before, during or after the transfer of nucleic acids, wherein the differentiating agents differentiate the mononuclear cells in the cell culture into cytokine induced killer cells;
(c) addition of antigen presenting cells to the cell culture before, during or within about 10 days after the transfer of nucleic acids or addition of differentiating agents;
(d) addition of one or more stimulating agents to the cell culture before, during or after the transfer of nucleic acids, the addition of differentiating agents or the addition of antigen presenting cells;
optionally step (e), addition of one or more stimulating and expanding agents to the cell culture before, during or after the transfer of nucleic acids, the addition of antigen presenting cells or the addition of stimulating agents; and/or optionally step (f) isolating the cells from the cell culture to obtain a cell population comprising the modified cells.

Another embodiment of the present invention is a method of generating genetically modified cells in culture comprising:
(a) obtaining mononuclear cells;
(b) transferring one or more nucleic acids into the mononuclear cells non-virally;
(c) stimulating the cells before, during or within about 10 days after transferring the nucleic acids;
(d) stimulating a receptor of the cells before, during or after transferring the nucleic acids or stimulating the cells;
optionally step (d) differentiating the cells before, during or after the transfer of nucleic acids, wherein the cells are differentiated into cytokine induced killer cells and/or cell populations; optionally step (e), stimulating and expanding the cells before, during or after the transfer of nucleic acids, stimulating the cells or stimulating a receptor of the cells; and/or optionally step (f) isolating the cells from the cell culture to obtain a cell population comprising the modified cells.

Another embodiment of the present invention is a method to genetically modify, differentiate, stimulate and/or expand cells in culture comprising:
(a) non-viral transfer of one or more nucleic acids into a population of mononuclear cells in a cell culture;
(b) addition of a antigen presenting cells to the cell culture before, during or within about 10 days after the transfer of nucleic acids;
(c) addition of one or more stimulating agents to the cell culture before, during or after the transfer of nucleic acids or the addition of antigen presenting cells;
optionally step (d) addition of one or more differentiating agents to the cell culture before, during or after the transfer of nucleic acids, wherein the differentiating agents differentiate the mononuclear cells in the cell culture into cytokine induced killer cells and/or cell populations; optionally step (e), addition of one or more stimulating and expanding agents to the cell culture before, during or after the transfer of nucleic acids, the addition of antigen presenting cells or the addition of stimulating agents; and/or optionally step (f) isolating the cells from the cell culture to obtain a cell population comprising the modified cells.

In another embodiment, the present invention includes genetically modified cells made by the methods of the present invention.

In another embodiment, the present invention includes genetically modified cell populations made by the methods of the present invention.

In a preferred embodiment, the present invention includes genetically modified T cell receptor cells, chimeric antigen receptor cells or combinations thereof, preferably T-TCR, T-CAR, CIK-TCR and CIK-CAR cells or combinations thereof, made by the methods of the present invention.

In another preferred embodiment, the present invention includes cell populations comprising genetically modified T cell receptor cells, chimeric antigen receptor cells or combinations thereof, preferably T-TCR, T-CAR, CIK-TCR, CIK-CAR cells or combinations thereof, made by the methods of the present invention.

In another embodiment, the present invention includes a formulation comprising the genetically modified cells and/or cell populations of the present invention or made by the methods of the present invention. Preferably, the formulation is a pharmaceutical formulation and comprises binders, fillers, carriers, preservatives, stabilizing agents, emulsifiers, and/or buffers. Preferably, the formulation comprises diluents and excipients, for example, water, saline, and dextrose.

In another embodiment, the present invention is a method of treating or preventing a disease or disorder in a mammal, preferably a human, in need thereof comprising administering to the mammal an effective amount of the genetically modified cells and/or cell populations of the present invention or made by the methods of the present invention. Preferably, the disease or disorder is a hematologic disorder, a leukemia, a lymphoma, a solid tumor, a viral infection, an inflammatory disease or disorder, or an autoimmune disease or disorder.

In another embodiment, the present invention includes non-viral genetically modified cells, preferably genetically modified T cell receptor cells, chimeric antigen receptor cells or combinations thereof, cell populations and/or cell cultures comprising such cells, more preferably, T-TCR, T-CAR, CIK-TCR, CIK-CAR cells or combinations thereof, cell populations and/or cell cultures comprising such cells, and more preferably CIK-CAR19, CIK-CAR123 cells or combinations thereof, cell populations comprising such cells and/or cell cultures comprising such cells, wherein the cells, cell populations and/or cell cultures further comprise: a) expression levels of transgenes, preferably expression levels of TCR and/or CAR, of at least about 10-60%, preferably at least about 20-30% and more preferably at least about 50-60%; b) at least about 10%, preferably at least about 25% CIK-TCR, CIK-CAR, CIK-CAR19, CIK-CAR123 cells or combinations thereof; c) a fold increase in expansion of the cell population greater than about 10 at about 21-28 days of culture; and/or d) optionally at least about 10-90%, about 60-90% or about 80-90% of viable T cell receptor cells, chimeric antigen receptor cells, T-TCR, T-CAR, CIK-TCR, CIK-CAR, CIK-CAR19, CIK-CAR123 cells or combinations thereof.

In another embodiment, the present invention includes non-viral genetically modified cell populations or cell cultures comprising genetically modified T cell receptor cells, chimeric antigen receptor cells, preferably T-TCR, T-CAR, CIK-TCR, CIK-CAR cells or combinations thereof and more preferably CIK-CAR19, CIK-CAR123 cells or combinations thereof, wherein the cell populations or cell cultures further comprise: a) expression levels of transgenes, TCR and/or CAR of at least about 10-60%, preferably at least about 20-30% and more preferably at least about 50-60%; b) at least about 10%, preferably at least about 25% CIK-TCR, CIK-CAR, CIK-CAR19, CIK-CAR123 cells or combinations thereof c) a fold increase in expansion of the cell population greater than about 10 at about 21-28 days of culture; and/or d) at least about 10-90%, preferably about 60-90% and more preferably about 80-90% of viable T cell receptor cells, chimeric antigen receptor cells, T-TCR, T-CAR, CIK-TCR, CIK-CAR, CIK-CAR19, CIK-CAR123 cells or combinations thereof.

Preferably, the non-viral genetically modified cells and/or cell populations comprise T cell receptor cells or chimeric antigen receptor cells and more preferably CIK-TCR or CIK-CAR cells and/or cell populations.

Preferably, the population of mononuclear cells in the cell culture comprises: peripheral blood mononuclear cells, bone marrow derived mononuclear cells, umbilical cord blood derived mononuclear cells, lymphocytes, monocytes, dendritic cells, macrophages, T cells, naive T cells, memory T cells, natural killer cells, hematopoietic stem cells, pluripotent embryonic stem cells, induced pluripotent stem cells or combinations thereof.

Preferably, the population of non-viral genetically modified cells in the cell culture comprises: autologous or allogeneic cells or combinations thereof. Preferably, the population of mononuclear cells in the cell culture comprises at least about $10 \times 10^6$ mononuclear cells.

Preferably, the nucleic acids are exogenous nucleic acids and preferably the nucleic acids encode antigen receptors such as T cell receptors, chimeric antigen receptors or combinations thereof.

Preferably, the method comprises electroporation and/or nucleofection.

Preferably, the amount of nucleic acids is from about 0.1 to about 100 µg and more preferably about 5 µg. More preferably, the amount of nucleic acids is about 5 µg of a DNA plasmid encoding SB11 transposase and about 15 µg of a DNA plasmid encoding an expression cassette flanked by IR/DR sequences.

Preferably, the non-viral transfer of nucleic acids comprises: transposons, transposases, Zn-finger nucleases, integrases, transcription activator-like effectors, the clustered regularly interspaced short palindromic repeats, sequence-specific recombinase systems able to integrate nucleic acids by recombination between attachment sites or combinations thereof.

Preferably, the nucleic acids comprise: one or more plasmids or RNA encoding a transposase enzyme and one or more plasmids comprising a transposon consensus sequence.

Preferably, the nucleic acids encode for chimeric antigen receptors for one or more antigens comprising: CD19, CD123, CD20, CD23, CRLF2, CD44v6, CD33, CS1 CD38, Her2, EGFr and CA125 antigens or combinations thereof. Preferably, the nucleic acids also encode for one or more safety systems, more preferably suicide genes such as the inducible Caspase 9 system.

Preferably, the non-viral transfer of nucleic acids comprises: Sleeping Beauty, PiggyBac, TALEs, phiC31 or CRISPR/Cas. Preferably, the nucleic acids are stably integrated within the genome of the mononuclear cells in the cell culture.

Preferably, the differentiating agents comprise one or more cytokines such as IFN-γ, IL-4, IFN-α, IL-10, IL-12, IL-6, IL-21, IL-23, IL-1β, TGF-β, molecules that promote differentiation, or combinations thereof. More preferably the differentiating agent is interferon gamma (IFN-γ).

Preferably, the differentiating agents are added in an amount of from about 10 U/ml to about 10,000 U/ml, more preferably about 1000 U/ml.

Preferably, the differentiating agents are added within about 10 days, or between 0 and about 10 days, more preferably within about 5 days, or between 0 and about 5 days, after the transfer of nucleic acids. More preferably, the differentiating agents are added within about 1 day, or between 0 and about 1 day, more preferably within about 2 hours, or between 0 and about 2 hours, after the transfer of nucleic acids. Most preferably, the differentiating agent is IFN-γ added in an amount of about 1000 U/ml within about 2 hours after the transfer of nucleic acids.

Preferably, the antigen presenting cells comprise: irradiated mononuclear cells or Mitomycin-C treated mononuclear cells and combinations thereof; or lymphocytes, monocytes, dendritic cells, macrophages, artificial antigen presenting cells (e.g., K562 cells transfected to co-express one or more CD19, CD64, CD86, CD137L and membrane bound IL-15 (e.g. as described in 26) and L cells transfected to co-express one or more CD32, CD58 and CD80 (e.g., as described in 42) optionally irradiated or treated with Mitomycin-C and combinations thereof. More preferably, the antigen presenting cells are irradiated mononuclear cells and more preferably irradiated peripheral blood mononuclear cells.

Preferably, the antigen presenting cells are added to the cell culture within about 10 days after the transfer of nucleic acids or between 0 and about 10 days, more preferably within about 5 days after the transfer of nucleic acids or between 0 and about 5 days. More preferably, the antigen presenting cells are added to the cell culture within about 24 hours or between 0 and about 24 hours, and more preferably within about 2 hours or between 0 and about 2 hours, after the transfer of nucleic acids.

Preferably the antigen presenting cells are added to the cell culture once before, during or within about 10 days after the transfer of nucleic acids.

Preferably the antigen presenting cells and the mononuclear cells are in a ratio of antigen presenting cells:mononuclear cells from about 1:20 to up to about 5:1, more preferably about 1:2. The antigen presenting cells can also be stimulating subpopulations derived from mononuclear cells that are not irradiated or treated with Mitomycin C, preferably monocytes and/or dendritic cells. Preferably in a ratio of monocytes:mononuclear cells from about 1:100 to about 5:1, more preferably about 1:10 or a ratio of dendritic cells:mononuclear cells from about 1:100 to about 5:1, more preferably 1:20 or 1:10.

Preferably the antigen presenting cells and the population of cells in the cell culture for non-viral transfer of nucleic acids are from the same source.

Alternatively, the antigen presenting cells are from a source genetically non-identical to the source providing the mononuclear cells for transfer of nucleic acids or from the same source providing the mononuclear cells for transfer of nucleic acids or combinations thereof.

Preferably, the stimulating agents used to generate genetically modified cells and/or cell populations comprise: agents that stimulate antigens, agents that stimulate $CD3^+$ cells, TCR stimulating agents, anti-CD3 antibodies, anti-CD28 antibodies, anti-TCR antibodies, beads (e.g., CD3/CD28 beads), polyclonal non-TCR restricted stimulation, (e.g., with superantigens, PHA, PMA and ionomycin), anti-CD3-loaded artificial antigen presenting cells, optionally irradiated or treated with Mitomycin-C (e.g. irradiated OKT3-loaded K562-derived artificial antigen presenting cells), and combinations thereof. More preferably, the anti-CD3 antibody is OKT3.

Preferably, the stimulating agents used to generate genetically modified cytokine induced killer cells and/or cell populations comprise: agents that stimulate antigens, agents that stimulate $CD3^+$ cells, TCR stimulating agents, anti-CD3 antibodies, anti-CD28 antibodies, anti-TCR antibodies, beads (e.g., CD3/CD28 beads), polyclonal non-TCR restricted stimulation, (e.g., with superantigens, PHA, PMA and ionomycin), anti-CD3-loaded artificial antigen presenting cells, optionally irradiated or treated with Mitomycin-C (e.g. irradiated OKT3-loaded K562-derived artificial antigen presenting cells), and combinations thereof. More preferably, the anti-CD3 antibody is OKT3.

Preferably, the stimulating agents are added in an amount of from about 5 ng/ml to about 100 µg/ml, more preferably about 50 ng/ml.

Preferably, the stimulating agents are added to the cell culture after the transfer of nucleic acids. More preferably, the stimulating agents are added to the cell culture within about 10 days, or between 0 and about 10 days, preferably within about 5 days, or between 0 and about 1 day, and more preferably within about 1 day, or between 0 and 1 day, after the transfer of nucleic acids.

Preferably the stimulating agents are added to the cell culture once before, during or after the transfer of nucleic acids or the addition of antigen presenting cells.

Preferably, the mononuclear cells are peripheral blood mononuclear cells, the nucleic acids encode for a T cell receptor or a chimeric antigen receptor, the antigen presenting cells are irradiated peripheral blood mononuclear cells added within about 24 hours, preferably 2 hours, after the transfer of nucleic acids, the stimulating agent is a TCR stimulating agent, preferably OKT-3, added within about 1 day after transfer of the nucleic acids and the stimulating and expanding agent is IL-2 added at about the same time as the TCR stimulating agent (e.g., within about 1 day after transfer of the nucleic acids), or after the addition of the TCR stimulating agent.

Preferably the stimulating and expanding agents are added to the cell culture within about 10 days, or between 0 and 10 days, after the transfer of the nucleic acids, more preferably within about 1 day, or between 0 and about 1 day, after the transfer of nucleic acids and optionally about two or three times/week thereafter.

Preferably the stimulating and expanding agents are added to the cell culture at least once before, during or after the transfer of nucleic acids, the addition antigen presenting cells or the addition of stimulating agents.

Preferably, the stimulating and expanding agents are cytokines that bind the common γ chain such as IL-2, IL-7, IL15, IL-21 or combinations thereof and more preferably, the stimulating and expanding agent is IL-2.

Preferably the steps of the methods of the present invention collectively take place within about a 10-day time window or between 0 to about a 10-day time window and more preferably within about a 24-hour time window or between 0 to about 24 hours.

Preferably, the modified cells express one or more receptors for the same antigen, different antigens or combinations thereof. More preferably, the T cell receptor cells or chimeric antigen receptor cells and/or cell populations comprise T cells expressing one or more chimeric antigen receptors for the same antigen, different antigens or combinations thereof. More preferably, the T cells are cytokine induced killer cells and/or cell populations. More preferably, the T cell receptor cells or chimeric antigen receptor cells comprise one or more receptors for a CD19 antigen or a CD123 antigen.

In another embodiment of the present invention, mononuclear cells are modified with nucleic acids and expression cassettes encoding for peptides, carbohydrates or glycolipids with immunotherapeutic activity by any known method. Non-viral transfer of nucleic acids, preferably via non-viral vectors, is designed to induce the ectopic expression of desired genes in cells of the immune system preferably under the control of promoters and more preferably eukaryotic promoters such as MNDU3 or other promoters suitable for this purpose.

In another embodiment the nucleic acids can also encode for an expression cassette capable of stably inserting into the genome by an integration system based on non-viral transfer such as: transposon systems able to integrate nucleic acids by non-homologous recombinant mechanisms (e.g., Sleeping Beauty (38) and PiggyBac (23)); RNA-guided gene editing/targeting systems able to integrate nucleic acids by homologous recombination (e.g., Zn-finger nucleases, transcription activator-like effectors (TALEs) or clustered regularly interspaced short palindromic repeats (CRISPR/Cas)); sequence-specific recombinase systems able to integrate nucleic acids by recombination between attachment sites (att) (e.g., phiC31); integrases or combinations of the above. Preferably, the expression cassette can be combined in a multi-component system, preferably a two-component system, such as one or more plasmids encoding a transposase enzyme, and one or more plasmids containing the consensus sequences of the transposon, such as Sleeping Beauty (38) and PiggyBac (23) to obtain an efficient non-viral gene transfer. Preferably, the expression cassette can be combined in a multi-component system, preferably a two component system, that includes one or more plasmids or one or more RNA species combined with one or more plasmids or one or more DNA species, the first encoding a transposase enzyme, the second containing the consensus sequences of the transposon, such as Sleeping Beauty (43) or PiggyBac (23). A non-limiting example includes the use of the integrase of the Sleeping Beauty system SB11 transposase cloned, modified and under control of a CMV promoter and the use of the sequence IR/DR of Sleeping Beauty.

In a specific embodiment, known nucleic acids encoding for peptides with immunotherapeutic activity are used. Such nucleic acids comprise human genes that modulate, and preferably increase, the immunotherapeutic activity and the persistence of cells, preferentially differentiated cells, starting from modified precursors for the clinical application in human patients. Accordingly, the activity of the immune system can be potentiated or redirected with co-stimulating molecules, cytokines or transcriptional factors, inducing immunostimulating or immunosuppressive responses according to the selected application (44).

In a preferred embodiment of the present invention, the exogenous nucleic acids encode for artificial receptors such as tumor-specific T cell receptors (TCRs) and chimeric antigen receptors (CARs) (3), in order to stimulate a potent antitumor response and/or minimize the risk of GvHD.

In a preferred embodiment, the present invention includes the modification of mononuclear cells, preferably PBMCs, with one or more CAR molecules specific for CD19, a pan-B cell surface antigen that is considered as a potential immunotherapy target for B-cell neoplasms, such as chronic lymphoblastic leukemia (CLL), acute lymphoblastic leukemia (ALL) and non-Hodgkin lymphoma (NHL). Several anti-CD19 CARs are currently under clinical evaluation (10, 45), showing a good profile of efficacy and toxicity, since CD19 is absent in staminal hematopoietic cells and expression is limited to B cells and to some follicular dendritic cells in healthy subjects. Moreover, its expression is lost during maturation of B-lymphocytes to plasma cells.

In a highly preferred embodiment, the exogenous nucleic acids in the form of circular DNA plasmids include an expression cassette encoding a CAR specific for human CD19 antigens, comprising: an extracellular domain comprised of a single chain Fv fragment (scFv) including one VH and one VL chain of the monoclonal antibody anti-CD19 (e.g., clone fmc63 (45)); a transmembrane domain, such as the CD28 domain; and an intracellular domain comprising, for example, the signaling domain of the zeta chain of TCR, including the co-stimulatory domains of the CD28 and OX40.

In another preferred embodiment, the present invention includes the modification of effector cell precursors, preferably mononuclear cells and more preferably PBMCs, with one or more CAR molecules specific for CD123 (46, 47). In the context of AML, the CD123 molecule is overexpressed by leukemic blasts, by CD34$^+$ progenitors and by Leukemic Stem Cells (LSC) compared to normal hematopoietic cells, with an expression range between 45% and 95% in leukemic cells of patients affected by AML. Moreover, CD123 is expressed by a low percentage of cells and at significantly low Mean Fluorescence Intensity (MFI) levels in the staminal compartment of healthy donors.

In a particularly preferred embodiment, the exogenous nucleic acids, preferably in the form of circular DNA plasmids, include one or more expression cassettes encoding for one or more CAR molecules specific for a human CD123 antigen, comprising: an extracellular domain comprised of a single chain Fv fragment (scFv) including one VH and one VL chain of the monoclonal antibody anti-CD123 (e.g., clone 7G3, CSL Limited, Australia); a transmembrane domain, such as the CD28 transmembrane domain; and an intracellular domain comprising, for example, the signaling domain of the zeta chain of TCR, including the co-stimulatory domains of the CD28 and OX40.

In another embodiment, the present invention includes the modification of mononuclear cells, preferably PBMCs, with one or more CARs specific for CD19 in combination with one or more CARs specific for CD123, including bispecific forms. The expression can also be stoichiometric and/or co-localized. In addition, the signaling domains can be modulated in the CAR molecules in order to have "full" activation only when two or more CARs are engaged or, alternatively, novel bispecific CAR molecules can also be created (e.g., CAR123.CAR33, TanCAR).

Beyond CD123 and CD19, the present invention also includes the modification of mononuclear cells, preferably PBMCs, with one or more other target antigens, either alone or in combination, including bispecific forms, related to B-cell disorders, such as CD20, CD23, CRLF2, and myeloid disorders, such as Lewis Y, CD44v6 and CD33, and to multiple myeloma (MM)-specific targets, such as CS1, CD38, and to other targets associated with or specific for hematologic cancers and solid tumors, including Her2, EGFr, and CA125.

A further embodiment of the invention relates to the genetic modification of mononuclear cells, preferably PBMCs, by introduction through known methods of one or more safety systems that can prevent unexpected toxic effects of the modified mononuclear cells by eliminating modified mononuclear cells from the organism in case of adverse events (4). In this context, a preferred safety system is obtained by the incorporation of an inducible suicide gene in the modified mononuclear cells to optimize the safety profile in the context of adoptive cell therapy. Preferably, the safety system is the inducible Caspase 9 system (iC9).

Accordingly, the present invention comprises also the combined modification of effector cells with TCRs, CARs, cytokines and/or suicide genes.

After modification, mononuclear cells can be stimulated immediately and infused in patients. Preferably, populations of mononuclear cells can be stimulated and expanded for days or weeks. Moreover, populations of cells made by the methods of the present invention that have been genetically modified, differentiated, stimulated, and/or expanded cells can be cryopreserved.

The method of the invention allows for the generation of a large scale cell population capable of proliferating, producing cytokines, and killing cells (e.g., cancer cells) that is redirected in its activity based on the genetic modification applied. Among the cell populations, of particular relevance are cell populations comprising CIK cells, a particular NK-like T cell population characterized by a basal antitumor activity (WO1999/046365 and WO2011/103882), and memory stem T cells (Tscm), characterized by a superior proliferative and antitumor activity. In one preferred embodiment, such populations of differentiated cells, starting from mononuclear cells modified with the chimeric gene containing the anti-CD19 CAR molecule or the anti-CD123 CAR molecule, are redirected to identify and kill a CD19-positive tumor cell target or a CD123-positive tumor cell target respectively, with specific production of cytokines and proliferation.

The method of the invention finds several known applications such as adoptive cell therapy with gene-modified effector cells of the immune system for the treatment of disorders and diseases such as cancer, tumors, autoimmune disorders and immune response-related disorders and diseases such as viral infections.

For example, cell populations comprising T cells, and preferably cell populations comprising CIK cells expressing TCR or CAR, and preferably such cells and/or cell populations made by the method of the present invention, can be exploited for the treatment of cancers and tumors, where the CD19 surface antigen is overexpressed, such as B-type acute lymphoblastic leukemias, chronic lymphocytic leukemia, lymphomas. Potential candidates for the application of anti- CD19 CAR are also autoimmune diseases where the B-lymphoid compartment is involved, such as, among the most relevant, anemias, autoimmune platelet disorders and neutropenia, rheumatoid arthritis, lupus erythematosus systemicus (LES), chronic inflammatory bowel disease, autoimmune hepatitis, Chron's disease, multiple sclerosis, severe myasthenia, scleroderma, autoimmune thyroiditis and autoimmune vasculitis. In onco-hematology, a highly relevant application with unmet medical need is the relapse of B-lymphoid pathologies following bone marrow transplant, with the possible use of cell populations comprising T cells, and preferably cell populations comprising CIK cells, redirected against CD19 antigen, and preferably such cells made by the method of the present invention, to eradicate leukemic stem cells. Cells and/or cell populations that can be manipulated by introduction of the CAR molecule, and preferably such cells made by the method of the present invention, are potentially unlimited, but comprise cell populations comprising T-central memory (TCM), effector memory T cells (TEM), natural killer cells (NK), and cytokine induced killer cells (CIK). CAR-mediated treatment employing such cells can represent a single therapeutic approach or can be combined with other approaches, before, at the same time or subsequently. The use of manipulated cells and/or cell populations of any source can be obtained post-transplant either in allogeneic or in autologous settings, particularly in lymphomatous pathologies, such as acute lymphoblastic leukemias, lymphomas and chronic lymphocytic leukemia (CLL). For anti-CD123 CAR, the main application is represented by acute myeloid leukemia and myelodysplasia, where the CD123 antigen is largely overexpressed in both the tumor mass and in the leukemic stem cell. Such approaches can be used post-transplant in allogeneic settings as prophylaxis or preemptive therapy, but also in autologous settings where the toxicity of a transplant procedure may overcome largely the benefits expected from the use of CAR expressed by donor-derived cell populations comprising T cells, or preferably cell populations comprising CIK cells (in specific categories, such as elderly patients not suitable for allogeneic transplantation). $CD123^{high}$ expressing plasmacytoid dendritic cells (pDC) have been described as playing a crucial role in the pathogenesis of various immuno-mediated diseases, such as viral infections and autoimmune disorders, and are involved in the immunological control of different tumors. An increase in numbers of pDC is observed in some inflammatory conditions, either infection-related, such as granulomatous lymphadenitis (tuberculosis, toxoplasmosis), or non-infection-related, such as sarcoidosis. Accumulation of pDC in lymph nodes has been observed also in epithelial neoplasms, lymphoproliferative and myeloproliferative diseases.

Among autoimmune diseases, pDC has been largely demonstrated to be involved in the immunopathogenesis of LES, mainly by IFN-α production. The selective elimination of pDC by autologous cell populations comprising T cells, and preferably cell populations comprising CIK cells, expressing anti-CD123 CAR is widely desirable in these settings, given their role in the pathogenesis of this disease.

The CAR-mediated treatment can be conceived as a single therapeutic approach or can be combined with other approaches before, at the same time or subsequently, in the context of "consolidative therapy." Behaving as long-lasting drugs, CAR-redirected immune cells of the present invention have the potential of controlling active diseases, preferably Minimal Residual Disease (MRD), in patients following initial chemotherapy or Hematopoietic Stem Cell Transplantation (HSCT), contrary to standard chemotherapy agents or monoclonal antibodies (mAbs), in patients who failed standard treatments.

Accordingly, another aspect of the present invention includes methods of administering the modified cells and/or cell populations comprising such cells of the present invention, or such cells and/or cell populations made by the method of the present invention, to a mammal in need thereof for the treatment or prevention of a disease or disorder in a mammal, preferably, a hematologic disorder or leukemia, a lymphoma, a solid tumor, a viral infection, an inflammatory disease or disorder, or an autoimmune disease or disorder. The ex vivo modified mononuclear cells and differentiated and/or expanded modified cells and/or cell populations comprising such cells can be administered to the subject by any number of approaches, preferably following lymphodepleting therapy and myeloablative chemotherapy. In a preferred embodiment, modified cells and/or cell populations comprising such cells are injected intravenously. The ex vivo modified mononuclear cells and differentiated and/or expanded modified cells and/or cell populations comprising such cells may also be introduced in a variety of pharmaceutical formulations comprising the cells and/or cell populations and normally employed additives as binders, fillers, carriers, preservatives, stabilizing agents, emulsifiers, and buffers. These may contain diluents and excipients, for example, water, saline, and dextrose. The patient may be optionally treated with agents to promote the in vivo function and persistence of the modified cells and/or cell populations comprising such cells. The ex vivo modified mononuclear cells and differentiated and/or expanded modified cells and/or cell populations comprising such cells may also be used in combination with chemotherapy or immunotherapy. The ex vivo modified mononuclear cells and differentiated and/or expanded modified cells and/or cell populations comprising such cells may also be administered to the subject, in a range approximately between about 0.1 and about $1 \times 10^7$ cells per kilogram (cells/kg). The infusion dose could vary from patient to patient depending on the patient's characteristics, type of disease and protocol design as determined by one skilled in the art. The infusion will be repeated as single or multiple doses depending on the achieved response and the patient tolerability to the treatment. Cells and/or cell populations can be administered prophylactically, pre-emptively or therapeutically. The administration may also occur when the disease is in the acute phase, but also in chronic phases and, in the context of an oncological disorder, in presence of bulky disease, at nadir stage and also in minimal residual disease conditions. The administration of ex vivo modified mononuclear cells and differentiated and/or expanded modified cells and/or cell populations to a subject before, during or after onset of the disease or disorder, may be necessary to diminish the frequency or severity of the signs or symptoms of the disease or disorder experienced by the subject.

EXPERIMENTAL EXAMPLES

The present invention is described in detail using the following experimental Examples of preferred embodiments and related drawings and Figures. These Examples are included with the purpose of illustrating the present invention without limiting the present invention in any way.

Example 1. SB-Mediated Genetic Manipulation of Primary T Cell Precursors with CD19.CAR and CD123.CAR to Induce CIK Cell Population Differentiation Following freshly isolated PBMC nucleofection in the presence of SB plasmids, according to the protocol reported on FIG. 1B, the inventors observed that DNA nucleofection causes significant loss of the CD11c⁺, myeloid dendritic cell (DC) and CD14⁺ monocytic cell populations and general cell mortality (FIG. 2A-C). The inventors also observed that the addition, 2 hours after nucleofection, of γ-irradiated autologous PBMC as accessory stimulating cells, restores the above mentioned loss of DC and monocytes. This action, with the concomitant stimulation by OKT3, rescued the impaired T cell expansion observed using nucleofector programs in association with plasmids SB (FIG. 2C-E). The 24 hour cell survival was (FIG. 2D-E) 52.6% (+/−6.3 n=13) for CD123.CAR (CIK-CAR123) and 45.0% (+/−8.4 n=7) for CD19.CAR (CIK-CAR19). Despite an initial cell modified growth delay comparing the No DNA control, both CD123.CAR and CD19.CAR cell populations expanded, without any additional stimulation, achieving within 3 weeks enough cell quantities and qualities sufficient for clinical uses (FIG. 3A). At the end of the differentiation process, cell vitality reached 80-90% for No DNA, CD123.CAR and CD19.CAR conditions (FIG. 4A-B). Such method minimally affected the phenotype of the CIK cell population final product (FIG. 3B).

Nucleofection average efficacy, measured as plasmid GFP expression after 24 hours, was 50.7% (+/−6.5 n=11) in CD123.CAR experiments and 42.0% (+/−4.0 n=4) in CD19.CAR experiments (FIG. 3C). The expression of CD123.CAR and CD19.CAR was stable in CIK cell populations and after 21 days reached a proportion of modified cells of 58.1% (+/−2.7% n=13) and 59.7% (+/−5.1% n=9) respectively (FIG. 3C-D). CAR molecules were stably expressed by each cell subpopulation as $CD3^+CD56^+$, $CD3^+CD8^+$, $CD3^+CD4^+$ cells and in all differentiation/memory stages (FIG. 4C).

This data shows that replacing stimulating cells impaired through the nucleofection with precursor PBMCs results in optimal stimulation by the concomitant addition of OKT3, leading in turn to a significant expansion of CARP CIK (CIK-CAR) cell populations. Efficient SB-mediated modification is achieved in the final cell product by limited manipulation without the need of purification, repetitive stimulation or selection by CAR-mediated engagement and/or propagation, which would allow for easy and efficient scale-up of related manufacturing processes.

Example 2. SB Mediated Engineering to Redirect the Effector Cell Activity of CD123 and CD19 CAR-Positive CIK Cell Populations Towards AML and ALL Cell Lines and Primary Blasts An efficient lysis of THP-1 AML cell line (85%+/−4.9) and AML primary blasts (60%+/−3.6) by CD123.CAR⁺ cells modified with SB and propagated as CIK cell populations according to the optimal stimulation protocol described in Example 1 has been shown. Similar results have been observed with CD19.CAR⁺ CIK cell populations (CIK-CAR19) towards REH ALL cell line (80.0%±6.0) and ALL primary blasts (56.8%+/−7.7) (FIG. 5A-B). CD123 and CD19 antigen expression on target cells has been confirmed via flow cytometry (Table).

When CD123.CAR⁺ CIK cell populations (CIK-CAR123) and CD19.CAR⁺ CIK cell populations (CIK-CAR123) were co-cultured with leukemic cell line and primary blasts, they showed specific cytotoxic degranulation tested by CD107a expression, in line with the lytic activity assessed by cytotoxic assays. In particular, cytotoxic degranulation has been associated with CAR expression, further indicating specific target recognition by the CAR and target cell killing by CAR⁺ CIK cell populations (FIG. 5C).

Moreover, CD123.CAR and CD19.CAR CIK cell populations stimulated with THP-1 cell line, AML primary cells and REH and ALL primary cells respectively, showed a significant higher IFN-γ and TNF-α cytokine release compared to No DNA CIK cell populations, as tested with ELISA and intracytoplasmic staining. (FIGS. 6A-C and 7A). The response was restricted to CAR⁺ CIK cell populations, indicating that cytokine secretion needs specific CAR triggering by the encounter with the antigen expressed by leukemic cells.

We then evaluated whether CD123.CAR and CD19.CAR constructs, which include a third generation signaling domain, lead to specific proliferation. CD123.CAR CIK cell populations proliferated in response to AML cells and CD19.CAR CIK cell populations proliferated in response to ALL cells, as determined by measurement of MTT cleaving ability and CFSE dilution assay (FIGS. 8 A-B). In particular, the proliferating $CSFE^{low}$ cells were also mainly CAR⁺, suggesting specific activation and selection of modified cells upon encounter with cancer cells (FIG. 8B).

Example 3. In Vivo Antitumor Response of CIK SB-Engineered Cells

In order to evaluate the in vivo efficacy of CD123.CAR and CD19.CAR CIK cells against AML and ALL, respectively, xenograft transplant models injecting KG-1 AML and NALM-6 ALL cell lines in the tail vein of immunodeficient NOD-SCID-γchain−/− (NSG) mice were used. Starting from day 14 after 5×10⁶ KG-1 xenograft, mice received an intravenous infusion of 10⁷ CD123.CAR CIK cell populations or No DNA control CIK cell populations from the same donor every 10 days, as previously reported (46) (FIG. 9A). At the time of sacrifice, KG-1 cells were engrafted either as disseminated leukemia or as extramedullary tumor in animals treated with No DNA cells. Conversely, treatment with CD123.CAR cells eradicated KG-1 cells in bone marrow and significantly inhibited tumor growth as compared to control No DNA cells (FIG. 9B-C). No extramedullary tumor has been found in mice treated with CD123.CAR cells. In the ALL model, NSG mice have been grafted with 1×10⁶ NALM-6 cells and subsequently infused with 10⁷ CD19.CAR CIK cell populations or No DNA CIK cell populations from the same donor on day 2 and 9 (FIG. 9D). A significant reduction of tumor growth in the CD19.CAR cell group compared to No DNA cell group has been observed (FIGS. 9 E-G).

Example 4. Safety and Efficacy Assessment in SB Marked CIK Cell Populations

In order to provide information on the safety and efficacy of SB-mediated gene therapy, we studied the genomic distribution of SB integration sites (IS) into the CIK cells genome. SB transposon/cellular genomic junctions were amplified by linear amplification-mediated (LAM) PCR on the genomic DNA of CD123.CAR CIK cell populations from 3 different healthy donors (HD). Spreadex gel electrophoresis of the LAM PCR products showed a smeared pattern (FIG. 10A), suggesting a polyclonal repertoire. PCR products were subjected to Illumina MiSeq next-generation sequencing and the integration sites mapped on the human genome using a previously described bioinformatics pipeline (48, 49). By this approach, we retrieved 1,239,800 integration sites, corresponding to 978 of unique IS (473, 212 and 293 in HD 1, 2, 3, respectively) (Table 2). Considering that each transposon integration site is as a unique genetic mark enabling to identify and track a cell clone and its progeny among a complex cell population of vector marked cells, the high number of integration sites retrieved further supports the polyclonal repertoire of the transduced CD123.CAR CIK cell populations. The overall distribution of SB integration sites, as previously reported by De Jong J. et al. (50) was randomly distributed along the genome, without preferences for gene dense regions and a low tendency to target gene promoters (FIG. 11A-B). Moreover, the canonical AT-rich conserved consensus at the genomic TA dinucleotides flanking the SB integration sites was found (T A T A/G T, FIG. 11C(51). The clonal abundance in the cultured modified CIK cell populations was estimated as the relative percentage of sequence counts representing each integration site with respect to the total of sequences retrieved in the analysis. No signs of vector-mediated dominance of individual clones emerged from this analysis (FIG. 11D and Table 3). Finally, we addressed if SB integrations targeting specific gene classes or genomic locations (Common Insertion Sites, CIS) were significantly enriched, suggesting a selective advantage conferred by this type of integrations. Gene ontology overrepresentation analysis, performed by GREAT online software (http://bejerano.stanford.edu/great/public/html/), indicated a significant enrichment of genes expressed in T cells (FIG. 11E) and in agreement with the known preference of SB transposons to integrate within expressed genes (50). CIS significance analysis was performed using Montecarlo simulations and considered only CIS constituted by at least 4 integration sites contained in a window of 100 Kb. By this approach no CIS were identified in this study (Table 4).

The SB11X transposase-expressing plasmid, although at low frequency, could integrate by chance into the host genome, express the SB11X transposase in the final cell product and potentially lead to remobilization of the SB transposon in other genomic positions. To evaluate the kinetic of SB11X transposase expression during CIK cell culture and thus guarantee the stability of the genomic content of the final cellular product after SB modification, we developed a quantitative RT-PCR assay specifically designed to detect SB transposase in transfected CIK cell populations. The slope of the standard curves was between −3.1 and −3.4 with a correlation coefficient >0.99 (FIG. 12A). The quantities of transposase were detected at day 1, 4, 7, 14, and 21 in CIK cell cultures from three different donors and normalized to $10^5$ GUS molecules (FIG. 12B). The number of transposase enzyme molecules was $10^7$ in each donor at day 1, consistent with the high nucleofection efficiency reported, but was gradually lost, turning out to be under the range of detection in the final cellular products (FIG. 12A-B).

Example 5. Comparison of CIK-Cell SB Transposon Platform Method with Existing Methods We next directly compared our platform method with the already established methods of conventional T cell stimulation and modification by SB (33, 60). Our data showed expansion of CIK cells at a higher rate compared to OKT3- and beads-activated T cells with a fold increase of 41±15.9 versus 13.8±3.2 and 9±3.7, respectively. Addition of γ-irradiated autologous PBMCs improved both OKT3- and beads-activated T cell expansion (FIG. 14A, B). CAR expression was similar in all conditions with the exception of the lower expressing beads-activated T cells (FIGS. 14 C, D). CIK cells were also superior in cytotoxicity (FIG. 14E, F) and cytokine secretion ability (FIG. 14G, H). The observed difference of CAR expression in beads-activated T cells and of cytotoxic activities in OKT3-activated T cells compared with CIK cells was restored by addition of γ-irradiated PBMCs.

Concerning CAR expression, achieved cell numbers and effector activities, we demonstrated improved efficacy of our method when directly compared to available existing SB methods applied to conventional T cells requiring repeated stimulations. Furthermore, similarly to CIK cells, conventional T cell expansion benefited from addition of irradiated PBMC.

Methods and Materials

Sleeping Beauty (SB)-mediated genetic manipulation of CD19.CAR and CD123.CAR is described as follows.

Cell Lines and Primary Cells

All cell lines were maintained in culture with Advanced RPMI medium (Invitrogen, Carlsbad, Calif., USA) supplemented with 10% heat-inactivated Fetal Bovine Serum (FBS), 2 mM L-glutamine, 25 IU/ml of penicillin and 25 mg/ml of streptomycin (Lonza, Basel, Switzerland). Primary AML and ALL cells were obtained from bone marrow and peripheral blood cells collected and frozen from eight leukemic children at diagnosis in the Ospedale San Gerardo. The Institutional Review Board approved this study and informed consent was obtained from patients or their guardians according to institutional guidelines and to the Helsinki Declaration.

Plasmids

The previously described high-affinity human scFv for CD123 (47) was generated starting from the DNA encoding mAb 7G3 (52) (kindly provided on behalf of CSL Research by Gino Vairo, CSL Limited Australia) was cloned in frame with $CH_2CH_3$-CD28-OX40-ζ from SFG-anti-CD33-CD28-OX40-ζ (kindly provided by Dr. Martin Pule, University College of London, London, UK) as a transposon into a SB expression plasmid, pT-MNDU3-eGFP (27) replacing the eGFP sequence to obtain anti-CD123/pTMNDU3. The anti-CD19/pTMNDU3 was generated replacing the scFvCD123 with the light chain (VL) and heavy chain (VH) from the SFG.aCD19 (clone FMC63 (45), kindly provided by Dr. Martin Pule). The codon-optimized DNA plasmids for SB transposase, pCMV-SB11, are described in FIG. 1A.

PBMCs Modification and Differentiation Towards CIK Cell Populations

Figure 1:
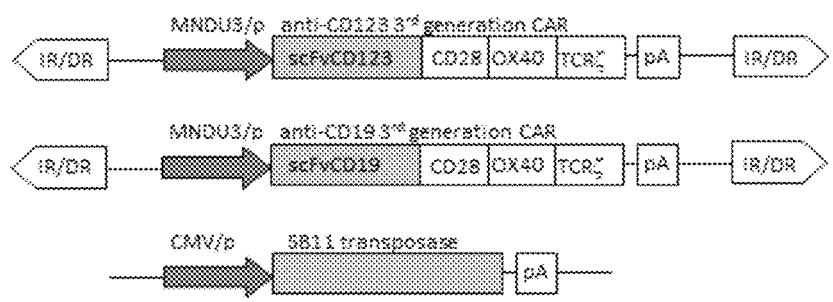
FIG. 1, including FIGS. 1A and B, illustrates the protocol for the modification and expansion of mononuclear precursors and for the generation of clinical-grade CIK-CAR cell populations starting from modified mononuclear cells expressing CD123.CAR and CD19.CAR through the non-viral Sleeping Beauty transposon. (A): Illustrates the scheme of the nucleic acids, Sleeping Beauty transposon and transposase, used in this study, encoding for CD123.CAR (higher panel), CD19.CAR (central panel), and the integrase transposase (lower panel) (IR/DR, inverted repeated SB sequences/MNDU3/p, the constitutive promoter of U3 region of the MND retrovirus, scFv, variable fragment of the single chain, pA, signal of polyadenylation of bovine growth hormone; CMV/p, CMV promoter). (B): Describes the protocol for modification and expansion used in this study. PBMCs from healthy donor (HD) were nucleofected on Day 0 (D0) with the nucleic acids transposon and transposase using the Amaxa Nucleofector™ method.
Figure 1:
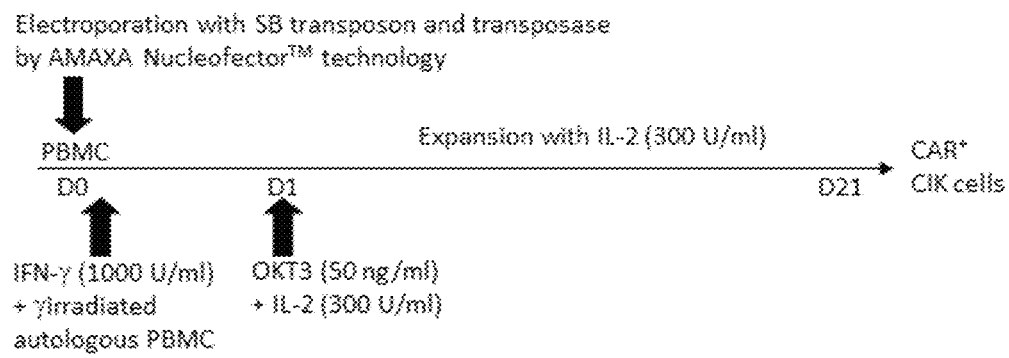

Human peripheral blood mononuclear cells (PBMCs) were obtained from healthy donors (HD) upon informed consent in accordance with local ethical committee approval and with the World Medical Association's Helsinki Declaration. PBMCs were isolated by centrifugation over Ficoll-Hypaque gradients (Pharmacia LKB, Uppsala, Sweden) and electroporated ($10^7$ cells per cuvette) by 4D-Nucleofector™ (Lonza) with 15 μg supercoiled DNA plasmid coding for anti-CD123 or, alternatively, anti-CD19 transposon (anti-CD123/pTMNDU3 or anti-CD19/pTMNDU3) and 5 μg supercoiled DNA pCMV-SB11 plasmid coding for SB11 using Amaxa™ 4D-Nucleofector™ high functionality EO-115 protocol for unstimulated human T cells (program 1) or EF-115 (program 2) and Amaxa™ P3 Primary Cell 4D-Nucleofector™ kit (Lonza). As positive control of modification at 24 h to assess functionality of nucleofection reaction, the Amaxa™ GFP plasmid was used. Cells were then re-suspended in Advanced RPMI medium (Invitrogen) supplemented with 20% heat-inactivated Fetal Calf Serum (FCS). After 2-3 hours on day 0, autologous PBMCs irradiated with 60 Gy of 137Cs γ-rays were added to the samples previously electroporated in the presence of DNA at a "irradiated PBMC:nucleofected PBMC" ratio of 1:2. The resulting cell population was differentiated towards CIK cell population by addition of IFN-γ (1000 U/ml; Dompè Biotec S.p.A, Milano, Italy) at day 0. IL-2 (300 U/ml; Chiron B. V, Emeryville, USA) and OKT-3 (50 ng/ml; Janssen-Cilag S.p.A., Cologno Monzese, Italy) were added at day 1 as previously described (53). Cells were then cultured for 21 days and fresh medium and IL-2 were added weekly during culture and cell concentration was maintained around $0.75 \times 10^6$ cells/ml (FIG. 1A-B).

Flow Cytometric Analysis

CIK-CAR cells were tested for the expression of CD3, CD8, CD4, CD56, CD62L and CD45RO (BD Bioscience, San Jose, Calif., USA), whereas leukemic blasts were tested using CD33, CD123, CD19, CD10 (BD Bioscience). For intracytoplasmic staining, CIK-CAR cells were stained with anti-CD3 mAb before fixation, permeabilization (Fixation/Permeabilization Solution Kit, BD Bioscience, San Diego, Calif., USA) and incubation with anti-human IFN-γ and IL-2 mAbs (BD Pharmingen, San Diego, Calif., USA). CAR expression has been detected with anti-Human IgG (H+L) specific antibody (Jackson ImmunoResearch, Suffolk, UK). Samples were acquired using a BD FACS Canto flow cytometer (BD Biosciences), and data were analyzed with FlowJo (Tree Star, Inc., Ashland, Oreg.). Quadrant markers were set accordingly to unstained controls.

Cytotoxic Assay

Cytotoxicity was evaluated in a 4-h co-culture assay at an Effector:Target (E:T) ratio of 5:1. Target viability was measured by apoptosis detection with GFP-Certified™ Apoptosis/Necrosis detection kit (Enzo Life Sciences, Inc., Farmingdale, N.Y., USA) staining, according to manufacture's protocols, gating on target cells previously labeled with 5-(and 6)-carboxyfluorescein diacetate succinimidyl ester, CFDA SE (CFSE, 1 µM, Bioscience, San Diego, Calif., USA). In brief, the final percentage of killed cells was determined as percentage of Annexin V$^+$Necrosis Detection Reagent (similar to 7-AAD)-plus Annexin V$^+$Necrosis Detection Reagent$^+$ in CSFE$^+$ target cells in co-culture with the effectors compared to target cells alone (42). Alternatively, flow cytometry-based quantitative analysis was used to enumerate the percentage of viable target cells recovered from culture, stained with PE-anti-CD33/CFSE for AML target or PE-anti-CD19 for ALL cells, as previously described. THP-1 target cell line was kindly provided by Dr. K. Fleischhauer, whereas REH was purchased from American Type Culture Collection (ATCC)

CD107a/GZB Mobilization Assay

CIK cell degranulation was evaluated in a CD107a flow cytometric assay, according to a protocol adapted from Alter et al. (54). Briefly, $10^5$ cells from CIK cell populations were plated with anti-CD107a FITC mAb (4 µL/well; BD Pharmingen), in 96-well round-bottom plates, in the presence or absence of $10^5$ cells of a target cell line or primary target cells at 37° C. After 3h, monensin A (Sigma-Aldrich, St Louis, Mo., USA) was added (30 µg/mL). After additional 3h of incubation, cells were washed and stained with anti-CD3, and anti-Human IgG (H+L) mAb.

Cytokine Detection $10^6$ cells/ml from CIK cell populations were stimulated with leukemic cell lines or primary blasts irradiated with 40Gy of 137Cs γ-rays (Effector:Stimulator (E:S) ratio 1:1). After 48 h, culture supernatants were harvested and levels of cytokines were determined by ELISA according to the manufacturer's instruction (R&D Systems, Minneapolis, USA). The limits of detection were 15.6 pg/ml.

Proliferation Assay $10^6$ cells/ml from CIK cell populations were stimulated with leukemic cell lines irradiated with 40Gy of 137Cs γ-rays (Effector:Stimulator (E:S) ratio 1:1). The ability of viable cells to cleave 3-(4,5-dimethylthiazol-2-yl)-2,5-diphenyltetrazolium bromide (MTT, Sigma-Aldrich) was measured as previously described (55, 56).

Alternatively, cell proliferation was tested by staining with 1 µM CFSE, as described elsewhere, by stimulation with leukemic cell lines irradiated with 40Gy of 137Cs γ-rays at 1:1 ratio. Cell division accompanied by CFSE dilution was analyzed by flow cytometry together with CAR expression and calculated by gating on CD3$^+$ cells.

Mice Model 7-9 week NOD-SCID-γchain-/- (NSG) mice (The Jackson laboratory, Bar Harbor, Me., USA) were transplanted with $5 \times 10^6$ KG-1 or $1 \times 10^6$ Nalm-6 cell lines using intravenous injection. Mice were then treated with $10 \times 10^6$ cells from CIK cell populations infused intravenously, as shown in the schematic representation of the xenograft experiments (FIGS. 9A and 9D). All experiments were performed on protocols approved by the Institutional Committees of Ministero della Salute and Università di Milano-Bicocca.

Quantitative Real-Time PCR Analysis for Absolute Detection of Transposase Enzyme Total RNA was extracted with RNeasy Mini kit (Qiagen, Hilden, Germany), and cDNA was synthesized with SuperScript II Reverse Transcriptase in the presence of RNase-OUT Ribonuclease Inhibitor (Life Technologies, Carlsbad, Calif.) according to manufacturer's instructions. Levels of transposase transcript were quantified using Universal Probe Library System (Roche Diagnostic GmbH, Mannheim, Germany) with FastStart Universal Probe Master (Roche). Optimal primers and probes for transposase amplification were selected using Roche ProbeFinder software at Assay Design Center (https://www.roche-applied-science.com). In order to set up the standard curve, the copy number per µl was estimated according to the molecular weight of the vector and the insert, as previously reported. Six successive dilutions (from $10^7$ to $10^1$) were prepared and used to calculate the standard curve. Real time analysis was performed using 7900HT Fast Real-Time PCR System platform (Life Technologies) with the following protocol: initial step at 95° C. for 10 min, then 50 cycles at 95° C. for 15 s and at 60° C. for 30 s using SDS2.3 software. The corresponding standard curve generated a mean slope of -3.24 and an intercept of 37.43 Ct (cycle threshold). Data were reported using a threshold of 0.1. A mean Ct value of 24.36 was obtained for the $10^4$ copies/ml dilution. cDNA samples (25 ng RNA equivalent) were run in duplicate or triplicate, and relative expression was determined by normalizing to GUS Control Gene Standards (Qiagen) expression in each set of samples to calculate a fold-change in value (standard curve with a mean slope of -3.38). The mean Ct value and the mean value of the log 10 of the copy number for GUS control gene were used for the statistical analysis.

Oligos and probes used in the experiments are listed as follows (Probe Sequence 5' to 3'):

Probe #87

Left primer AAGCCGAAGAACACCATCC (SEQ ID NO:1)

Right primer AGCACCCCCACAACATGA (SEQ ID NO:2)

SB Integration Site Retrieval and Analysis

Linear amplification-mediated PCR (LAM-PCR) was performed starting from 100 ng of genomic DNA from samples modified with the Sleeping Beauty (SB) system to collect integration sites, as previously described (57). Briefly, the LAM-PCR method start with two steps of linear amplification using a 5'-biotynilated primer designed in forward direction on right IRDR of the transposon under the following conditions: 95° C., for 5 min, 50 cycles at 95° C. for 1 min, 60° C. for 45 s, 72° C. for 90 s, and a final step at 72° C. for 10 min. After ligation o/n with streptavidin magnetic beads (Agencourt AMPure XP, Beckman Coulter Inc., Brea, Calif., USA) linear amplified products went through a hexanucleotide priming coupled to second-strand reconstitution, restriction enzyme digestion and ligation of a linker cassette. The biotinylated PCR product was denaturated, captured via magnetic beads, detached from beads and reamplified by two subsequent nested PCR with primers for right IRDR and linker cassette. We retrieved integration sites through the combination of LAM-PCR with the use of three restriction enzymes (HpyCH4IV, AciI and BfaI). We then adapted the LAM-PCR products for sequencing on an Illumina MiSeq sequencer using the Illumina Truseq DNA Sample Preparation Kit LT (Illumina Inc. San Diego, Calif., USA).

Oligos used in the experiments are listed as follows (5' to 3'):

```
Linear amplification 5'Biotin-
                                (SEQ ID NO: 3)
GCTTGTGGAAGGCTACTCGAAATGTTTGACCC 1st exponential PCR Forward transposon 1:
                                (SEQ ID NO: 4)
CCACTGGGAATGTGATGAAAGAAATAAAAGC Reverse Linker cassette 1:
                                (SEQ ID NO: 5)
GACCCGGGAGATCTGAATTC 2st exponential PCR Forward transposon 2:
                                (SEQ ID NO: 6)
AGACAGGGAATCTTTACTCGGA Reverse Linker cassette 2:
                                (SEQ ID NO: 7)
GATCTGAATTCAGTGGCACAG
```

Sequence reads obtained from Illumina MiSeq platform were processed and mapped on the human genome (Hg19) with a previously described bioinformatics pipeline (48, 49) adapted to recognize SB-transposon-cellular genomic junctions.

Clonal abundance was estimated as the relative percentage of the number of sequencing reads representing each integration site with respect to the total of sequencing reads obtained.

For each integration site the pipeline identified the nearest gene and the resulting gene list used for subsequent analysis. SB Integration site retrieval and analysis was kindly provided by the group of Dr Eugenio Montini.

TCR-V Rearrangement Using PCR Analysis

Total DNA has been extracted using QIAamp DNA Mini kit (Qiagen Hilden, Germany) according instructions. PCR amplification of the TCR-Vβ rearrangements on genetic DNA has been done using specific primers in two reactions which combine 23 Vβ primer and 13 Jβ primer, the first reaction with 23 primer Vβ and 9 primer Jβ which cover JB1.1-1.6, the second reaction with 23 primer Vβ and 4 primer Jβ which cover JB2.1 and JB2.3-5 (58). PCR products were run on electrophoresis gel (FIG. 13).

Conventional T Cell Differentiation and Modification

PBMCs were electroporated by 4D-Nucleofector™ (Lonza) with 15 μg supercoiled DNA transposon plasmid coding for CARs (anti-CD19/pTMNDU3) and 5 μg supercoiled DNA pCMV-SB11 plasmid using Amaxa™ 4D-Nucleofector™ EO-115 protocol and amaxa P3 Primary Cell 4D-Nucleofector kit (Lonza). OKT3- and beads-activated T cell lines were differentiated, as previously described (33, 60), with and without addition of irradiated PBMCs, according to our method. OKT3-activated cells were then cultured for 21 days. CD19.CAR OKT3-activated cells in the absence of irradiated PBMCs were then re-stimulated with a rapid expansion protocol until day 30, as previously described (33), since they expanded at lower extent compared to CIK cells. For the same reason, all beads-activated cell conditions were then re-stimulated with beads at day 14 until day 30, as previously described (60). Accordingly, subsequent analyses were performed on bulk CIK and OKT3-activated cells at day 21 and on CD19.CAR OKT3-activated cells in the absence of irradiated PBMCs and beads-activated cells at day 30.

Statistical Analysis

Mean values were reported as Mean±Standard Error (SE). Paired t-test and Mann Whitney test were used to determine the statistical significance of the data. Two-tailed paired analysis was performed, unless not specified in the text. Statistical calculations were performed with the Prism program 5.0 (GraphPad Software, Inc.).

TABLE 1

| | Age | Diagnosis | Subtype | % CD33+ | % CD123+ | Karyotype and Gene Mutations | Prognosis |
|---|---|---|---|---|---|---|---|
| | | | | patients' characteristics* | | | |
| UPN1 | 8 y | AML | M4 | 50.0 | 43.7 | 46, XX, inv(16)(p13q22)[16]/46, XX[4]; normal FLT3-ITD, normal NPM1a | SR |
| UPN2 | 13 y | AML | M2 | 86.0 | 71.3 | 46, XX, t(8; 21)(q22; q22)[20]; normal FLT3-ITD | SR |
| UPN3 | 4 y | AML | M5a | 86.0 | 95.5 | 47-48, XX, del(2)(p12), del(5)(p12), ?t(6; 7)(q21; q32), t(9; ?)(q34; ?), −11, del(12)(p11), +19, +4markers[cp9]/46, XX[3]; normal FLT3-ITD, normal NPM1a t(10; 11) positive by RT-PCR | HR |

TABLE 1-continued

| | | | | patients' characteristics* | | | |
|---|---|---|---|---|---|---|---|
| UPN4 | 16 y | AML | M2 | 85.0 | 56.6 | 45, XY, t(8; 21)(q22; q22)[6]/46, XY[6] | SR |
| UPN5 | 9 y | AML | M0 | 95.0 | 99.0 | 46, XX[9] normal FLT3-ITD, normal NPM1a | HR |
| UPN6 | 12 y | AML | M1 | 48.0 | 93.5 | 46, XY[25] NPM1+; FLT3 D835+ | SR |

| | Age | Diagnosis | Subtype | % CD10+ | % CD19+ | Karyotype and Gene Mutations | Prognosis |
|---|---|---|---|---|---|---|---|
| UPN7 | 8 y | ALL | BALL-IV | 90.6 | 91.0 | 46, XY, t(8; 14)(q24; q32)[20] | HR |
| UPN8 | 4 y | ALL | BALL-III | 96.4 | 22.3 | 47, XX, +21c[14] (Down) | HR |
| UPN9 | 8 m | ALL | BALL-I | 5.6 | 70.2 | 46, XY[14] | SR |

*Karyotype defined as International Standing Committee on Human Cytogenetic Nomenclature (ISCN) 2013, ITD = internal tandem duplication, HR = high risk, SR = standard risk, y = years, m = month, ALL subtype from classification EGIL(59), [ ] = number of metaphases analyzed

TABLE 2

| Chr | Integration locus | Integration strand | Gene symbol | Gene strand | Sequence count | % of reads |
|---|---|---|---|---|---|---|
| | | | Sample 12 | | | |
| 1 | 9504554 | − | SPSB1 | + | 50 | 0.01362 |
| 1 | 21858529 | − | ALPL | + | 768 | 0.20913 |
| 1 | 26725462 | + | LIN28A | + | 6305 | 1.71691 |
| 1 | 26725678 | − | LIN28A | + | 1 | 0.00027 |
| 1 | 29088451 | + | YTHDF2 | + | 518 | 0.14106 |
| 1 | 31506767 | − | PUM1 | − | 26 | 0.00708 |
| 1 | 32721009 | + | LCK | + | 995 | 0.27095 |
| 1 | 33098558 | + | ZBTB8OS | − | 13 | 0.00354 |
| 1 | 36937914 | + | CSF3R | − | 518 | 0.14106 |
| 1 | 38148152 | + | C1orf109 | − | 465 | 0.12662 |
| 1 | 39631435 | + | MACF1 | + | 1 | 0.00027 |
| 1 | 40014728 | + | PPIEL | − | 12 | 0.00327 |
| 1 | 44395464 | + | ST3GAL3 | + | 1302 | 0.35455 |
| 1 | 59589742 | + | HSD52 | − | 4 | 0.00109 |
| 1 | 62975332 | + | DOCK7 | − | 26 | 0.00708 |
| 1 | 78839706 | + | MGC27382 | + | 120 | 0.03268 |
| 1 | 81538454 | − | LPHN2 | + | 404 | 0.11001 |
| 1 | 86941142 | − | CLCA1 | + | 9 | 0.00245 |
| 1 | 87502306 | − | HS2ST1 | + | 4 | 0.00109 |
| 1 | 92361633 | + | TGFBR3 | − | 890 | 0.24235 |
| 1 | 93026597 | + | EVI5 | − | 14 | 0.00381 |
| 1 | 100795321 | + | CDC14A | + | 2121 | 0.57757 |
| 1 | 112096542 | − | ADORA3 | − | 362 | 0.09858 |
| 1 | 149312596 | + | LOC388692 | + | 1 | 0.00027 |
| 1 | 150125007 | − | PLEKHO1 | + | 62 | 0.01688 |
| 1 | 151153421 | − | VPS72 | − | 694 | 0.18898 |
| 1 | 151537034 | + | TUFT1 | + | 442 | 0.12036 |
| 1 | 161218954 | + | PCP4L1 | + | 1087 | 0.29600 |
| 1 | 161219109 | + | PCP4L1 | + | 1 | 0.00027 |
| 1 | 166784357 | − | POGK | + | 1795 | 0.48879 |
| 1 | 169363473 | − | C1orf114 | − | 10 | 0.00272 |
| 1 | 172995415 | − | TNFSF18 | − | 112 | 0.03050 |
| 1 | 174985823 | − | MRPS14 | − | 496 | 0.13507 |
| 1 | 178258605 | + | RASAL2 | + | 867 | 0.23609 |
| 1 | 182845293 | − | DHX9 | + | 761 | 0.20723 |
| 1 | 184072041 | + | TSEN15 | + | 821 | 0.22357 |
| 1 | 186924443 | + | PLA2G4A | + | 1 | 0.00027 |
| 1 | 200053746 | + | NR5A2 | + | 4 | 0.00109 |
| 1 | 201679597 | + | NAV1 | + | 2280 | 0.62086 |
| 1 | 207620326 | − | CR2 | + | 1608 | 0.43787 |
| 1 | 217583202 | + | GPATCH2 | − | 500 | 0.13615 |
| 1 | 221659980 | + | C1orf140 | − | 55 | 0.01498 |
| 1 | 222946901 | + | FAM177B | + | 592 | 0.16121 |
| 1 | 239701817 | + | CHRM3 | + | 325 | 0.08850 |
| 1 | 243713076 | − | AKT3 | − | 107 | 0.02914 |
| 2 | 11686694 | + | GREB1 | + | 86 | 0.02342 |
| 2 | 15434547 | − | NBAS | − | 1340 | 0.36489 |
| 2 | 15699434 | + | NBAS | − | 287 | 0.07815 |
| 2 | 26085373 | + | ASXL2 | − | 10244 | 2.78953 |
| 2 | 26328778 | + | RAB10 | + | 7 | 0.00191 |
| 2 | 27819908 | + | ZNF512 | + | 173 | 0.04711 |
| 2 | 28360579 | − | BRE | + | 47 | 0.01280 |
| 2 | 29441566 | + | ALK | − | 267 | 0.07271 |
| 2 | 30317700 | + | YPEL5 | + | 127 | 0.03458 |

TABLE 2-continued

| Chr | Integration locus | Integration strand | Gene symbol | Gene strand | Sequence count | % of reads |
|---|---|---|---|---|---|---|
| 2 | 30548555 | − | LBH | + | 682 | 0.18571 |
| 2 | 44743064 | + | MIR548AD | − | 2116 | 0.57621 |
| 2 | 45778056 | + | SRBD1 | − | 421 | 0.11464 |
| 2 | 54456879 | + | TSPYL6 | − | 498 | 0.13561 |
| 2 | 60347663 | + | MIR4432 | − | 1 | 0.00027 |
| 2 | 60347691 | − | MIR4432 | − | 282 | 0.07679 |
| 2 | 69635541 | + | NFU1 | − | 1 | 0.00027 |
| 2 | 71556329 | + | ZNF638 | + | 886 | 0.24127 |
| 2 | 74498711 | − | SLC4A5 | − | 19 | 0.00517 |
| 2 | 76238914 | − | GCFC2 | − | 926 | 0.25216 |
| 2 | 82780886 | − | LOC1720 | + | 17 | 0.00463 |
| 2 | 82784176 | − | LOC1720 | + | 327 | 0.08905 |
| 2 | 96818050 | + | DUSP2 | − | 4 | 0.00109 |
| 2 | 100002423 | − | EIF5B | + | 1 | 0.00027 |
| 2 | 102768613 | + | IL1R1 | + | 283 | 0.07706 |
| 2 | 102888011 | + | IL1RL2 | + | 117 | 0.03186 |
| 2 | 108871527 | − | SULT1C3 | + | 161 | 0.04384 |
| 2 | 162853947 | + | DPP4 | − | 816 | 0.22220 |
| 2 | 167825634 | − | XIRP2 | + | 833 | 0.22683 |
| 2 | 172151750 | − | METTL8 | − | 82 | 0.02233 |
| 2 | 174802802 | + | SP3 | − | 621 | 0.16910 |
| 2 | 180319564 | + | ZNF385B | − | 2851 | 0.77635 |
| 2 | 181943049 | − | UBE2E3 | + | 41 | 0.01116 |
| 2 | 191984508 | − | STAT4 | − | 1 | 0.00027 |
| 2 | 197072655 | − | HECW2 | − | 57 | 0.01552 |
| 2 | 197782744 | − | PGAP1 | − | 1490 | 0.40574 |
| 2 | 201261288 | − | SPATS2L | + | 603 | 0.16420 |
| 2 | 225770698 | + | DOCK10 | − | 295 | 0.08033 |
| 2 | 230898922 | + | SLC16A14 | − | 2 | 0.00054 |
| 2 | 231643688 | + | CAB39 | + | 153 | 0.04166 |
| 2 | 240608225 | − | LOC150935 | + | 571 | 0.15549 |
| 3 | 9763146 | + | CPNE9 | + | 219 | 0.05964 |
| 3 | 17487242 | + | TBC1D5 | − | 179 | 0.04874 |
| 3 | 17709817 | − | TBC1D5 | − | 31 | 0.00844 |
| 3 | 35468945 | + | ARPP21 | + | 837 | 0.22792 |
| 3 | 37286776 | − | GOLGA4 | + | 28 | 0.00762 |
| 3 | 38267043 | − | OXSR1 | + | 881 | 0.23990 |
| 3 | 38283964 | + | OXSR1 | + | 296 | 0.08060 |
| 3 | 46347477 | − | CCR3 | + | 25 | 0.00681 |
| 3 | 47500937 | + | SCAP | − | 84 | 0.02287 |
| 3 | 50622378 | − | HEMK1 | + | 4291 | 1.16848 |
| 3 | 51964071 | − | RRP9 | − | 7090 | 1.93067 |
| 3 | 66345482 | − | SLC25A26 | + | 1 | 0.00027 |
| 3 | 66345606 | − | SLC25A26 | + | 7854 | 2.13871 |
| 3 | 72489140 | + | RYBP | − | 37 | 0.01008 |
| 3 | 99639304 | − | FILIP1L | − | 203 | 0.05528 |
| 3 | 108152827 | − | MYH15 | − | 3 | 0.00082 |
| 3 | 115464212 | − | GAP43 | + | 2967 | 0.80794 |
| 3 | 115915208 | + | LSAMP | − | 498 | 0.13561 |
| 3 | 119641863 | − | GSK3B | − | 404 | 0.11001 |
| 3 | 122985841 | + | SEC22A | + | 133 | 0.03622 |
| 3 | 126743681 | + | PLXNA1 | + | 1 | 0.00027 |
| 3 | 127924873 | + | EEFSEC | + | 980 | 0.26686 |
| 3 | 127924902 | + | EEFSEC | + | 1 | 0.00027 |
| 3 | 129549646 | + | TMCC1 | − | 16 | 0.00436 |
| 3 | 132565292 | + | NPHP3-AS1 | + | 36 | 0.00980 |
| 3 | 137953935 | − | ARMC8 | + | 43 | 0.01171 |
| 3 | 142637938 | + | LOC100507389 | + | 3 | 0.00082 |
| 3 | 156747336 | + | LEKR1 | + | 1 | 0.00027 |
| 3 | 163177677 | − | LOC647107 | − | 1 | 0.00027 |
| 3 | 170568509 | + | RPL22L1 | − | 166 | 0.04520 |
| 3 | 184575664 | − | VPS8 | + | 243 | 0.06617 |
| 3 | 195747743 | + | TFRC | − | 8 | 0.00218 |
| 4 | 25379636 | − | ANAPC4 | + | 275 | 0.07488 |
| 4 | 48834708 | + | OCIAD1 | + | 1167 | 0.31778 |
| 4 | 53805492 | − | SCFD2 | − | 261 | 0.07107 |
| 4 | 54727799 | + | RPL21P44 | − | 2610 | 0.71073 |
| 4 | 57820422 | − | NOA1 | − | 28 | 0.00762 |
| 4 | 61814084 | − | LPHN3 | + | 235 | 0.06399 |
| 4 | 64941872 | + | TECRL | − | 488 | 0.13289 |
| 4 | 67293250 | + | LOC100144602 | + | 2 | 0.00054 |
| 4 | 70610572 | − | SULT1B1 | − | 149 | 0.04057 |
| 4 | 91170815 | − | FAM190A | + | 159 | 0.04330 |
| 4 | 99056323 | − | C4orf37 | − | 60 | 0.01634 |
| 4 | 140204131 | − | C4orf49 | − | 371 | 0.10103 |
| 4 | 146792342 | + | ZNF827 | − | 105 | 0.02859 |
| 4 | 154663769 | − | RNF175 | − | 395 | 0.10756 |

TABLE 2-continued

| Chr | Integration locus | Integration strand | Gene symbol | Gene strand | Sequence count | % of reads |
|---|---|---|---|---|---|---|
| 4 | 162479178 | + | FSTL5 | − | 30 | 0.00817 |
| 4 | 169323031 | − | DDX60L | − | 2 | 0.00054 |
| 4 | 174075410 | − | GALNT7 | + | 2 | 0.00054 |
| 4 | 175784727 | + | GLRA3 | − | 655 | 0.17836 |
| 4 | 179879014 | + | LOC285501 | + | 1 | 0.00027 |
| 5 | 6379268 | + | MED10 | − | 1 | 0.00027 |
| 5 | 6379334 | − | MED10 | − | 4579 | 1.24690 |
| 5 | 6569554 | − | LOC255167 | + | 10 | 0.00272 |
| 5 | 21844511 | + | CDH12 | − | 144 | 0.03921 |
| 5 | 39643745 | − | DAB2 | − | 110 | 0.02995 |
| 5 | 55034831 | − | DDX4 | + | 31 | 0.00844 |
| 5 | 61652440 | + | KIF2A | + | 1668 | 0.45421 |
| 5 | 63169724 | − | HTR1A | − | 1106 | 0.30117 |
| 5 | 77400377 | + | AP3B1 | − | 1824 | 0.49669 |
| 5 | 79508954 | − | SERINC5 | − | 1 | 0.00027 |
| 5 | 79509134 | − | SERINC5 | − | 45 | 0.01225 |
| 5 | 92813273 | + | FLJ42709 | − | 683 | 0.18599 |
| 5 | 95506170 | + | MIR583 | + | 3270 | 0.89045 |
| 5 | 130222213 | − | HINT1 | − | 10 | 0.00272 |
| 5 | 130755619 | + | RAPGEF6 | − | 2045 | 0.55687 |
| 5 | 148607465 | − | ABLIM3 | + | 15 | 0.00408 |
| 5 | 149728627 | − | TCOF1 | + | 1 | 0.00027 |
| 5 | 156640064 | − | ITK | + | 88 | 0.02396 |
| 5 | 157255491 | + | CLINT1 | − | 362 | 0.09858 |
| 5 | 157406052 | + | CLINT1 | − | 16 | 0.00436 |
| 5 | 164222210 | − | MAT2B | + | 180 | 0.04902 |
| 5 | 169285150 | + | FAM196B | − | 587 | 0.15985 |
| 5 | 179951870 | + | CNOT6 | + | 563 | 0.15331 |
| 5 | 179951907 | + | CNOT6 | + | 1 | 0.00027 |
| 6 | 9146475 | + | LOC100506207 | + | 1 | 0.00027 |
| 6 | 21641423 | + | LINC00340 | + | 38 | 0.01035 |
| 6 | 25752428 | + | SLC17A4 | + | 406 | 0.11056 |
| 6 | 31218134 | − | HLA-C | − | 1164 | 0.31697 |
| 6 | 35585597 | + | FKBP5 | − | 2085 | 0.56776 |
| 6 | 38864462 | + | DNAH8 | + | 500 | 0.13615 |
| 6 | 40749983 | + | LRFN2 | − | 309 | 0.08414 |
| 6 | 42001202 | − | CCND3 | − | 2 | 0.00054 |
| 6 | 55822900 | − | BMP5 | − | 452 | 0.12308 |
| 6 | 57992706 | − | GUSBP4 | − | 132 | 0.03594 |
| 6 | 65862730 | − | EYS | − | 2 | 0.00054 |
| 6 | 75547358 | − | COL12A1 | − | 248 | 0.06753 |
| 6 | 81706824 | + | BCKDHB | + | 304 | 0.08278 |
| 6 | 96759697 | − | FUT9 | + | 2 | 0.00054 |
| 6 | 107071202 | + | RTN4IP1 | − | 2 | 0.00054 |
| 6 | 108868871 | − | FOXO3 | + | 321 | 0.08741 |
| 6 | 120366208 | − | LOC285762 | − | 962 | 0.26196 |
| 6 | 126164319 | − | NCOA7 | + | 267 | 0.07271 |
| 6 | 139449363 | − | HECA | + | 1 | 0.00027 |
| 6 | 139449493 | − | HECA | + | 8110 | 2.20843 |
| 6 | 143195681 | + | HIVEP2 | − | 168 | 0.04575 |
| 6 | 154054018 | + | OPRM1 | + | 799 | 0.21757 |
| 6 | 158518109 | + | SYNJ2 | + | 89 | 0.02424 |
| 7 | 1572637 | + | MAFK | + | 2037 | 0.55469 |
| 7 | 16980158 | + | AGR3 | − | 181 | 0.04929 |
| 7 | 50115718 | − | ZPBP | − | 1024 | 0.27884 |
| 7 | 50297862 | + | IKZF1 | + | 127 | 0.03458 |
| 7 | 50333086 | − | IKZF1 | + | 32 | 0.00871 |
| 7 | 71433022 | + | CALN1 | − | 852 | 0.23201 |
| 7 | 75293460 | − | HIP1 | − | 1767 | 0.48117 |
| 7 | 77371133 | − | RSBN1L | + | 126 | 0.03431 |
| 7 | 85253446 | − | SEMA3D | − | 7 | 0.00191 |
| 7 | 85407759 | − | SEMA3D | − | 336 | 0.09150 |
| 7 | 100840533 | − | MOGAT3 | − | 1 | 0.00027 |
| 7 | 105725968 | + | SYPL1 | − | 733 | 0.19960 |
| 7 | 112344803 | + | TMEM168 | − | 15 | 0.00408 |
| 7 | 112735161 | + | GPR85 | − | 473 | 0.12880 |
| 7 | 127376637 | − | SND1 | + | 1 | 0.00027 |
| 7 | 130447290 | + | KLF14 | − | 447 | 0.12172 |
| 7 | 133949613 | − | LRGUK | + | 131 | 0.03567 |
| 7 | 149455956 | − | ZNF467 | − | 142 | 0.03867 |
| 7 | 151161680 | + | RHEB | − | 316 | 0.08605 |
| 8 | 2108833 | + | MYOM2 | + | 406 | 0.11056 |
| 8 | 5720949 | + | LOC100287015 | − | 256 | 0.06971 |
| 8 | 12878500 | − | KIAA1456 | + | 297 | 0.08088 |
| 8 | 28225470 | + | ZNF395 | − | 152 | 0.04139 |
| 8 | 62113124 | + | CLVS1 | + | 464 | 0.12635 |
| 8 | 68372089 | − | CPA6 | − | 341 | 0.09286 |

TABLE 2-continued

| Chr | Integration locus | Integration strand | Gene symbol | Gene strand | Sequence count | % of reads |
|---|---|---|---|---|---|---|
| 8 | 70764527 | − | SLCO5A1 | − | 482 | 0.13125 |
| 8 | 80558484 | + | STMN2 | + | 22 | 0.00599 |
| 8 | 86184831 | + | CA13 | + | 1415 | 0.38532 |
| 8 | 87169990 | − | ATP6V0D2 | + | 6 | 0.00163 |
| 8 | 128067552 | + | PCAT1 | + | 32 | 0.00871 |
| 8 | 129976078 | + | LOC728724 | − | 299 | 0.08142 |
| 8 | 132867412 | + | EFR3A | + | 66 | 0.01797 |
| 8 | 134143736 | − | TG | + | 2 | 0.00054 |
| 8 | 143796453 | − | LOC100288181 | − | 63 | 0.01716 |
| 9 | 5212811 | + | INSL4 | + | 1 | 0.00027 |
| 9 | 31260458 | − | LOC401497 | − | 35 | 0.00953 |
| 9 | 79277908 | − | PRUNE2 | − | 18 | 0.00490 |
| 9 | 89786537 | − | C9orf170 | + | 610 | 0.16611 |
| 9 | 96177945 | + | FAM120AOS | − | 7 | 0.00191 |
| 9 | 99026987 | − | HSD17B3 | − | 11 | 0.00300 |
| 9 | 114163915 | + | KIAA0368 | − | 21 | 0.00572 |
| 9 | 114555037 | + | C9orf84 | − | 113 | 0.03077 |
| 9 | 115028050 | − | PTBP3 | − | 2060 | 0.56096 |
| 9 | 115097155 | + | PTBP3 | − | 9 | 0.00245 |
| 9 | 115338530 | − | KIAA1958 | + | 205 | 0.05582 |
| 9 | 116188612 | − | C9orf43 | + | 557 | 0.15168 |
| 9 | 121224378 | − | DBC1 | − | 140 | 0.03812 |
| 9 | 126284999 | + | DENND1A | − | 1174 | 0.31969 |
| 9 | 129593603 | + | ZBTB43 | + | 91 | 0.02478 |
| 9 | 131242489 | − | ODF2 | + | 4136 | 1.12627 |
| 9 | 133578827 | + | EXOSC2 | + | 298 | 0.08115 |
| 9 | 136965839 | + | BRD3 | − | 7102 | 1.93394 |
| 10 | 14071668 | + | FRMD4A | − | 649 | 0.17673 |
| 10 | 16699302 | + | RSU1 | − | 950 | 0.25869 |
| 10 | 19025291 | + | ARL5B | + | 246 | 0.06699 |
| 10 | 22202076 | − | DNAJC1 | − | 2010 | 0.54734 |
| 10 | 34144025 | − | LOC100505583 | − | 467 | 0.12717 |
| 10 | 52905179 | + | PRKG1 | + | 8931 | 2.43199 |
| 10 | 54277526 | − | DKK1 | + | 302 | 0.08224 |
| 10 | 73837933 | − | SPOCK2 | − | 57 | 0.01552 |
| 10 | 73967866 | + | ASCC1 | − | 28 | 0.00762 |
| 10 | 78892584 | − | KCNMA1 | − | 18 | 0.00490 |
| 10 | 83255648 | + | NRG3 | + | 1880 | 0.51194 |
| 10 | 84715539 | − | NRG3 | + | 110 | 0.02995 |
| 10 | 85934808 | + | C10orf99 | + | 1168 | 0.31806 |
| 10 | 90616020 | − | ANKRD22 | − | 447 | 0.12172 |
| 10 | 90850452 | + | MIR4679-2 | − | 43 | 0.01171 |
| 10 | 91224573 | + | SLC16A12 | − | 1021 | 0.27803 |
| 10 | 101516210 | + | CUTC | + | 852 | 0.23201 |
| 10 | 102130548 | − | LINC00263 | + | 83 | 0.02260 |
| 10 | 103349698 | − | DPCD | + | 7 | 0.00191 |
| 10 | 104333377 | − | SUFU | + | 241 | 0.06563 |
| 10 | 114464138 | − | VTI1A | + | 27 | 0.00735 |
| 10 | 120448820 | + | C10orf46 | − | 430 | 0.11709 |
| 10 | 128478021 | − | DOCK1 | + | 37 | 0.01008 |
| 10 | 135337025 | − | CYP2E1 | + | 1272 | 0.34638 |
| 11 | 515872 | + | RNH1 | − | 209 | 0.05691 |
| 11 | 5538486 | − | UBQLNL | − | 550 | 0.14977 |
| 11 | 9931734 | − | SBF2 | − | 18 | 0.00490 |
| 11 | 22437542 | + | SLC17A6 | + | 612 | 0.16665 |
| 11 | 34097384 | − | CAPRIN1 | + | 731 | 0.19906 |
| 11 | 44140682 | − | EXT2 | − | 244 | 0.06644 |
| 11 | 45182072 | − | PRDM11 | + | 316 | 0.08605 |
| 11 | 54944827 | + | TRIM48 | + | 2841 | 0.77363 |
| 11 | 58017821 | + | OR10W1 | − | 465 | 0.12662 |
| 11 | 59405406 | − | PATL1 | − | 1474 | 0.40138 |
| 11 | 63288930 | − | LGALS12 | + | 22 | 0.00599 |
| 11 | 75618877 | − | UVRAG | + | 468 | 0.12744 |
| 11 | 86054046 | + | C11orf73 | + | 244 | 0.06644 |
| 11 | 88075620 | + | CTSC | − | 1 | 0.00027 |
| 11 | 93821181 | + | HEPHL1 | + | 567 | 0.15440 |
| 11 | 95683279 | + | MTMR2 | − | 305 | 0.08305 |
| 11 | 95864700 | − | MAML2 | − | 468 | 0.12744 |
| 11 | 95938154 | − | MAML2 | − | 467 | 0.12717 |
| 11 | 101040981 | − | PGR | + | 4 | 0.00109 |
| 11 | 102247941 | + | BIRC2 | + | 1258 | 0.34256 |
| 11 | 107586788 | + | SLN | − | 287 | 0.07815 |
| 11 | 108206559 | − | ATM | + | 125 | 0.03404 |
| 11 | 108218989 | − | ATM | + | 7 | 0.00191 |
| 11 | 109954311 | + | ZC3H12C | + | 1 | 0.00027 |
| 11 | 110096201 | − | RDX | − | 1 | 0.00027 |
| 11 | 118053057 | + | SCN2B | − | 104 | 0.02832 |

TABLE 2-continued

| Chr | Integration locus | Integration strand | Gene symbol | Gene strand | Sequence count | % of reads |
|---|---|---|---|---|---|---|
| 11 | 118136203 | + | MPZL2 | − | 171 | 0.04656 |
| 11 | 118649272 | + | DDX6 | − | 1700 | 0.46293 |
| 11 | 122686007 | + | UBASH3B | + | 1530 | 0.41663 |
| 11 | 125475290 | − | STT3A | + | 565 | 0.15385 |
| 11 | 128081151 | − | ETS1 | − | 544 | 0.14814 |
| 11 | 134568500 | + | LOC283177 | + | 75 | 0.02042 |
| 12 | 443992 | + | KDM5A | − | 1413 | 0.38477 |
| 12 | 721281 | + | NINJ2 | − | 1 | 0.00027 |
| 12 | 7604863 | − | CD163L1 | − | 1 | 0.00027 |
| 12 | 10537149 | − | KLRK1 | − | 249 | 0.06780 |
| 12 | 10543107 | − | KLRK1 | − | 103 | 0.02805 |
| 12 | 13305767 | + | EMP1 | + | 196 | 0.05337 |
| 12 | 19276578 | + | PLEKHA5 | + | 1267 | 0.34502 |
| 12 | 25803891 | + | IFLTD1 | − | 3030 | 0.82510 |
| 12 | 47610163 | + | FAM113B | + | 7 | 0.00191 |
| 12 | 49652946 | − | TUBA1C | + | 2 | 0.00054 |
| 12 | 50142339 | + | TMBIM6 | + | 93 | 0.02532 |
| 12 | 50170530 | + | TMBIM6 | + | 116 | 0.03159 |
| 12 | 53595267 | + | ITGB7 | − | 3 | 0.00082 |
| 12 | 54880812 | − | NCKAP1L | + | 37 | 0.01008 |
| 12 | 57020257 | + | BAZ2A | − | 5 | 0.00136 |
| 12 | 60045658 | − | SLC16A7 | + | 405 | 0.11029 |
| 12 | 70690362 | − | CNOT2 | + | 7 | 0.00191 |
| 12 | 70820222 | + | KCNMB4 | + | 23 | 0.00626 |
| 12 | 77123860 | + | ZDHHC17 | + | 1094 | 0.29791 |
| 12 | 85612225 | + | LRRIQ1 | + | 283 | 0.07706 |
| 12 | 91795313 | + | DCN | − | 79 | 0.02151 |
| 12 | 99433725 | − | ANKS1B | − | 19 | 0.00517 |
| 12 | 104678265 | + | TXNRD1 | + | 394 | 0.10729 |
| 12 | 110738780 | − | ATP2A2 | + | 2231 | 0.60752 |
| 12 | 123522760 | + | PITPNM2 | − | 776 | 0.21131 |
| 13 | 22004222 | + | ZDHHC20 | − | 328 | 0.08932 |
| 13 | 30942321 | − | LINC00426 | − | 1559 | 0.42453 |
| 13 | 34222559 | − | STARD13 | − | 309 | 0.08414 |
| 13 | 42165576 | + | KIAA0564 | − | 292 | 0.07951 |
| 13 | 43594683 | − | DNAJC15 | + | 451 | 0.12281 |
| 13 | 45089285 | − | TSC22D1 | − | 327 | 0.08905 |
| 13 | 46339133 | − | SIAH3 | − | 314 | 0.08550 |
| 13 | 64270046 | − | OR7E156P | + | 661 | 0.18000 |
| 13 | 77382646 | + | KCTD12 | − | 28 | 0.00762 |
| 13 | 90915917 | + | MIR622 | + | 17062 | 4.64613 |
| 13 | 99999183 | + | FKSG29 | + | 72 | 0.01961 |
| 13 | 101392113 | + | TMTC4 | − | 636 | 0.17319 |
| 13 | 113871835 | − | CUL4A | + | 360 | 0.09803 |
| 14 | 20538241 | + | OR4L1 | + | 8 | 0.00218 |
| 14 | 25025521 | − | CTSG | − | 1804 | 0.49125 |
| 14 | 33843865 | − | NPAS3 | + | 436 | 0.11873 |
| 14 | 50173304 | − | KLHDC1 | + | 98 | 0.02669 |
| 14 | 50351080 | − | ARF6 | + | 94 | 0.02560 |
| 14 | 54886814 | + | CDKN3 | + | 5 | 0.00136 |
| 14 | 56020400 | + | KTN1-AS1 | − | 2 | 0.00054 |
| 14 | 56620913 | − | PELI2 | + | 238 | 0.06481 |
| 14 | 62205149 | + | HIF1A | + | 41 | 0.01116 |
| 14 | 67818897 | + | ATP6V1D | − | 193 | 0.05256 |
| 14 | 69915531 | − | SLC39A9 | + | 6 | 0.00163 |
| 14 | 74216887 | − | MIR4505 | + | 721 | 0.19633 |
| 14 | 75954964 | − | JDP2 | + | 1 | 0.00027 |
| 14 | 98832194 | + | C14orf177 | + | 9 | 0.00245 |
| 14 | 104119634 | + | KLC1 | + | 300 | 0.08169 |
| 14 | 104429595 | + | TDRD9 | + | 859 | 0.23391 |
| 15 | 20019165 | + | CHEK2P2 | + | 576 | 0.15685 |
| 15 | 20019605 | − | CHEK2P2 | + | 1 | 0.00027 |
| 15 | 34444860 | + | C15orf29 | − | 331 | 0.09013 |
| 15 | 43712986 | + | TP53BP1 | − | 4247 | 1.15650 |
| 15 | 45135866 | − | TRIM69 | + | 1 | 0.00027 |
| 15 | 50983220 | + | TRPM7 | − | 961 | 0.26169 |
| 15 | 55125467 | − | UNC13C | + | 91 | 0.02478 |
| 15 | 60866543 | − | RORA | − | 4468 | 1.21668 |
| 15 | 65597300 | + | PARP16 | − | 49 | 0.01334 |
| 15 | 71270754 | − | LRRC49 | + | 43 | 0.01171 |
| 15 | 75007388 | − | CYP1A1 | − | 1 | 0.00027 |
| 15 | 75007421 | − | CYP1A1 | − | 736 | 0.20042 |
| 15 | 76909801 | − | SCAPER | − | 1 | 0.00027 |
| 15 | 78512501 | + | ACSBG1 | − | 2519 | 0.68595 |
| 15 | 91209413 | − | CRTC3 | + | 2197 | 0.59826 |
| 16 | 3373755 | − | ZNF75A | + | 1 | 0.00027 |
| 16 | 3768330 | + | TRAP1 | − | 3683 | 1.00291 |

TABLE 2-continued

| Chr | Integration locus | Integration strand | Gene symbol | Gene strand | Sequence count | % of reads |
|---|---|---|---|---|---|---|
| 16 | 7043897 | + | RBFOX1 | - | 306 | 0.08333 |
| 16 | 8766774 | - | ABAT | + | 188 | 0.05119 |
| 16 | 9176976 | + | C16orf72 | + | 448 | 0.12199 |
| 16 | 11646328 | + | LITAF | - | 160 | 0.04357 |
| 16 | 11839652 | + | TXNDC11 | - | 445 | 0.12118 |
| 16 | 21711471 | - | OTOA | + | 4119 | 1.12164 |
| 16 | 28302771 | + | SBK1 | + | 54 | 0.01470 |
| 16 | 50094205 | + | HEATR3 | + | 726 | 0.19770 |
| 16 | 50094294 | - | HEATR3 | + | 1 | 0.00027 |
| 16 | 53770854 | + | FTO | + | 394 | 0.10729 |
| 16 | 58597838 | - | CNOT1 | - | 497 | 0.13534 |
| 16 | 68255335 | + | NFATC3 | + | 28 | 0.00762 |
| 16 | 69160515 | - | CHTF8 | - | 177 | 0.04820 |
| 16 | 69914046 | + | WWP2 | + | 6 | 0.00163 |
| 16 | 72970272 | - | ZFHX3 | - | 25 | 0.00681 |
| 16 | 73333032 | + | LOC100506172 | + | 196 | 0.05337 |
| 17 | 7467347 | + | SENP3-EIF4A1 | + | 182 | 0.04956 |
| 17 | 8875222 | + | PIK3R5 | - | 1 | 0.00027 |
| 17 | 13192214 | - | HS3ST3A1 | - | 2 | 0.00054 |
| 17 | 14088125 | - | COX10 | + | 4 | 0.00109 |
| 17 | 15484995 | - | CDRT1 | - | 1401 | 0.38150 |
| 17 | 18668500 | - | FBXW10 | + | 6 | 0.00163 |
| 17 | 19849526 | - | AKAP10 | - | 27 | 0.00735 |
| 17 | 26410441 | + | NLK | + | 10 | 0.00272 |
| 17 | 33195806 | - | CCT6B | - | 320 | 0.08714 |
| 17 | 37963506 | + | IKZF3 | - | 290 | 0.07897 |
| 17 | 38223212 | - | THRA | + | 47 | 0.01280 |
| 17 | 38709048 | + | CCR7 | - | 615 | 0.16747 |
| 17 | 40616902 | - | ATP6V0A1 | + | 40 | 0.01089 |
| 17 | 45848525 | + | TBX21 | + | 4539 | 1.23601 |
| 17 | 50127399 | - | CA10 | - | 179 | 0.04874 |
| 17 | 57513988 | - | YPEL2 | + | 7 | 0.00191 |
| 17 | 57860815 | + | VMP1 | + | 496 | 0.13507 |
| 17 | 60238464 | - | MED13 | - | 320 | 0.08714 |
| 17 | 62566017 | - | SMURF2 | - | 216 | 0.05882 |
| 17 | 62674317 | + | SMURF2 | - | 378 | 0.10293 |
| 17 | 62674338 | + | SMURF2 | - | 1 | 0.00027 |
| 17 | 62674352 | + | SMURF2 | - | 1 | 0.00027 |
| 17 | 67082640 | - | ABCA6 | - | 1 | 0.00027 |
| 17 | 69286553 | + | SOX9 | + | 9319 | 2.53765 |
| 17 | 73340158 | - | GRB2 | - | 649 | 0.17673 |
| 17 | 76159367 | - | C17orf99 | + | 3739 | 1.01816 |
| 17 | 78488511 | - | RPTOR | + | 45 | 0.01225 |
| 17 | 78737761 | - | RPTOR | + | 1 | 0.00027 |
| 18 | 3093459 | + | MYOM1 | - | 136 | 0.03703 |
| 18 | 4470661 | - | DLGAP1 | - | 1447 | 0.39403 |
| 18 | 32914444 | + | ZNF24 | - | 4 | 0.00109 |
| 18 | 38372096 | - | KC6 | - | 1 | 0.00027 |
| 18 | 47334759 | + | ACAA2 | - | 3 | 0.00082 |
| 18 | 50041623 | - | DCC | + | 2100 | 0.57185 |
| 18 | 54009119 | + | LOC100505474 | - | 889 | 0.24208 |
| 18 | 55340267 | + | ATP8B1 | - | 1569 | 0.42725 |
| 18 | 57633332 | - | PMAIP1 | + | 212 | 0.05773 |
| 18 | 57879272 | - | MC4R | - | 3 | 0.00082 |
| 18 | 59017848 | - | CDH20 | + | 154 | 0.04194 |
| 18 | 60887826 | + | BCL2 | - | 348 | 0.09476 |
| 18 | 72627053 | + | ZNF407 | + | 4874 | 1.32723 |
| 19 | 2098509 | + | IZUMO4 | + | 1 | 0.00027 |
| 19 | 3334362 | - | NFIC | + | 5 | 0.00136 |
| 19 | 9818647 | + | ZNF812 | - | 132 | 0.03594 |
| 19 | 12173541 | + | ZNF844 | + | 55 | 0.01498 |
| 19 | 14637307 | - | MIR639 | + | 17 | 0.00463 |
| 19 | 15119295 | + | CCDC105 | + | 1 | 0.00027 |
| 19 | 15119470 | - | CCDC105 | + | 1207 | 0.32868 |
| 19 | 15821851 | + | CYP4F12 | - | 1463 | 0.39839 |
| 19 | 16273638 | + | CIB3 | - | 78 | 0.02124 |
| 19 | 21835599 | + | ZNF100 | - | 206 | 0.05610 |
| 19 | 21835663 | + | ZNF100 | - | 1 | 0.00027 |
| 19 | 42422365 | - | ARHGEF1 | + | 803 | 0.21866 |
| 19 | 42481899 | + | ATP1A3 | - | 8757 | 2.38461 |
| 19 | 43018058 | - | CEACAM1 | - | 11 | 0.00300 |
| 19 | 45810516 | + | CKM | - | 34 | 0.00926 |
| 19 | 49082439 | - | SULT2B1 | + | 25 | 0.00681 |
| 19 | 52570512 | + | ZNF841 | - | 210 | 0.05718 |
| 19 | 53941038 | - | LOC147804 | + | 1326 | 0.36108 |
| 20 | 18102331 | + | PET117 | + | 1032 | 0.28102 |
| 20 | 29619506 | - | FRG1B | + | 8 | 0.00218 |

TABLE 2-continued

| Chr | Integration locus | Integration strand | Gene symbol | Gene strand | Sequence count | % of reads |
|---|---|---|---|---|---|---|
| 20 | 31137636 | − | LOC149950 | + | 298 | 0.08115 |
| 20 | 31628559 | − | BPIFB6 | + | 1620 | 0.44114 |
| 20 | 43615509 | + | STK4 | + | 14911 | 4.06040 |
| 20 | 51413714 | − | TSHZ2 | + | 928 | 0.25270 |
| 20 | 52201341 | − | ZNF217 | − | 1006 | 0.27394 |
| 21 | 33725813 | − | URB1 | − | 71 | 0.01933 |
| 21 | 37629988 | − | DOPEY2 | + | 1101 | 0.29981 |
| 21 | 37629996 | − | DOPEY2 | + | 4 | 0.00109 |
| 21 | 38418447 | − | PIGP | − | 3866 | 1.05275 |
| 21 | 46219289 | − | UBE2G2 | − | 43 | 0.01171 |
| 22 | 17646335 | + | CECR5-AS1 | + | 271 | 0.07380 |
| 22 | 26185822 | − | MYO18B | + | 32 | 0.00871 |
| 22 | 29472413 | − | KREMEN1 | + | 1 | 0.00027 |
| 22 | 31063260 | − | DUSP18 | − | 4630 | 1.26079 |
| 22 | 40738431 | + | ADSL | + | 188 | 0.05119 |
| 22 | 40910812 | + | MKL1 | − | 14616 | 3.98007 |
| 22 | 42588717 | + | TCF20 | − | 1281 | 0.34883 |
| 22 | 45658074 | + | KIAA0930 | − | 8548 | 2.32770 |
| X | 13383579 | − | LOC100133123 | + | 56 | 0.01525 |
| X | 20243202 | − | RPS6KA3 | − | 1748 | 0.47600 |
| X | 42037388 | − | CASK | − | 826 | 0.22493 |
| X | 46876802 | − | PHF16 | + | 388 | 0.10566 |
| X | 47074130 | − | UBA1 | + | 51 | 0.01389 |
| X | 54900595 | − | TRO | + | 19 | 0.00517 |
| X | 62522518 | + | SPIN4 | − | 1 | 0.00027 |
| X | 71907770 | − | PHKA1 | − | 17 | 0.00463 |
| X | 72779461 | − | LOC139201 | − | 4 | 0.00109 |
| X | 86258507 | + | DACH2 | + | 508 | 0.13833 |
| X | 118627441 | − | SLC25A5 | + | 10 | 0.00272 |
| X | 122820480 | − | THOC2 | − | 988 | 0.26904 |
| X | 123128903 | + | STAG2 | + | 580 | 0.15794 |
| X | 123715395 | + | ODZ1 | − | 174 | 0.04738 |
| X | 131590870 | + | MBNL3 | − | 2 | 0.00054 |
| X | 152213080 | − | PNMA3 | + | 938 | 0.25543 |
| Sample 13 | | | | | | |
| 1 | 12080303 | − | MIIP | + | 3989 | 1.05760 |
| 1 | 17370071 | + | SDHB | − | 9659 | 2.56089 |
| 1 | 19293797 | + | IFFO2 | − | 39124 | 10.37296 |
| 1 | 19293933 | + | IFFO2 | − | 1 | 0.00027 |
| 1 | 25375656 | − | RUNX3 | − | 2160 | 0.57268 |
| 1 | 26904146 | − | RPS6KA1 | + | 1127 | 0.29880 |
| 1 | 27213782 | − | GPN2 | − | 1421 | 0.37675 |
| 1 | 35564441 | − | ZMYM1 | + | 1 | 0.00027 |
| 1 | 35564675 | − | ZMYM1 | + | 1001 | 0.26540 |
| 1 | 36314559 | − | EIF2C4 | + | 3544 | 0.93962 |
| 1 | 52691150 | − | ZFYVE9 | + | 275 | 0.07291 |
| 1 | 86863636 | − | ODF2L | − | 968 | 0.25665 |
| 1 | 111679764 | − | DRAM2 | − | 1 | 0.00027 |
| 1 | 145041972 | − | PDE4DIP | − | 93 | 0.02466 |
| 1 | 172195303 | + | DNM3 | + | 1663 | 0.44091 |
| 1 | 172961624 | + | TNFSF18 | − | 5 | 0.00133 |
| 1 | 181446932 | + | CACNA1E | + | 2604 | 0.69040 |
| 1 | 181447202 | + | CACNA1E | + | 1 | 0.00027 |
| 1 | 198762427 | + | LOC100131234 | − | 5657 | 1.49984 |
| 1 | 198762620 | + | LOC100131234 | − | 1 | 0.00027 |
| 1 | 199096051 | + | LOC100131234 | − | 12 | 0.00318 |
| 1 | 203292079 | − | BTG2 | + | 385 | 0.10208 |
| 1 | 211742777 | + | SLC30A1 | − | 390 | 0.10340 |
| 1 | 235317768 | − | RBM34 | − | 1 | 0.00027 |
| 2 | 29133389 | + | WDR43 | + | 1002 | 0.26566 |
| 2 | 31017629 | − | CAPN13 | − | 1864 | 0.49420 |
| 2 | 36223404 | − | LOC100288911 | − | 1 | 0.00027 |
| 2 | 96968443 | + | SNRNP200 | − | 15 | 0.00398 |
| 2 | 134862627 | − | MIR3679 | + | 504 | 0.13363 |
| 2 | 136804573 | − | DARS | − | 5028 | 1.33308 |
| 2 | 158613542 | − | ACVR1 | − | 86 | 0.02280 |
| 2 | 159800637 | − | TANC1 | + | 1 | 0.00027 |
| 2 | 159800693 | − | TANC1 | + | 2522 | 0.66866 |
| 2 | 162749655 | + | SLC4A10 | + | 53 | 0.01405 |
| 2 | 172607265 | + | DYNC1I2 | + | 9306 | 2.46730 |
| 2 | 191035649 | − | C2orf88 | + | 2233 | 0.59204 |
| 2 | 201861608 | − | FAM126B | − | 2 | 0.00053 |
| 2 | 225873275 | − | MIR4439 | − | 11 | 0.00292 |
| 3 | 1813628 | + | CNTN4 | + | 1541 | 0.40857 |
| 3 | 15473875 | + | EAF1 | + | 1056 | 0.27998 |
| 3 | 18686286 | + | SATB1 | − | 193 | 0.05117 |

TABLE 2-continued

| Chr | Integration locus | Integration strand | Gene symbol | Gene strand | Sequence count | % of reads |
|---|---|---|---|---|---|---|
| 3 | 27126086 | + | NEK10 | − | 1 | 0.00027 |
| 3 | 47846844 | − | DHX30 | + | 1402 | 0.37171 |
| 3 | 52708851 | + | PBRM1 | − | 688 | 0.18241 |
| 3 | 53827595 | − | CACNA1D | + | 11971 | 3.17388 |
| 3 | 59177654 | + | C3orf67 | − | 3 | 0.00080 |
| 3 | 105874980 | − | CBLB | − | 24997 | 6.62746 |
| 3 | 112640249 | + | CD200R1 | − | 3 | 0.00080 |
| 3 | 119714060 | − | GSK3B | − | 317 | 0.08405 |
| 3 | 149879897 | + | LOC646903 | + | 128 | 0.03394 |
| 3 | 151789808 | − | SUCNR1 | + | 5 | 0.00133 |
| 3 | 169966153 | + | PRKCI | + | 2274 | 0.60291 |
| 3 | 187903383 | + | FLJ42393 | + | 8410 | 2.22975 |
| 3 | 189972943 | − | CLDN1 | − | 2 | 0.00053 |
| 3 | 197516033 | − | LRCH3 | + | 1 | 0.00027 |
| 3 | 197516039 | − | LRCH3 | + | 2055 | 0.54484 |
| 4 | 457342 | − | ZNF721 | − | 4095 | 1.08571 |
| 4 | 14980682 | − | LOC441009 | − | 83 | 0.02201 |
| 4 | 40139130 | − | N4BP2 | + | 3 | 0.00080 |
| 4 | 43190766 | + | GRXCR1 | + | 218 | 0.05780 |
| 4 | 114369609 | − | CAMK2D | − | 232 | 0.06151 |
| 4 | 128090142 | + | INTU | + | 933 | 0.24737 |
| 4 | 147062935 | + | LOC100505545 | − | 374 | 0.09916 |
| 4 | 183334218 | − | ODZ3 | + | 892 | 0.23650 |
| 4 | 184620547 | + | TRAPPC11 | + | 59 | 0.01564 |
| 5 | 7916353 | − | MTRR | + | 395 | 0.10473 |
| 5 | 12142253 | − | CTNND2 | − | 1 | 0.00027 |
| 5 | 27758473 | + | LOC643401 | + | 790 | 0.20945 |
| 5 | 54584902 | − | DHX29 | − | 957 | 0.25373 |
| 5 | 64756328 | + | ADAMTS6 | − | 16 | 0.00424 |
| 5 | 84260405 | − | EDIL3 | − | 2 | 0.00053 |
| 5 | 91767870 | − | FLJ42709 | − | 2179 | 0.57772 |
| 5 | 99956946 | − | FAM174A | + | 1 | 0.00027 |
| 5 | 99956986 | − | FAM174A | + | 44 | 0.01167 |
| 5 | 101829426 | − | SLCO6A1 | − | 5491 | 1.45583 |
| 5 | 116565832 | + | LOC728342 | + | 1020 | 0.27043 |
| 5 | 130701954 | − | CDC42SE2 | + | 124 | 0.03288 |
| 5 | 138520445 | − | SIL1 | − | 2 | 0.00053 |
| 5 | 165543731 | − | ODZ2 | + | 299 | 0.07927 |
| 5 | 177736576 | − | COL23A1 | − | 45 | 0.01193 |
| 6 | 34614037 | − | C6orf106 | − | 17 | 0.00451 |
| 6 | 43032317 | + | KLC4 | + | 5170 | 1.37072 |
| 6 | 88228870 | + | RARS2 | − | 885 | 0.23464 |
| 6 | 127178541 | − | RSPO3 | + | 1247 | 0.33062 |
| 6 | 156939286 | + | ARID1B | + | 434 | 0.11507 |
| 6 | 164021092 | − | QKI | + | 1078 | 0.28581 |
| 7 | 2440163 | − | CHST12 | + | 1406 | 0.37277 |
| 7 | 13560724 | − | ETV1 | − | 446 | 0.11825 |
| 7 | 14383530 | − | DGKB | − | 598 | 0.15855 |
| 7 | 36688352 | + | AOAH | − | 5225 | 1.38531 |
| 7 | 44660493 | + | OGDH | + | 3 | 0.00080 |
| 7 | 50506985 | + | FIGNL1 | − | 1 | 0.00027 |
| 7 | 50507260 | − | FIGNL1 | − | 3861 | 1.02367 |
| 7 | 67682868 | − | STAG3L4 | + | 1515 | 0.40167 |
| 7 | 77172753 | − | PTPN12 | + | 321 | 0.08511 |
| 7 | 80066872 | + | GNAT3 | − | 838 | 0.22218 |
| 7 | 99206990 | + | LOC100289187 | + | 3007 | 0.79725 |
| 7 | 100393768 | − | ZAN | + | 3 | 0.00080 |
| 7 | 102077129 | − | ORAI2 | + | 281 | 0.07450 |
| 7 | 109468636 | − | EIF3IP1 | − | 37 | 0.00981 |
| 7 | 133890685 | + | LRGUK | + | 791 | 0.20972 |
| 7 | 139778795 | − | JHDM1D | − | 122 | 0.03235 |
| 8 | 23094646 | + | LOC389641 | + | 16 | 0.00424 |
| 8 | 59755566 | + | TOX | − | 1108 | 0.29376 |
| 8 | 81114555 | − | TPD52 | − | 1 | 0.00027 |
| 8 | 91022225 | − | DECR1 | + | 1013 | 0.26858 |
| 8 | 93039233 | − | RUNX1T1 | − | 1 | 0.00027 |
| 8 | 102779476 | + | NCALD | − | 310 | 0.08219 |
| 8 | 116367115 | + | TRPS1 | − | 569 | 0.15086 |
| 8 | 125125894 | + | FER1L6 | + | 4473 | 1.18593 |
| 8 | 129228032 | − | MIR1208 | + | 1835 | 0.48651 |
| 8 | 133331791 | − | KCNQ3 | − | 523 | 0.13866 |
| 9 | 309198 | − | DOCK8 | + | 182 | 0.04825 |
| 9 | 22591498 | + | FLJ35282 | + | 1 | 0.00027 |
| 9 | 77783139 | − | OSTF1 | + | 573 | 0.15192 |
| 9 | 92085353 | + | SEMA4D | − | 3 | 0.00080 |
| 9 | 135497488 | + | DDX31 | − | 6519 | 1.72838 |
| 10 | 6652389 | − | LOC439949 | + | 2348 | 0.62253 |

TABLE 2-continued

| Chr | Integration locus | Integration strand | Gene symbol | Gene strand | Sequence count | % of reads |
|---|---|---|---|---|---|---|
| 10 | 13491178 | − | BEND7 | − | 14 | 0.00371 |
| 10 | 43935496 | − | ZNF487P | + | 280 | 0.07424 |
| 10 | 49981523 | + | WDFY4 | + | 256 | 0.06787 |
| 10 | 75519293 | + | SEC24C | + | 361 | 0.09571 |
| 10 | 94033611 | + | CPEB3 | − | 42 | 0.01114 |
| 10 | 121241611 | − | RGS10 | − | 19 | 0.00504 |
| 10 | 125748194 | + | CHST15 | − | 3798 | 1.00696 |
| 11 | 15050700 | + | CALCB | + | 2189 | 0.58037 |
| 11 | 27433051 | − | LGR4 | − | 3 | 0.00080 |
| 11 | 31689318 | − | ELP4 | + | 4 | 0.00106 |
| 11 | 47058940 | − | C11orf49 | + | 124 | 0.03288 |
| 11 | 64475041 | − | NRXN2 | − | 5176 | 1.37231 |
| 11 | 86750034 | − | TMEM135 | + | 826 | 0.21900 |
| 11 | 111844231 | − | DIXDC1 | + | 5054 | 1.33997 |
| 11 | 132486593 | − | OPCML | − | 998 | 0.26460 |
| 12 | 17899523 | − | MIR3974 | + | 2 | 0.00053 |
| 12 | 42514402 | − | GXYLT1 | − | 3745 | 0.99291 |
| 12 | 42774833 | − | PPHLN1 | + | 5632 | 1.49321 |
| 12 | 50587332 | − | LIMA1 | − | 26 | 0.00689 |
| 12 | 51373166 | + | SLC11A2 | − | 730 | 0.19355 |
| 12 | 54439818 | + | HOXC4 | + | 21 | 0.00557 |
| 12 | 56581610 | + | SMARCC2 | − | 4919 | 1.30418 |
| 12 | 62998743 | + | MIRLET7I | + | 15881 | 4.21053 |
| 12 | 72868807 | + | TRHDE | + | 2 | 0.00053 |
| 12 | 74840052 | − | ATXN7L3B | + | 3 | 0.00080 |
| 12 | 91770183 | + | DCN | − | 1429 | 0.37887 |
| 12 | 93473698 | + | LOC643339 | − | 4 | 0.00106 |
| 12 | 102955102 | − | IGF1 | − | 10 | 0.00265 |
| 12 | 123358551 | + | VPS37B | − | 18 | 0.00477 |
| 12 | 127600584 | + | LOC440117 | − | 146 | 0.03871 |
| 12 | 133488719 | + | ZNF605 | − | 60 | 0.01591 |
| 13 | 26448242 | − | ATP8A2 | + | 505 | 0.13389 |
| 13 | 45933680 | + | TPT1-AS1 | + | 1 | 0.00027 |
| 13 | 49704688 | − | FNDC3A | + | 63 | 0.01670 |
| 13 | 52949052 | − | THSD1 | − | 2 | 0.00053 |
| 13 | 82787320 | − | SLITRK1 | − | 1 | 0.00027 |
| 13 | 95835270 | − | ABCC4 | − | 5480 | 1.45291 |
| 14 | 23520708 | − | CDH24 | − | 2792 | 0.74024 |
| 14 | 36281659 | − | RALGAPA1 | − | 1 | 0.00027 |
| 14 | 36281754 | − | RALGAPA1 | − | 6794 | 1.80130 |
| 14 | 39886256 | − | FBXO33 | − | 7 | 0.00186 |
| 14 | 40184426 | − | FBXO33 | − | 429 | 0.11374 |
| 14 | 75650300 | + | TMED10 | − | 2111 | 0.55969 |
| 14 | 102289575 | + | PPP2R5C | + | 1987 | 0.52681 |
| 14 | 102831563 | + | TECPR2 | + | 2651 | 0.70286 |
| 14 | 102831620 | + | TECPR2 | + | 1 | 0.00027 |
| 15 | 40046912 | − | FSIP1 | − | 4430 | 1.17453 |
| 15 | 45058736 | + | TRIM69 | + | 5 | 0.00133 |
| 15 | 46573670 | + | SQRDL | + | 1047 | 0.27759 |
| 15 | 48588989 | − | SLC12A1 | + | 2996 | 0.79433 |
| 15 | 50701781 | + | USP8 | + | 8 | 0.00212 |
| 15 | 64833928 | − | ZNF609 | + | 3 | 0.00080 |
| 15 | 65190549 | − | ANKDD1A | + | 94 | 0.02492 |
| 15 | 76226922 | + | FBXO22 | + | 2046 | 0.54246 |
| 15 | 92448919 | − | SLCO3A1 | + | 123 | 0.03261 |
| 16 | 56602613 | − | MT4 | + | 416 | 0.11029 |
| 16 | 68887744 | − | TMCO7 | + | 205 | 0.05435 |
| 16 | 71677248 | − | MARVELD3 | + | 1260 | 0.33406 |
| 16 | 89828309 | − | FANCA | − | 1804 | 0.47830 |
| 17 | 459694 | + | VPS53 | − | 1 | 0.00027 |
| 17 | 40310742 | − | KCNH4 | − | 1 | 0.00027 |
| 17 | 47813879 | + | FAM117A | − | 221 | 0.05859 |
| 17 | 65490090 | + | PITPNC1 | + | 24 | 0.00636 |
| 17 | 73696377 | + | SAP30BP | + | 4553 | 1.20714 |
| 17 | 73741559 | − | ITGB4 | + | 3 | 0.00080 |
| 18 | 44781866 | + | IER3IP1 | − | 248 | 0.06575 |
| 18 | 60793792 | + | BCL2 | − | 2046 | 0.54246 |
| 18 | 64609920 | + | CDH19 | − | 6640 | 1.76047 |
| 18 | 66791234 | − | CCDC102B | + | 32 | 0.00848 |
| 19 | 9361258 | − | OR7E24 | + | 77 | 0.02042 |
| 19 | 10031126 | + | OLFM2 | − | 25 | 0.00663 |
| 19 | 28101928 | − | LOC148189 | − | 2178 | 0.57745 |
| 19 | 36185693 | − | UPK1A | + | 8196 | 2.17301 |
| 19 | 39154862 | − | ACTN4 | + | 63 | 0.01670 |
| 19 | 51324932 | − | KLK1 | + | 50 | 0.01326 |
| 19 | 53271057 | + | ZNF600 | − | 1554 | 0.41201 |
| 19 | 54546645 | + | VSTM1 | − | 17440 | 4.62387 |

TABLE 2-continued

| Chr | Integration locus | Integration strand | Gene symbol | Gene strand | Sequence count | % of reads |
|---|---|---|---|---|---|---|
| 20 | 7678349 | + | HAO1 | − | 342 | 0.09067 |
| 20 | 8449963 | + | PLCB1 | + | 64 | 0.01697 |
| 20 | 45687844 | + | EYA2 | + | 3073 | 0.81475 |
| 21 | 17568748 | − | LINC00478 | + | 8309 | 2.20297 |
| 21 | 42336388 | + | DSCAM | − | 319 | 0.08458 |
| 22 | 21326880 | − | AIFM3 | + | 1461 | 0.38736 |
| 22 | 22594396 | + | VPREB1 | + | 336 | 0.08908 |
| 22 | 27267108 | − | MIAT | + | 44 | 0.01167 |
| 22 | 29391482 | + | ZNRF3 | + | 2125 | 0.56340 |
| 22 | 35549137 | + | ISX | + | 990 | 0.26248 |
| 22 | 42123124 | − | MEI1 | + | 1 | 0.00027 |
| X | 52841815 | + | XAGE5 | + | 5818 | 1.54253 |
| X | 54093379 | + | FAM120C | − | 1631 | 0.43243 |
| X | 78902769 | − | ITM2A | − | 4 | 0.00106 |
| X | 83505799 | + | RPS6KA6 | − | 3393 | 0.89959 |
| X | 108978356 | + | ACSL4 | − | 101 | 0.02678 |
| X | 150211117 | − | HMGB3 | + | 2 | 0.00053 |
| Sample 14 | | | | | | |
| 1 | 10721430 | − | CASZ1 | − | 1240 | 0.25030 |
| 1 | 32485255 | + | KHDRBS1 | + | 2004 | 0.40452 |
| 1 | 32609636 | + | KPNA6 | + | 7 | 0.00141 |
| 1 | 33199900 | + | KIAA1522 | + | 640 | 0.12919 |
| 1 | 53027605 | − | ZCCHC11 | − | 1 | 0.00020 |
| 1 | 78403034 | − | NEXN | + | 1429 | 0.28846 |
| 1 | 90142574 | + | LRRC8C | + | 145 | 0.02927 |
| 1 | 99224507 | + | SNX7 | + | 1 | 0.00020 |
| 1 | 106600604 | − | PRMT6 | + | 489 | 0.09871 |
| 1 | 111424904 | − | CD53 | + | 24 | 0.00484 |
| 1 | 120520316 | − | NOTCH2 | − | 105678 | 21.33198 |
| 1 | 147251917 | − | GJA5 | − | 6 | 0.00121 |
| 1 | 151808704 | − | C2CD4D | − | 136 | 0.02745 |
| 1 | 154230727 | − | UBAP2L | + | 11 | 0.00222 |
| 1 | 155901703 | + | KIAA0907 | − | 218 | 0.04401 |
| 1 | 172949086 | − | TNFSF18 | − | 181 | 0.03654 |
| 1 | 173521494 | + | SLC9A11 | − | 6787 | 1.37001 |
| 1 | 174666352 | + | RABGAP1L | + | 11 | 0.00222 |
| 1 | 198636980 | − | PTPRC | + | 113 | 0.02281 |
| 1 | 203048448 | − | PPFIA4 | + | 275 | 0.05551 |
| 1 | 203862339 | + | SNRPE | + | 33 | 0.00666 |
| 1 | 225522829 | + | DNAH14 | + | 476 | 0.09608 |
| 1 | 233340841 | − | PCNXL2 | − | 1718 | 0.34679 |
| 1 | 244261740 | + | ZNF238 | + | 1405 | 0.28361 |
| 2 | 10797756 | − | NOL10 | − | 567 | 0.11445 |
| 2 | 11199977 | + | FLJ33534 | − | 14 | 0.00283 |
| 2 | 26764687 | + | OTOF | − | 53 | 0.01070 |
| 2 | 32683198 | − | BIRC6 | + | 30 | 0.00606 |
| 2 | 45646803 | − | SRBD1 | − | 1035 | 0.20892 |
| 2 | 61193227 | + | PUS10 | − | 2329 | 0.47013 |
| 2 | 61206788 | + | PUS10 | − | 287 | 0.05793 |
| 2 | 70449707 | − | TIA1 | − | 3879 | 0.78301 |
| 2 | 102394887 | − | MAP4K4 | + | 8 | 0.00161 |
| 2 | 102817769 | − | IL1RL2 | + | 12191 | 2.46085 |
| 2 | 109489830 | − | CCDC138 | + | 251 | 0.05067 |
| 2 | 112410226 | − | ANAPC1 | − | 3 | 0.00061 |
| 2 | 114568072 | + | SLC35F5 | − | 325 | 0.06560 |
| 2 | 124069235 | − | CNTNAP5 | + | 16 | 0.00323 |
| 2 | 127280658 | − | GYPC | + | 33 | 0.00666 |
| 2 | 135047042 | + | MGAT5 | + | 621 | 0.12535 |
| 2 | 142104705 | − | LRP1B | − | 1074 | 0.21680 |
| 2 | 153957584 | − | ARL6IP6 | + | 7 | 0.00141 |
| 2 | 162611220 | − | SLC4A10 | + | 2 | 0.00040 |
| 2 | 167592445 | + | XIRP2 | + | 65 | 0.01312 |
| 2 | 175420693 | − | WIPF1 | − | 192 | 0.03876 |
| 2 | 191437144 | − | TMEM194B | − | 3284 | 0.66290 |
| 2 | 192023407 | − | STAT4 | − | 3061 | 0.61789 |
| 2 | 197971761 | − | ANKRD44 | − | 318 | 0.06419 |
| 2 | 200121648 | − | SATB2 | − | 1 | 0.00020 |
| 2 | 207236725 | + | ZDBF2 | + | 2848 | 0.57489 |
| 2 | 213967357 | − | IKZF2 | − | 362 | 0.07307 |
| 2 | 219484004 | − | PLCD4 | + | 17 | 0.00343 |
| 2 | 226581845 | − | NYAP2 | + | 218 | 0.04401 |
| 2 | 237569109 | − | CXCR7 | + | 2 | 0.00040 |
| 3 | 15355222 | + | SH3BP5 | − | 741 | 0.14958 |
| 3 | 30342833 | + | RBMS3 | + | 606 | 0.12233 |
| 3 | 48788481 | − | PRKAR2A | − | 4 | 0.00081 |
| 3 | 56988214 | − | ARHGEF3 | − | 720 | 0.14534 |

TABLE 2-continued

| Chr | Integration locus | Integration strand | Gene symbol | Gene strand | Sequence count | % of reads |
|---|---|---|---|---|---|---|
| 3 | 63760849 | + | C3orf49 | + | 1 | 0.00020 |
| 3 | 99395944 | − | COL8A1 | + | 399 | 0.08054 |
| 3 | 107446646 | − | BBX | + | 8 | 0.00161 |
| 3 | 109080880 | + | DPPA4 | − | 45 | 0.00908 |
| 3 | 115552976 | − | LSAMP | − | 2 | 0.00040 |
| 3 | 139645197 | + | CLSTN2 | + | 1 | 0.00020 |
| 3 | 176897190 | + | TBL1XR1 | − | 3 | 0.00061 |
| 3 | 184432002 | + | MAGEF1 | − | 55 | 0.01110 |
| 4 | 10019114 | − | SLC2A9 | − | 2 | 0.00040 |
| 4 | 10019171 | − | SLC2A9 | − | 17638 | 3.56038 |
| 4 | 18004910 | − | LCORL | − | 179 | 0.03613 |
| 4 | 19907747 | − | SLIT2 | + | 5081 | 1.02564 |
| 4 | 20926166 | − | KCNIP4 | − | 5903 | 1.19157 |
| 4 | 26202765 | + | RBPJ | + | 4 | 0.00081 |
| 4 | 93433980 | − | GRID2 | + | 322 | 0.06500 |
| 4 | 102224274 | − | PPP3CA | − | 1 | 0.00020 |
| 4 | 102224430 | + | PPP3CA | − | 39 | 0.00787 |
| 4 | 102224593 | − | PPP3CA | − | 7525 | 1.51898 |
| 4 | 109240414 | + | LOC641518 | + | 35 | 0.00707 |
| 4 | 124114714 | − | SPATA5 | + | 637 | 0.12858 |
| 4 | 126012855 | + | FAT4 | + | 3914 | 0.79007 |
| 4 | 181810145 | − | LINC00290 | − | 801 | 0.16169 |
| 4 | 185430562 | + | IRF2 | − | 5 | 0.00101 |
| 5 | 10474449 | − | ROPN1L | + | 72 | 0.01453 |
| 5 | 33387573 | − | TARS | + | 1 | 0.00020 |
| 5 | 37708546 | − | WDR70 | + | 173 | 0.03492 |
| 5 | 39873249 | − | DAB2 | − | 747 | 0.15079 |
| 5 | 55676428 | + | ANKRD55 | − | 8 | 0.00161 |
| 5 | 56850546 | + | ACTBL2 | − | 471 | 0.09508 |
| 5 | 90733668 | + | LOC100129716 | + | 2 | 0.00040 |
| 5 | 95149575 | + | GLRX | − | 473 | 0.09548 |
| 5 | 95472305 | − | MIR583 | + | 172 | 0.03472 |
| 5 | 96476859 | − | LIX1 | − | 153 | 0.03088 |
| 5 | 131958283 | + | RAD50 | + | 677 | 0.13666 |
| 6 | 26050948 | − | HIST1H3C | − | 71 | 0.01433 |
| 6 | 43858275 | − | LOC100132354 | + | 3 | 0.00061 |
| 6 | 86621353 | − | SNHG5 | − | 57 | 0.01151 |
| 6 | 96560678 | + | FUT9 | + | 35 | 0.00707 |
| 6 | 116987132 | + | ZUFSP | − | 1362 | 0.27493 |
| 6 | 119164889 | + | MCM9 | − | 200 | 0.04037 |
| 6 | 130360190 | + | L3MBTL3 | + | 401 | 0.08095 |
| 6 | 134286443 | + | TBPL1 | + | 1144 | 0.23093 |
| 6 | 136990595 | − | MAP3K5 | − | 6301 | 1.27191 |
| 6 | 142519252 | − | VTA1 | + | 1 | 0.00020 |
| 6 | 143676542 | + | AIG1 | + | 961 | 0.19399 |
| 6 | 153493478 | + | RGS17 | − | 919 | 0.18551 |
| 6 | 155095380 | + | SCAF8 | + | 5 | 0.00101 |
| 6 | 155693957 | + | NOX3 | − | 251 | 0.05067 |
| 6 | 155878407 | + | NOX3 | − | 1104 | 0.22285 |
| 6 | 157237693 | − | ARID1B | + | 465 | 0.09386 |
| 7 | 12123383 | − | TMEM106B | + | 4 | 0.00081 |
| 7 | 17986393 | + | SNX13 | − | 103 | 0.02079 |
| 7 | 30550832 | + | GGCT | − | 950 | 0.19177 |
| 7 | 36651974 | + | AOAH | − | 10 | 0.00202 |
| 7 | 38217386 | + | STARD3NL | + | 7 | 0.00141 |
| 7 | 43722363 | − | C7orf44 | − | 180 | 0.03633 |
| 7 | 44501572 | − | NUDCD3 | − | 15 | 0.00303 |
| 7 | 81923069 | + | CACNA2D1 | − | 1 | 0.00020 |
| 7 | 129488394 | + | UBE2H | − | 541 | 0.10921 |
| 8 | 17610279 | − | MTUS1 | − | 1963 | 0.39625 |
| 8 | 19720459 | + | INTS10 | + | 6 | 0.00121 |
| 8 | 20500062 | − | LOC286114 | + | 1613 | 0.32560 |
| 8 | 30014475 | + | DCTN6 | + | 760 | 0.15341 |
| 8 | 71489827 | + | TRAM1 | − | 59 | 0.01191 |
| 8 | 78035874 | + | PEX2 | − | 24 | 0.00484 |
| 8 | 87488099 | + | FAM82B | − | 683 | 0.13787 |
| 8 | 101268197 | − | RNF19A | − | 8 | 0.00161 |
| 8 | 106529732 | − | ZFPM2 | + | 10420 | 2.10336 |
| 8 | 109288844 | + | EIF3E | − | 590 | 0.11910 |
| 8 | 124969062 | + | FER1L6 | + | 2246 | 0.45337 |
| 8 | 127062871 | + | LOC100130231 | − | 2350 | 0.47437 |
| 8 | 129108479 | + | PVT1 | + | 158 | 0.03189 |
| 8 | 129843954 | + | LOC728724 | − | 99 | 0.01998 |
| 9 | 72158532 | − | APBA1 | − | 2083 | 0.42047 |
| 9 | 78795035 | + | PCSK5 | + | 142 | 0.02866 |
| 9 | 82596925 | + | TLE4 | + | 5 | 0.00101 |
| 9 | 91061239 | − | SPIN1 | + | 3 | 0.00061 |

TABLE 2-continued

| Chr | Integration locus | Integration strand | Gene symbol | Gene strand | Sequence count | % of reads |
|---|---|---|---|---|---|---|
| 9 | 104474729 | − | GRIN3A | − | 292 | 0.05894 |
| 9 | 112675029 | + | PALM2 | + | 5417 | 1.09347 |
| 9 | 114277245 | + | ZNF483 | + | 1127 | 0.22749 |
| 9 | 133517723 | + | FUBP3 | + | 630 | 0.12717 |
| 9 | 135271174 | + | TTF1 | − | 4721 | 0.95297 |
| 10 | 4391238 | + | LOC100216001 | − | 5831 | 1.17704 |
| 10 | 12697982 | + | CAMK1D | + | 340 | 0.06863 |
| 10 | 17039963 | + | CUBN | − | 2 | 0.00040 |
| 10 | 50856044 | − | CHAT | + | 4 | 0.00081 |
| 10 | 56954545 | + | PCDH15 | − | 4 | 0.00081 |
| 10 | 75351780 | + | USP54 | − | 1 | 0.00020 |
| 10 | 81092136 | − | PPIF | + | 6 | 0.00121 |
| 10 | 91439097 | + | FLJ37201 | − | 440 | 0.08882 |
| 10 | 101121439 | − | CNNM1 | + | 805 | 0.16250 |
| 10 | 104555631 | + | C10orf26 | + | 67 | 0.01352 |
| 11 | 4391862 | − | OR52B4 | − | 1651 | 0.33327 |
| 11 | 14059098 | + | SPON1 | + | 102 | 0.02059 |
| 11 | 14981862 | + | CALCA | − | 19 | 0.00384 |
| 11 | 15855648 | + | SOX6 | − | 252 | 0.05087 |
| 11 | 26043745 | + | ANO3 | + | 161 | 0.03250 |
| 11 | 58355173 | − | ZFP91-CNTF | + | 43 | 0.00868 |
| 11 | 65292262 | + | SCYL1 | + | 497 | 0.10032 |
| 11 | 66498618 | − | SPTBN2 | − | 1459 | 0.29451 |
| 11 | 77942089 | + | GAB2 | − | 44 | 0.00888 |
| 11 | 79976915 | − | ODZ4 | − | 59 | 0.01191 |
| 11 | 96130261 | + | JRKL | + | 621 | 0.12535 |
| 11 | 113880579 | + | HTR3A | + | 765 | 0.15442 |
| 11 | 116930428 | − | SIK3 | − | 1513 | 0.30541 |
| 11 | 120340340 | + | ARHGEF12 | + | 8232 | 1.66170 |
| 11 | 123174063 | + | MIR4493 | + | 1581 | 0.31914 |
| 12 | 8668503 | + | CLEC4D | + | 235 | 0.04744 |
| 12 | 11833457 | − | ETV6 | + | 170 | 0.03432 |
| 12 | 19662278 | + | AEBP2 | + | 994 | 0.20065 |
| 12 | 28492608 | − | CCDC91 | + | 292 | 0.05894 |
| 12 | 45734365 | − | ANO6 | + | 36 | 0.00727 |
| 12 | 47637227 | + | FAM113B | + | 1819 | 0.36718 |
| 12 | 48650854 | − | OR10AD1 | − | 953 | 0.19237 |
| 12 | 50249314 | − | FAIM2 | − | 31 | 0.00626 |
| 12 | 51471373 | − | CSRNP2 | − | 1652 | 0.33347 |
| 12 | 53269504 | + | KRT8 | − | 1 | 0.00020 |
| 12 | 65054941 | + | RASSF3 | + | 377 | 0.07610 |
| 12 | 65569797 | + | LEMD3 | + | 986 | 0.19903 |
| 12 | 72659594 | + | LOC283392 | − | 402 | 0.08115 |
| 12 | 92729471 | + | CLLU1OS | − | 19 | 0.00384 |
| 12 | 93070210 | − | C12orf74 | + | 2 | 0.00040 |
| 12 | 110852506 | − | ANAPC7 | − | 971 | 0.19600 |
| 12 | 110852508 | − | ANAPC7 | − | 1061 | 0.21417 |
| 12 | 116642466 | + | MED13L | − | 6 | 0.00121 |
| 12 | 120956759 | − | COQ5 | − | 31 | 0.00626 |
| 12 | 121521931 | − | OASL | − | 18 | 0.00363 |
| 12 | 121558737 | + | P2RX7 | + | 1 | 0.00020 |
| 13 | 40670899 | + | LINC00548 | − | 20 | 0.00404 |
| 13 | 41232195 | − | FOXO1 | − | 3287 | 0.66351 |
| 13 | 42646910 | + | DGKH | + | 131 | 0.02644 |
| 13 | 45959039 | − | TPT1-AS1 | + | 557 | 0.11244 |
| 13 | 83509807 | + | SLITRK1 | − | 504 | 0.10174 |
| 13 | 99896667 | + | UBAC2 | − | 136 | 0.02745 |
| 13 | 109758672 | − | MYO16 | + | 1530 | 0.30884 |
| 13 | 114315634 | + | ATP4B | − | 6 | 0.00121 |
| 13 | 115095522 | + | CHAMP1 | + | 12 | 0.00242 |
| 14 | 20924631 | + | APEX1 | + | 8889 | 1.79432 |
| 14 | 20947797 | + | PNP | + | 450 | 0.09084 |
| 14 | 23391592 | + | PRMT5 | − | 6 | 0.00121 |
| 14 | 38003848 | − | MIPOL1 | + | 192 | 0.03876 |
| 14 | 68093006 | − | ARG2 | + | 6 | 0.00121 |
| 14 | 69230757 | − | ZFP36L1 | − | 886 | 0.17885 |
| 14 | 77171905 | + | VASH1 | + | 252 | 0.05087 |
| 14 | 77411096 | + | C14orf166B | + | 62 | 0.01252 |
| 14 | 77867857 | − | NOXRED1 | − | 4 | 0.00081 |
| 14 | 97236788 | + | VRK1 | + | 14 | 0.00283 |
| 14 | 98852825 | + | C14orf177 | + | 2589 | 0.52261 |
| 14 | 99470390 | + | BCL11B | − | 1015 | 0.20489 |
| 15 | 31534514 | − | LOC283710 | − | 1902 | 0.38393 |
| 15 | 31728086 | + | OTUD7A | − | 32 | 0.00646 |
| 15 | 33241491 | + | FMN1 | − | 5486 | 1.10739 |
| 15 | 38876270 | − | RASGRP1 | − | 971 | 0.19600 |
| 15 | 41983934 | + | MIR626 | + | 4 | 0.00081 |

TABLE 2-continued

| Chr | Integration locus | Integration strand | Gene symbol | Gene strand | Sequence count | % of reads |
|---|---|---|---|---|---|---|
| 15 | 47913421 | − | SEMA6D | + | 581 | 0.11728 |
| 15 | 61140116 | + | RORA | − | 2331 | 0.47053 |
| 15 | 63857409 | + | USP3 | + | 3917 | 0.79068 |
| 15 | 63916343 | + | HERC1 | − | 353 | 0.07126 |
| 15 | 66055255 | − | DENND4A | − | 1921 | 0.38777 |
| 15 | 72563272 | − | PARP6 | − | 1433 | 0.28926 |
| 15 | 76534768 | − | ETFA | − | 1 | 0.00020 |
| 15 | 78734744 | − | IREB2 | + | 2 | 0.00040 |
| 15 | 82204534 | − | MEX3B | − | 1807 | 0.36476 |
| 15 | 91165492 | + | CRTC3 | + | 12706 | 2.56481 |
| 15 | 100200088 | − | MEF2A | + | 43 | 0.00868 |
| 16 | 4581042 | + | C16orf5 | − | 216 | 0.04360 |
| 16 | 11252244 | − | CLEC16A | + | 7 | 0.00141 |
| 16 | 23214084 | − | SCNN1G | + | 1152 | 0.23254 |
| 16 | 30741049 | + | SRCAP | + | 11 | 0.00222 |
| 16 | 55666332 | − | SLC6A2 | + | 282 | 0.05692 |
| 16 | 69533066 | − | CYB5B | + | 533 | 0.10759 |
| 16 | 69654878 | − | NFAT5 | + | 627 | 0.12657 |
| 16 | 74590808 | − | GLG1 | − | 72 | 0.01453 |
| 17 | 4293681 | − | UBE2G1 | − | 377 | 0.07610 |
| 17 | 6288551 | + | AIPL1 | − | 11 | 0.00222 |
| 17 | 7497675 | + | FXR2 | − | 845 | 0.17057 |
| 17 | 12062392 | − | MAP2K4 | + | 37 | 0.00747 |
| 17 | 28462020 | + | NSRP1 | + | 4 | 0.00081 |
| 17 | 38626528 | + | TNS4 | − | 101 | 0.02039 |
| 17 | 40404128 | + | STAT5B | − | 57 | 0.01151 |
| 17 | 44265983 | − | KIAA1267 | − | 16 | 0.00323 |
| 17 | 56811457 | − | RAD51C | + | 757 | 0.15281 |
| 17 | 72564296 | + | CD300LD | − | 1197 | 0.24162 |
| 17 | 75666741 | + | LOC100507351 | + | 1675 | 0.33811 |
| 17 | 78905953 | + | RPTOR | + | 1749 | 0.35305 |
| 17 | 80215108 | − | CSNK1D | − | 478 | 0.09649 |
| 18 | 2721720 | + | SMCHD1 | + | 5 | 0.00101 |
| 18 | 19338981 | − | MIB1 | + | 9 | 0.00182 |
| 18 | 41728334 | + | SETBP1 | + | 2220 | 0.44813 |
| 18 | 54993249 | + | ST8SIA3 | + | 668 | 0.13484 |
| 18 | 59083023 | − | CDH20 | + | 1110 | 0.22406 |
| 18 | 73057346 | − | TSHZ1 | + | 75676 | 15.27583 |
| 18 | 74180638 | − | ZNF516 | − | 1 | 0.00020 |
| 18 | 74180879 | − | ZNF516 | − | 113 | 0.02281 |
| 19 | 1928093 | + | SCAMP4 | + | 2 | 0.00040 |
| 19 | 4939350 | − | UHRF1 | + | 1 | 0.00020 |
| 19 | 10140938 | + | RDH8 | + | 1882 | 0.37990 |
| 19 | 10293219 | + | DNMT1 | − | 41 | 0.00828 |
| 19 | 11713183 | − | ZNF627 | + | 26 | 0.00525 |
| 19 | 12938107 | + | RTBDN | − | 103 | 0.02079 |
| 19 | 17377228 | + | BABAM1 | + | 4 | 0.00081 |
| 19 | 42224064 | + | CEACAM5 | + | 199 | 0.04017 |
| 19 | 45725314 | + | EXOC3L2 | − | 3440 | 0.69439 |
| 19 | 53904033 | − | ZNF765 | + | 17 | 0.00343 |
| 19 | 56385832 | − | NLRP4 | + | 2 | 0.00040 |
| 19 | 56385939 | − | NLRP4 | + | 6728 | 1.35810 |
| 19 | 56778748 | + | ZSCAN5A | − | 648 | 0.13080 |
| 19 | 58155158 | − | ZNF211 | + | 522 | 0.10537 |
| 19 | 58954185 | + | ZNF132 | − | 2637 | 0.53230 |
| 20 | 10779029 | + | JAG1 | − | 76 | 0.01534 |
| 20 | 30937778 | − | ASXL1 | + | 2 | 0.00040 |
| 20 | 31387788 | − | DNMT3B | + | 6 | 0.00121 |
| 20 | 47158873 | + | PREX1 | − | 697 | 0.14070 |
| 20 | 47786722 | + | STAU1 | − | 292 | 0.05894 |
| 20 | 47786815 | + | STAU1 | − | 1159 | 0.23395 |
| 21 | 21270955 | − | LINC00320 | − | 8276 | 1.67058 |
| 21 | 34500664 | + | C21orf54 | − | 3218 | 0.64958 |
| 21 | 34600911 | + | IFNAR2 | + | 5075 | 1.02443 |
| 21 | 35639450 | − | LINC00310 | + | 1978 | 0.39928 |
| 21 | 44137254 | − | PDE9A | + | 253 | 0.05107 |
| 21 | 45462551 | − | TRAPPC10 | + | 67 | 0.01352 |
| 21 | 46261904 | + | PTTG1IP | − | 58 | 0.01171 |
| 22 | 17956187 | + | CECR2 | + | 37 | 0.00747 |
| 22 | 17956562 | + | CECR2 | + | 1 | 0.00020 |
| 22 | 21947097 | + | UBE2L3 | + | 18943 | 3.82380 |
| 22 | 21947132 | − | UBE2L3 | + | 1 | 0.00020 |
| 22 | 21947163 | − | UBE2L3 | + | 1 | 0.00020 |
| 22 | 37716297 | + | CYTH4 | + | 10 | 0.00202 |
| 22 | 40738419 | − | ADSL | + | 1936 | 0.39080 |
| X | 50239789 | + | DGKK | − | 354 | 0.07146 |
| X | 53969628 | + | PHF8 | − | 8 | 0.00161 |

TABLE 2-continued

| Chr | Integration locus | Integration strand | Gene symbol | Gene strand | Sequence count | % of reads |
|---|---|---|---|---|---|---|
| X | 64765371 | + | FRMD8P1 | − | 2 | 0.00040 |
| X | 95523591 | − | LOC643486 | − | 1529 | 0.30864 |
| X | 147223878 | − | FMR1NB | + | 1 | 0.00020 |
| X | 153161843 | − | AVPR2 | + | 2334 | 0.47114 |

TABLE 3

| Gene Symbol | Sequence Count | % of reads |
|---|---|---|
| Sample 12 | | |
| MIR622 | 17062 | 4.64613 |
| STK4 | 14911 | 4.06040 |
| MKL1 | 14616 | 3.98007 |
| ASXL2 | 10244 | 2.78953 |
| SOX9 | 9319 | 2.53765 |
| PRKG1 | 8931 | 2.43199 |
| ATP1A3 | 8757 | 2.38461 |
| KIAA0930 | 8548 | 2.32770 |
| HECA | 8110 | 2.20843 |
| SLC25A26 | 7854 | 2.13871 |
| BRD3 | 7102 | 1.93394 |
| RRP9 | 7090 | 1.93067 |
| LIN28A | 6305 | 1.71691 |
| ZNF407 | 4874 | 1.32723 |
| DUSP18 | 4630 | 1.26079 |
| MED10 | 4579 | 1.24690 |
| TBX21 | 4539 | 1.23601 |
| RORA | 4468 | 1.21668 |
| HEMK1 | 4291 | 1.16848 |
| TP53BP1 | 4247 | 1.15650 |
| ODF2 | 4136 | 1.12627 |
| OTOA | 4119 | 1.12164 |
| PIGP | 3866 | 1.05275 |
| C17orf99 | 3739 | 1.01816 |
| TRAP1 | 3683 | 1.00291 |
| All <1% | 187210 | 50.97895 |
| Total reads | 367230 | |
| Unique IS | 473 | |
| Sample 13 | | |
| IFFO2 | 39124 | 10.37296 |
| CBLB | 24997 | 6.62746 |
| VSTM1 | 17440 | 4.62387 |
| MIRLET7I | 15881 | 4.21053 |
| CACNA1D | 11971 | 3.17388 |
| SDHB | 9659 | 2.56089 |
| DYNC1I2 | 9306 | 2.46730 |
| FLJ42393 | 8410 | 2.22975 |
| LINC00478 | 8309 | 2.20297 |
| UPK1A | 8196 | 2.17301 |
| RALGAPA1 | 6794 | 1.80130 |
| CDH19 | 6640 | 1.76047 |
| DDX31 | 6519 | 1.72838 |
| XAGE5 | 5818 | 1.54253 |
| LOC100131234 | 5657 | 1.49984 |
| PPHLN1 | 5632 | 1.49321 |
| SLCO6A1 | 5491 | 1.45583 |
| ABCC4 | 5480 | 1.45291 |
| AOAH | 5225 | 1.38531 |
| NRXN2 | 5176 | 1.37231 |
| KLC4 | 5170 | 1.37072 |
| DIXDC1 | 5054 | 1.33997 |
| DARS | 5028 | 1.33308 |
| SMARCC2 | 4919 | 1.30418 |
| SAP30BP | 4553 | 1.20714 |
| FER1L6 | 4473 | 1.18593 |
| FSIP1 | 4430 | 1.17453 |
| ZNF721 | 4095 | 1.08571 |

TABLE 3-continued

| Gene Symbol | Sequence Count | % of reads |
|---|---|---|
| MIIP | 3989 | 1.05760 |
| FIGNL1 | 3861 | 1.02367 |
| CHST15 | 3798 | 1.00696 |
| All <1% | 116078 | 30.77580 |
| Total reads | 377173 | |
| Unique IS | 212 | |
| Sample 14 | | |
| NOTCH2 | 105678 | 21.33198 |
| TSHZ1 | 75676 | 15.27583 |
| UBE2L3 | 18943 | 3.82380 |
| SLC2A9 | 17638 | 3.56038 |
| CRTC3 | 12706 | 2.56481 |
| IL1RL2 | 12191 | 2.46085 |
| ZFPM2 | 10420 | 2.10336 |
| APEX1 | 8889 | 1.79432 |
| LINC00320 | 8276 | 1.67058 |
| ARHGEF12 | 8232 | 1.66170 |
| PPP3CA | 7525 | 1.51898 |
| SLC9A11 | 6787 | 1.37001 |
| NLRP4 | 6728 | 1.35810 |
| MAP3K5 | 6301 | 1.27191 |
| KCNIP4 | 5903 | 1.19157 |
| LOC100216001 | 5831 | 1.17704 |
| FMN1 | 5486 | 1.10739 |
| PALM2 | 5417 | 1.09347 |
| SLIT2 | 5081 | 1.02564 |
| IFNAR2 | 5075 | 1.02443 |
| All <1% | 156614 | 31.61384 |
| Total reads | 495397 | |
| Unique IS | 293 | |

TABLE 4

| Gene symbol | Highorder | Cluster |
|---|---|---|
| Sample 12 | | |
| SMURF2 | 3 | 1 |
| LIN28A | 2 | 1 |
| PCP4L1 | 2 | 2 |
| MIR4432 | 2 | 1 |
| LOC1720 | 2 | 2 |
| OXSR1 | 2 | 1 |
| SLC25A26 | 2 | 2 |
| EEFSEC | 2 | 3 |
| MED10 | 2 | 1 |
| SERINC5 | 2 | 2 |
| CNOT6 | 2 | 3 |
| HECA | 2 | 1 |
| ATM | 2 | 1 |
| KLRK1 | 2 | 1 |
| TMBIM6 | 2 | 2 |
| CHEK2P2 | 2 | 1 |
| CYP1A1 | 2 | 2 |
| HEATR3 | 2 | 1 |
| CCDC105 | 2 | 1 |
| ZNF100 | 2 | 2 |
| DOPEY2 | 2 | 1 |
| SPSB1 | 0 | 0 |
| ALPL | 0 | 0 |

TABLE 4-continued

| Gene symbol | Highorder | Cluster |
|---|---|---|
| YTHDF2 | 0 | 0 |
| PUM1 | 0 | 0 |
| LCK | 0 | 0 |
| ZBTB8OS | 0 | 0 |
| CSF3R | 0 | 0 |
| C1orf109 | 0 | 0 |
| MACF1 | 0 | 0 |
| PPIEL | 0 | 0 |
| ST3GAL3 | 0 | 0 |
| HSD52 | 0 | 0 |
| DOCK7 | 0 | 0 |
| MGC27382 | 0 | 0 |
| LPHN2 | 0 | 0 |
| CLCA1 | 0 | 0 |
| HS2ST1 | 0 | 0 |
| TGFBR3 | 0 | 0 |
| EVI5 | 0 | 0 |
| CDC14A | 0 | 0 |
| ADORA3 | 0 | 0 |
| LOC388692 | 0 | 0 |
| PLEKHO1 | 0 | 0 |
| VPS72 | 0 | 0 |
| TUFT1 | 0 | 0 |
| POGK | 0 | 0 |
| C1orf114 | 0 | 0 |
| TNFSF18 | 0 | 0 |
| MRPS14 | 0 | 0 |
| RASAL2 | 0 | 0 |
| DHX9 | 0 | 0 |
| TSEN15 | 0 | 0 |
| PLA2G4A | 0 | 0 |
| NR5A2 | 0 | 0 |
| NAV1 | 0 | 0 |
| CR2 | 0 | 0 |
| GPATCH2 | 0 | 0 |
| C1orf140 | 0 | 0 |
| FAM177B | 0 | 0 |
| CHRM3 | 0 | 0 |
| AKT3 | 0 | 0 |
| GREB1 | 0 | 0 |
| NBAS | 0 | 0 |
| ASXL2 | 0 | 0 |
| RAB10 | 0 | 0 |
| ZNF512 | 0 | 0 |
| BRE | 0 | 0 |
| ALK | 0 | 0 |
| YPEL5 | 0 | 0 |
| LBH | 0 | 0 |
| MIR548AD | 0 | 0 |
| SRBD1 | 0 | 0 |
| TSPYL6 | 0 | 0 |
| NFU1 | 0 | 0 |
| ZNF638 | 0 | 0 |
| SLC4A5 | 0 | 0 |
| GCFC2 | 0 | 0 |
| DUSP2 | 0 | 0 |
| EIF5B | 0 | 0 |
| IL1R1 | 0 | 0 |
| IL1RL2 | 0 | 0 |
| SULT1C3 | 0 | 0 |
| DPP4 | 0 | 0 |
| XIRP2 | 0 | 0 |
| METTL8 | 0 | 0 |
| SP3 | 0 | 0 |
| ZNF385B | 0 | 0 |
| UBE2E3 | 0 | 0 |
| STAT4 | 0 | 0 |
| HECW2 | 0 | 0 |
| PGAP1 | 0 | 0 |
| SPATS2L | 0 | 0 |
| DOCK10 | 0 | 0 |
| SLC16A14 | 0 | 0 |
| CAB39 | 0 | 0 |
| LOC150935 | 0 | 0 |
| CPNE9 | 0 | 0 |
| TBC1D5 | 0 | 0 |
| ARPP21 | 0 | 0 |
| GOLGA4 | 0 | 0 |
| CCR3 | 0 | 0 |
| SCAP | 0 | 0 |
| HEMK1 | 0 | 0 |
| RRP9 | 0 | 0 |
| RYBP | 0 | 0 |
| FILIP1L | 0 | 0 |
| MYH15 | 0 | 0 |
| GAP43 | 0 | 0 |
| LSAMP | 0 | 0 |
| GSK3B | 0 | 0 |
| SEC22A | 0 | 0 |
| PLXNA1 | 0 | 0 |
| TMCC1 | 0 | 0 |
| NPHP3-AS1 | 0 | 0 |
| ARMC8 | 0 | 0 |
| LOC100507389 | 0 | 0 |
| LEKR1 | 0 | 0 |
| LOC647107 | 0 | 0 |
| RPL22L1 | 0 | 0 |
| VPS8 | 0 | 0 |
| TFRC | 0 | 0 |
| ANAPC4 | 0 | 0 |
| OCIAD1 | 0 | 0 |
| SCFD2 | 0 | 0 |
| RPL21P44 | 0 | 0 |
| NOA1 | 0 | 0 |
| LPHN3 | 0 | 0 |
| TECRL | 0 | 0 |
| LOC100144602 | 0 | 0 |
| SULT1B1 | 0 | 0 |
| FAM190A | 0 | 0 |
| C4orf37 | 0 | 0 |
| C4orf49 | 0 | 0 |
| ZNF827 | 0 | 0 |
| RNF175 | 0 | 0 |
| FSTL5 | 0 | 0 |
| DDX60L | 0 | 0 |
| GALNT7 | 0 | 0 |
| GLRA3 | 0 | 0 |
| LOC285501 | 0 | 0 |
| LOC255167 | 0 | 0 |
| CDH12 | 0 | 0 |
| DAB2 | 0 | 0 |
| DDX4 | 0 | 0 |
| KIF2A | 0 | 0 |
| HTR1A | 0 | 0 |
| AP3B1 | 0 | 0 |
| FLJ42709 | 0 | 0 |
| MIR583 | 0 | 0 |
| HINT1 | 0 | 0 |
| RAPGEF6 | 0 | 0 |
| ABLIM3 | 0 | 0 |
| TCOF1 | 0 | 0 |
| ITK | 0 | 0 |
| CLINT1 | 0 | 0 |
| MAT2B | 0 | 0 |
| FAM196B | 0 | 0 |
| LOC100506207 | 0 | 0 |
| LINC00340 | 0 | 0 |
| SLC17A4 | 0 | 0 |
| HLA-C | 0 | 0 |
| FKBP5 | 0 | 0 |
| DNAH8 | 0 | 0 |
| LRFN2 | 0 | 0 |
| CCND3 | 0 | 0 |
| BMP5 | 0 | 0 |
| GUSBP4 | 0 | 0 |
| EYS | 0 | 0 |
| COL12A1 | 0 | 0 |
| BCKDHB | 0 | 0 |
| FUT9 | 0 | 0 |
| RTN4IP1 | 0 | 0 |
| FOXO3 | 0 | 0 |
| LOC285762 | 0 | 0 |
| NCOA7 | 0 | 0 |
| HIVEP2 | 0 | 0 |
| OPRM1 | 0 | 0 |
| SYNJ2 | 0 | 0 |

TABLE 4-continued

| Gene symbol | Highorder | Cluster |
|---|---|---|
| MAFK | 0 | 0 |
| AGR3 | 0 | 0 |
| ZPBP | 0 | 0 |
| IKZF1 | 0 | 0 |
| CALN1 | 0 | 0 |
| HIP1 | 0 | 0 |
| RSBN1L | 0 | 0 |
| SEMA3D | 0 | 0 |
| MOGAT3 | 0 | 0 |
| SYPL1 | 0 | 0 |
| TMEM168 | 0 | 0 |
| GPR85 | 0 | 0 |
| SND1 | 0 | 0 |
| KLF14 | 0 | 0 |
| LRGUK | 0 | 0 |
| ZNF467 | 0 | 0 |
| RHEB | 0 | 0 |
| MYOM2 | 0 | 0 |
| LOC100287015 | 0 | 0 |
| KIAA1456 | 0 | 0 |
| ZNF395 | 0 | 0 |
| CLVS1 | 0 | 0 |
| CPA6 | 0 | 0 |
| SLCO5A1 | 0 | 0 |
| STMN2 | 0 | 0 |
| CA13 | 0 | 0 |
| ATP6V0D2 | 0 | 0 |
| PCAT1 | 0 | 0 |
| LOC728724 | 0 | 0 |
| EFR3A | 0 | 0 |
| TG | 0 | 0 |
| LOC100288181 | 0 | 0 |
| INSL4 | 0 | 0 |
| LOC401497 | 0 | 0 |
| PRUNE2 | 0 | 0 |
| C9orf170 | 0 | 0 |
| FAM120AOS | 0 | 0 |
| HSD17B3 | 0 | 0 |
| KIAA0368 | 0 | 0 |
| C9orf84 | 0 | 0 |
| PTBP3 | 0 | 0 |
| KIAA1958 | 0 | 0 |
| C9orf43 | 0 | 0 |
| DBC1 | 0 | 0 |
| DENND1A | 0 | 0 |
| ZBTB43 | 0 | 0 |
| ODF2 | 0 | 0 |
| EXOSC2 | 0 | 0 |
| BRD3 | 0 | 0 |
| FRMD4A | 0 | 0 |
| RSU1 | 0 | 0 |
| ARL5B | 0 | 0 |
| DNAJC1 | 0 | 0 |
| LOC100505583 | 0 | 0 |
| PRKG1 | 0 | 0 |
| DKK1 | 0 | 0 |
| SPOCK2 | 0 | 0 |
| ASCC1 | 0 | 0 |
| KCNMA1 | 0 | 0 |
| NRG3 | 0 | 0 |
| C10orf99 | 0 | 0 |
| ANKRD22 | 0 | 0 |
| MIR4679-2 | 0 | 0 |
| SLC16A12 | 0 | 0 |
| CUTC | 0 | 0 |
| LINC00263 | 0 | 0 |
| DPCD | 0 | 0 |
| SUFU | 0 | 0 |
| VTI1A | 0 | 0 |
| C10orf46 | 0 | 0 |
| DOCK1 | 0 | 0 |
| CYP2E1 | 0 | 0 |
| RNH1 | 0 | 0 |
| UBQLNL | 0 | 0 |
| SBF2 | 0 | 0 |
| SLC17A6 | 0 | 0 |
| CAPRIN1 | 0 | 0 |
| EXT2 | 0 | 0 |
| PRDM11 | 0 | 0 |
| TRIM48 | 0 | 0 |
| OR10W1 | 0 | 0 |
| PATL1 | 0 | 0 |
| LGALS12 | 0 | 0 |
| UVRAG | 0 | 0 |
| C11orf73 | 0 | 0 |
| CTSC | 0 | 0 |
| HEPHL1 | 0 | 0 |
| MTMR2 | 0 | 0 |
| MAML2 | 0 | 0 |
| PGR | 0 | 0 |
| BIRC2 | 0 | 0 |
| SLN | 0 | 0 |
| ZC3H12C | 0 | 0 |
| RDX | 0 | 0 |
| SCN2B | 0 | 0 |
| MPZL2 | 0 | 0 |
| DDX6 | 0 | 0 |
| UBASH3B | 0 | 0 |
| STT3A | 0 | 0 |
| ETS1 | 0 | 0 |
| LOC283177 | 0 | 0 |
| KDM5A | 0 | 0 |
| NINJ2 | 0 | 0 |
| CD163L1 | 0 | 0 |
| EMP1 | 0 | 0 |
| PLEKHA5 | 0 | 0 |
| IFLTD1 | 0 | 0 |
| FAM113B | 0 | 0 |
| TUBA1C | 0 | 0 |
| ITGB7 | 0 | 0 |
| NCKAP1L | 0 | 0 |
| BAZ2A | 0 | 0 |
| SLC16A7 | 0 | 0 |
| CNOT2 | 0 | 0 |
| KCNMB4 | 0 | 0 |
| ZDHHC17 | 0 | 0 |
| LRRIQ1 | 0 | 0 |
| DCN | 0 | 0 |
| ANKS1B | 0 | 0 |
| TXNRD1 | 0 | 0 |
| ATP2A2 | 0 | 0 |
| PITPNM2 | 0 | 0 |
| ZDHHC20 | 0 | 0 |
| LINC00426 | 0 | 0 |
| STARD13 | 0 | 0 |
| KIAA0564 | 0 | 0 |
| DNAJC15 | 0 | 0 |
| TSC22D1 | 0 | 0 |
| SIAH3 | 0 | 0 |
| OR7E156P | 0 | 0 |
| KCTD12 | 0 | 0 |
| MIR622 | 0 | 0 |
| FKSG29 | 0 | 0 |
| TMTC4 | 0 | 0 |
| CUL4A | 0 | 0 |
| OR4L1 | 0 | 0 |
| CTSG | 0 | 0 |
| NPAS3 | 0 | 0 |
| KLHDC1 | 0 | 0 |
| ARF6 | 0 | 0 |
| CDKN3 | 0 | 0 |
| KTN1-AS1 | 0 | 0 |
| PELI2 | 0 | 0 |
| HIF1A | 0 | 0 |
| ATP6V1D | 0 | 0 |
| SLC39A9 | 0 | 0 |
| MIR4505 | 0 | 0 |
| JDP2 | 0 | 0 |
| C14orf177 | 0 | 0 |
| KLC1 | 0 | 0 |
| TDRD9 | 0 | 0 |
| C15orf29 | 0 | 0 |
| TP53BP1 | 0 | 0 |
| TRIM69 | 0 | 0 |
| TRPM7 | 0 | 0 |
| UNC13C | 0 | 0 |

TABLE 4-continued

| Gene symbol | Highorder | Cluster |
|---|---|---|
| RORA | 0 | 0 |
| PARP16 | 0 | 0 |
| LRRC49 | 0 | 0 |
| SCAPER | 0 | 0 |
| ACSBG1 | 0 | 0 |
| CRTC3 | 0 | 0 |
| ZNF75A | 0 | 0 |
| TRAP1 | 0 | 0 |
| RBFOX1 | 0 | 0 |
| ABAT | 0 | 0 |
| C16orf72 | 0 | 0 |
| LITAF | 0 | 0 |
| TXNDC11 | 0 | 0 |
| OTOA | 0 | 0 |
| SBK1 | 0 | 0 |
| FTO | 0 | 0 |
| CNOT1 | 0 | 0 |
| NFATC3 | 0 | 0 |
| CHTF8 | 0 | 0 |
| WWP2 | 0 | 0 |
| ZFHX3 | 0 | 0 |
| LOC100506172 | 0 | 0 |
| SENP3-EIF4A1 | 0 | 0 |
| PIK3R5 | 0 | 0 |
| HS3ST3A1 | 0 | 0 |
| COX10 | 0 | 0 |
| CDRT1 | 0 | 0 |
| FBXW10 | 0 | 0 |
| AKAP10 | 0 | 0 |
| NLK | 0 | 0 |
| CCT6B | 0 | 0 |
| IKZF3 | 0 | 0 |
| THRA | 0 | 0 |
| CCR7 | 0 | 0 |
| ATP6V0A1 | 0 | 0 |
| TBX21 | 0 | 0 |
| CA10 | 0 | 0 |
| YPEL2 | 0 | 0 |
| VMP1 | 0 | 0 |
| MED13 | 0 | 0 |
| SMURF2 | 0 | 0 |
| ABCA6 | 0 | 0 |
| SOX9 | 0 | 0 |
| GRB2 | 0 | 0 |
| C17orf99 | 0 | 0 |
| RPTOR | 0 | 0 |
| MYOM1 | 0 | 0 |
| DLGAP1 | 0 | 0 |
| ZNF24 | 0 | 0 |
| KC6 | 0 | 0 |
| ACAA2 | 0 | 0 |
| DCC | 0 | 0 |
| LOC100505474 | 0 | 0 |
| ATP8B1 | 0 | 0 |
| PMAIP1 | 0 | 0 |
| MC4R | 0 | 0 |
| CDH20 | 0 | 0 |
| BCL2 | 0 | 0 |
| ZNF407 | 0 | 0 |
| IZUMO4 | 0 | 0 |
| NFIC | 0 | 0 |
| ZNF812 | 0 | 0 |
| ZNF844 | 0 | 0 |
| MIR639 | 0 | 0 |
| CYP4F12 | 0 | 0 |
| CIB3 | 0 | 0 |
| ARHGEF1 | 0 | 0 |
| ATP1A3 | 0 | 0 |
| CEACAM1 | 0 | 0 |
| CKM | 0 | 0 |
| SULT2B1 | 0 | 0 |
| ZNF841 | 0 | 0 |
| LOC147804 | 0 | 0 |
| PET117 | 0 | 0 |
| FRG1B | 0 | 0 |
| LOC149950 | 0 | 0 |
| BPIFB6 | 0 | 0 |

TABLE 4-continued

| Gene symbol | Highorder | Cluster |
|---|---|---|
| STK4 | 0 | 0 |
| TSHZ2 | 0 | 0 |
| ZNF217 | 0 | 0 |
| URB1 | 0 | 0 |
| PIGP | 0 | 0 |
| UBE2G2 | 0 | 0 |
| CECR5-AS1 | 0 | 0 |
| MYO18B | 0 | 0 |
| KREMEN1 | 0 | 0 |
| DUSP18 | 0 | 0 |
| ADSL | 0 | 0 |
| MKL1 | 0 | 0 |
| TCF20 | 0 | 0 |
| KIAA0930 | 0 | 0 |
| LOC100133123 | 0 | 0 |
| RPS6KA3 | 0 | 0 |
| CASK | 0 | 0 |
| PHF16 | 0 | 0 |
| UBA1 | 0 | 0 |
| TRO | 0 | 0 |
| SPIN4 | 0 | 0 |
| PHKA1 | 0 | 0 |
| LOC139201 | 0 | 0 |
| DACH2 | 0 | 0 |
| SLC25A5 | 0 | 0 |
| THOC2 | 0 | 0 |
| STAG2 | 0 | 0 |
| ODZ1 | 0 | 0 |
| MBNL3 | 0 | 0 |
| PNMA3 | 0 | 0 |
| Sample 13 | | |
| IFFO2 | 2 | 1 |
| ZMYM1 | 2 | 2 |
| CACNA1E | 2 | 3 |
| LOC100131234 | 2 | 4 |
| TANC1 | 2 | 1 |
| LRCH3 | 2 | 1 |
| FAM174A | 2 | 1 |
| FIGNL1 | 2 | 1 |
| RALGAPA1 | 2 | 1 |
| TECPR2 | 2 | 2 |
| MIIP | 0 | 0 |
| SDHB | 0 | 0 |
| RUNX3 | 0 | 0 |
| RPS6KA1 | 0 | 0 |
| GPN2 | 0 | 0 |
| EIF2C4 | 0 | 0 |
| ZFYVE9 | 0 | 0 |
| ODF2L | 0 | 0 |
| DRAM2 | 0 | 0 |
| PDE4DIP | 0 | 0 |
| DNM3 | 0 | 0 |
| TNFSF18 | 0 | 0 |
| LOC100131234 | 0 | 0 |
| BTG2 | 0 | 0 |
| SLC30A1 | 0 | 0 |
| RBM34 | 0 | 0 |
| WDR43 | 0 | 0 |
| CAPN13 | 0 | 0 |
| LOC100288911 | 0 | 0 |
| SNRNP200 | 0 | 0 |
| MIR3679 | 0 | 0 |
| DARS | 0 | 0 |
| ACVR1 | 0 | 0 |
| SLC4A10 | 0 | 0 |
| DYNC1I2 | 0 | 0 |
| C2orf88 | 0 | 0 |
| FAM126B | 0 | 0 |
| MIR4439 | 0 | 0 |
| CNTN4 | 0 | 0 |
| EAF1 | 0 | 0 |
| SATB1 | 0 | 0 |
| NEK10 | 0 | 0 |
| DHX30 | 0 | 0 |
| PBRM1 | 0 | 0 |
| CACNA1D | 0 | 0 |
| C3orf67 | 0 | 0 |

TABLE 4-continued

| Gene symbol | Highorder | Cluster |
|---|---|---|
| CBLB | 0 | 0 |
| CD200R1 | 0 | 0 |
| GSK3B | 0 | 0 |
| LOC646903 | 0 | 0 |
| SUCNR1 | 0 | 0 |
| PRKCI | 0 | 0 |
| FLJ42393 | 0 | 0 |
| CLDN1 | 0 | 0 |
| ZNF721 | 0 | 0 |
| LOC441009 | 0 | 0 |
| N4BP2 | 0 | 0 |
| GRXCR1 | 0 | 0 |
| CAMK2D | 0 | 0 |
| INTU | 0 | 0 |
| LOC100505545 | 0 | 0 |
| ODZ3 | 0 | 0 |
| TRAPPC11 | 0 | 0 |
| MTRR | 0 | 0 |
| CTNND2 | 0 | 0 |
| LOC643401 | 0 | 0 |
| DHX29 | 0 | 0 |
| ADAMTS6 | 0 | 0 |
| EDIL3 | 0 | 0 |
| FLJ42709 | 0 | 0 |
| SLCO6A1 | 0 | 0 |
| LOC728342 | 0 | 0 |
| CDC42SE2 | 0 | 0 |
| SIL1 | 0 | 0 |
| ODZ2 | 0 | 0 |
| COL23A1 | 0 | 0 |
| C6orf106 | 0 | 0 |
| KLC4 | 0 | 0 |
| RARS2 | 0 | 0 |
| RSPO3 | 0 | 0 |
| ARID1B | 0 | 0 |
| QKI | 0 | 0 |
| CHST12 | 0 | 0 |
| ETV1 | 0 | 0 |
| DGKB | 0 | 0 |
| AOAH | 0 | 0 |
| OGDH | 0 | 0 |
| STAG3L4 | 0 | 0 |
| PTPN12 | 0 | 0 |
| GNAT3 | 0 | 0 |
| LOC100289187 | 0 | 0 |
| ZAN | 0 | 0 |
| ORAI2 | 0 | 0 |
| EIF3IP1 | 0 | 0 |
| LRGUK | 0 | 0 |
| JHDM1D | 0 | 0 |
| LOC389641 | 0 | 0 |
| TOX | 0 | 0 |
| TPD52 | 0 | 0 |
| DECR1 | 0 | 0 |
| RUNX1T1 | 0 | 0 |
| NCALD | 0 | 0 |
| TRPS1 | 0 | 0 |
| FER1L6 | 0 | 0 |
| MIR1208 | 0 | 0 |
| KCNQ3 | 0 | 0 |
| DOCK8 | 0 | 0 |
| FLJ35282 | 0 | 0 |
| OSTF1 | 0 | 0 |
| SEMA4D | 0 | 0 |
| DDX31 | 0 | 0 |
| LOC439949 | 0 | 0 |
| BEND7 | 0 | 0 |
| ZNF487P | 0 | 0 |
| WDFY4 | 0 | 0 |
| SEC24C | 0 | 0 |
| CPEB3 | 0 | 0 |
| RGS10 | 0 | 0 |
| CHST15 | 0 | 0 |
| CALCB | 0 | 0 |
| LGR4 | 0 | 0 |
| ELP4 | 0 | 0 |
| C11orf49 | 0 | 0 |
| NRXN2 | 0 | 0 |
| TMEM135 | 0 | 0 |
| DIXDC1 | 0 | 0 |
| OPCML | 0 | 0 |
| MIR3974 | 0 | 0 |
| GXYLT1 | 0 | 0 |
| PPHLN1 | 0 | 0 |
| LIMA1 | 0 | 0 |
| SLC11A2 | 0 | 0 |
| HOXC4 | 0 | 0 |
| SMARCC2 | 0 | 0 |
| MIRLET7I | 0 | 0 |
| TRHDE | 0 | 0 |
| ATXN7L3B | 0 | 0 |
| DCN | 0 | 0 |
| LOC643339 | 0 | 0 |
| IGF1 | 0 | 0 |
| VPS37B | 0 | 0 |
| LOC440117 | 0 | 0 |
| ZNF605 | 0 | 0 |
| ATP8A2 | 0 | 0 |
| TPT1-AS1 | 0 | 0 |
| FNDC3A | 0 | 0 |
| THSD1 | 0 | 0 |
| SLITRK1 | 0 | 0 |
| ABCC4 | 0 | 0 |
| CDH24 | 0 | 0 |
| FBXO33 | 0 | 0 |
| TMED10 | 0 | 0 |
| PPP2R5C | 0 | 0 |
| FSIP1 | 0 | 0 |
| TRIM69 | 0 | 0 |
| SQRDL | 0 | 0 |
| SLC12A1 | 0 | 0 |
| USP8 | 0 | 0 |
| ZNF609 | 0 | 0 |
| ANKDD1A | 0 | 0 |
| FBXO22 | 0 | 0 |
| SLCO3A1 | 0 | 0 |
| MT4 | 0 | 0 |
| TMCO7 | 0 | 0 |
| MARVELD3 | 0 | 0 |
| FANCA | 0 | 0 |
| VPS53 | 0 | 0 |
| KCNH4 | 0 | 0 |
| FAM117A | 0 | 0 |
| PITPNC1 | 0 | 0 |
| SAP30BP | 0 | 0 |
| ITGB4 | 0 | 0 |
| IER3IP1 | 0 | 0 |
| BCL2 | 0 | 0 |
| CDH19 | 0 | 0 |
| CCDC102B | 0 | 0 |
| OR7E24 | 0 | 0 |
| OLFM2 | 0 | 0 |
| LOC148189 | 0 | 0 |
| UPK1A | 0 | 0 |
| ACTN4 | 0 | 0 |
| KLK1 | 0 | 0 |
| ZNF600 | 0 | 0 |
| VSTM1 | 0 | 0 |
| HAO1 | 0 | 0 |
| PLCB1 | 0 | 0 |
| EYA2 | 0 | 0 |
| LINC00478 | 0 | 0 |
| DSCAM | 0 | 0 |
| AIFM3 | 0 | 0 |
| VPREB1 | 0 | 0 |
| MIAT | 0 | 0 |
| ZNRF3 | 0 | 0 |
| ISX | 0 | 0 |
| MEI1 | 0 | 0 |
| XAGE5 | 0 | 0 |
| FAM120C | 0 | 0 |

TABLE 4-continued

| Gene symbol | Highorder | Cluster |
|---|---|---|
| ITM2A | 0 | 0 |
| RPS6KA6 | 0 | 0 |
| ACSL4 | 0 | 0 |
| HMGB3 | 0 | 0 |
| Sample 14 | | |
| PPP3CA | 3 | 2 |
| UBE2L3 | 3 | 2 |
| PUS10 | 2 | 1 |
| SLC2A9 | 2 | 1 |
| ANAPC7 | 2 | 1 |
| APEX1 | 2 | 1 |
| PNP | 2 | 1 |
| ZNF516 | 2 | 1 |
| NLRP4 | 2 | 1 |
| STAU1 | 2 | 1 |
| CECR2 | 2 | 1 |
| CASZ1 | 0 | 0 |
| KHDRBS1 | 0 | 0 |
| KPNA6 | 0 | 0 |
| KIAA1522 | 0 | 0 |
| ZCCHC11 | 0 | 0 |
| NEXN | 0 | 0 |
| LRRC8C | 0 | 0 |
| SNX7 | 0 | 0 |
| PRMT6 | 0 | 0 |
| CD53 | 0 | 0 |
| NOTCH2 | 0 | 0 |
| GJA5 | 0 | 0 |
| C2CD4D | 0 | 0 |
| UBAP2L | 0 | 0 |
| KIAA0907 | 0 | 0 |
| TNFSF18 | 0 | 0 |
| SLC9A11 | 0 | 0 |
| RABGAP1L | 0 | 0 |
| PTPRC | 0 | 0 |
| PPFIA4 | 0 | 0 |
| SNRPE | 0 | 0 |
| DNAH14 | 0 | 0 |
| PCNXL2 | 0 | 0 |
| ZNF238 | 0 | 0 |
| NOL10 | 0 | 0 |
| FLJ33534 | 0 | 0 |
| OTOF | 0 | 0 |
| BIRC6 | 0 | 0 |
| SRBD1 | 0 | 0 |
| TIA1 | 0 | 0 |
| MAP4K4 | 0 | 0 |
| IL1RL2 | 0 | 0 |
| CCDC138 | 0 | 0 |
| ANAPC1 | 0 | 0 |
| SLC35F5 | 0 | 0 |
| CNTNAP5 | 0 | 0 |
| GYPC | 0 | 0 |
| MGAT5 | 0 | 0 |
| LRP1B | 0 | 0 |
| ARL6IP6 | 0 | 0 |
| SLC4A10 | 0 | 0 |
| XIRP2 | 0 | 0 |
| WIPF1 | 0 | 0 |
| TMEM194B | 0 | 0 |
| STAT4 | 0 | 0 |
| ANKRD44 | 0 | 0 |
| SATB2 | 0 | 0 |
| ZDBF2 | 0 | 0 |
| IKZF2 | 0 | 0 |
| PLCD4 | 0 | 0 |
| NYAP2 | 0 | 0 |
| CXCR7 | 0 | 0 |
| SH3BP5 | 0 | 0 |
| RBMS3 | 0 | 0 |
| PRKAR2A | 0 | 0 |
| ARHGEF3 | 0 | 0 |
| C3orf49 | 0 | 0 |
| COL8A1 | 0 | 0 |
| BBX | 0 | 0 |
| DPPA4 | 0 | 0 |
| LSAMP | 0 | 0 |
| CLSTN2 | 0 | 0 |
| TBL1XR1 | 0 | 0 |
| MAGEF1 | 0 | 0 |
| LCORL | 0 | 0 |
| SLIT2 | 0 | 0 |
| KCNIP4 | 0 | 0 |
| RBPJ | 0 | 0 |
| GRID2 | 0 | 0 |
| LOC641518 | 0 | 0 |
| SPATA5 | 0 | 0 |
| FAT4 | 0 | 0 |
| LINC00290 | 0 | 0 |
| IRF2 | 0 | 0 |
| ROPN1L | 0 | 0 |
| TARS | 0 | 0 |
| WDR70 | 0 | 0 |
| DAB2 | 0 | 0 |
| ANKRD55 | 0 | 0 |
| ACTBL2 | 0 | 0 |
| LOC100129716 | 0 | 0 |
| GLRX | 0 | 0 |
| MIR583 | 0 | 0 |
| LIX1 | 0 | 0 |
| RAD50 | 0 | 0 |
| HIST1H3C | 0 | 0 |
| LOC100132354 | 0 | 0 |
| SNHG5 | 0 | 0 |
| FUT9 | 0 | 0 |
| ZUFSP | 0 | 0 |
| MCM9 | 0 | 0 |
| L3MBTL3 | 0 | 0 |
| TBPL1 | 0 | 0 |
| MAP3K5 | 0 | 0 |
| VTA1 | 0 | 0 |
| AIG1 | 0 | 0 |
| RGS17 | 0 | 0 |
| SCAF8 | 0 | 0 |
| NOX3 | 0 | 0 |
| ARID1B | 0 | 0 |
| TMEM106B | 0 | 0 |
| SNX13 | 0 | 0 |
| GGCT | 0 | 0 |
| AOAH | 0 | 0 |
| STARD3NL | 0 | 0 |
| C7orf44 | 0 | 0 |
| NUDCD3 | 0 | 0 |
| CACNA2D1 | 0 | 0 |
| UBE2H | 0 | 0 |
| MTUS1 | 0 | 0 |
| INTS10 | 0 | 0 |
| LOC286114 | 0 | 0 |
| DCTN6 | 0 | 0 |
| TRAM1 | 0 | 0 |
| PEX2 | 0 | 0 |
| FAM82B | 0 | 0 |
| RNF19A | 0 | 0 |
| ZFPM2 | 0 | 0 |
| EIF3E | 0 | 0 |
| FER1L6 | 0 | 0 |
| LOC100130231 | 0 | 0 |
| PVT1 | 0 | 0 |
| LOC728724 | 0 | 0 |
| APBA1 | 0 | 0 |
| PCSK5 | 0 | 0 |
| TLE4 | 0 | 0 |
| SPIN1 | 0 | 0 |
| GRIN3A | 0 | 0 |
| PALM2 | 0 | 0 |
| ZNF483 | 0 | 0 |
| FUBP3 | 0 | 0 |
| TTF1 | 0 | 0 |
| LOC100216001 | 0 | 0 |
| CAMK1D | 0 | 0 |
| CUBN | 0 | 0 |
| CHAT | 0 | 0 |
| PCDH15 | 0 | 0 |
| USP54 | 0 | 0 |
| PPIF | 0 | 0 |

TABLE 4-continued

| Gene symbol | Highorder | Cluster |
|---|---|---|
| FLJ37201 | 0 | 0 |
| CNNM1 | 0 | 0 |
| C10orf26 | 0 | 0 |
| OR52B4 | 0 | 0 |
| SPON1 | 0 | 0 |
| CALCA | 0 | 0 |
| SOX6 | 0 | 0 |
| ANO3 | 0 | 0 |
| ZFP91-CNTF | 0 | 0 |
| SCYL1 | 0 | 0 |
| SPTBN2 | 0 | 0 |
| GAB2 | 0 | 0 |
| ODZ4 | 0 | 0 |
| JRKL | 0 | 0 |
| HTR3A | 0 | 0 |
| SIK3 | 0 | 0 |
| ARHGEF12 | 0 | 0 |
| MIR4493 | 0 | 0 |
| CLEC4D | 0 | 0 |
| ETV6 | 0 | 0 |
| AEBP2 | 0 | 0 |
| CCDC91 | 0 | 0 |
| ANO6 | 0 | 0 |
| FAM113B | 0 | 0 |
| OR10AD1 | 0 | 0 |
| FAIM2 | 0 | 0 |
| CSRNP2 | 0 | 0 |
| KRT8 | 0 | 0 |
| RASSF3 | 0 | 0 |
| LEMD3 | 0 | 0 |
| LOC283392 | 0 | 0 |
| CLLU1OS | 0 | 0 |
| C12orf74 | 0 | 0 |
| MED13L | 0 | 0 |
| COQ5 | 0 | 0 |
| OASL | 0 | 0 |
| P2RX7 | 0 | 0 |
| LINC00548 | 0 | 0 |
| FOXO1 | 0 | 0 |
| DGKH | 0 | 0 |
| TPT1-AS1 | 0 | 0 |
| SLITRK1 | 0 | 0 |
| UBAC2 | 0 | 0 |
| MYO16 | 0 | 0 |
| ATP4B | 0 | 0 |
| CHAMP1 | 0 | 0 |
| PRMT5 | 0 | 0 |
| MIPOL1 | 0 | 0 |
| ARG2 | 0 | 0 |
| ZFP36L1 | 0 | 0 |
| VASH1 | 0 | 0 |
| C14orf166B | 0 | 0 |
| NOXRED1 | 0 | 0 |
| VRK1 | 0 | 0 |
| C14orf177 | 0 | 0 |
| BCL11B | 0 | 0 |
| LOC283710 | 0 | 0 |
| OTUD7A | 0 | 0 |
| FMN1 | 0 | 0 |
| RASGRP1 | 0 | 0 |
| MIR626 | 0 | 0 |
| SEMA6D | 0 | 0 |
| RORA | 0 | 0 |
| USP3 | 0 | 0 |
| HERC1 | 0 | 0 |
| DENND4A | 0 | 0 |
| PARP6 | 0 | 0 |
| ETFA | 0 | 0 |
| IREB2 | 0 | 0 |
| MEX3B | 0 | 0 |
| CRTC3 | 0 | 0 |
| MEF2A | 0 | 0 |
| C16orf5 | 0 | 0 |
| CLEC16A | 0 | 0 |
| SCNN1G | 0 | 0 |
| SRCAP | 0 | 0 |
| SLC6A2 | 0 | 0 |
| CYB5B | 0 | 0 |
| NFAT5 | 0 | 0 |
| GLG1 | 0 | 0 |
| UBE2G1 | 0 | 0 |
| AIPL1 | 0 | 0 |
| FXR2 | 0 | 0 |
| MAP2K4 | 0 | 0 |
| NSRP1 | 0 | 0 |
| TNS4 | 0 | 0 |
| STAT5B | 0 | 0 |
| KIAA1267 | 0 | 0 |
| RAD51C | 0 | 0 |
| CD300LD | 0 | 0 |
| LOC100507351 | 0 | 0 |
| RPTOR | 0 | 0 |
| CSNK1D | 0 | 0 |
| SMCHD1 | 0 | 0 |
| MIB1 | 0 | 0 |
| SETBP1 | 0 | 0 |
| ST8SIA3 | 0 | 0 |
| CDH20 | 0 | 0 |
| TSHZ1 | 0 | 0 |
| SCAMP4 | 0 | 0 |
| UHRF1 | 0 | 0 |
| RDH8 | 0 | 0 |
| DNMT1 | 0 | 0 |
| ZNF627 | 0 | 0 |
| RTBDN | 0 | 0 |
| BABAM1 | 0 | 0 |
| CEACAM5 | 0 | 0 |
| EXOC3L2 | 0 | 0 |
| ZNF765 | 0 | 0 |
| ZSCAN5A | 0 | 0 |
| ZNF211 | 0 | 0 |
| ZNF132 | 0 | 0 |
| JAG1 | 0 | 0 |
| ASXL1 | 0 | 0 |
| DNMT3B | 0 | 0 |
| PREX1 | 0 | 0 |
| LINC00320 | 0 | 0 |
| C21orf54 | 0 | 0 |
| IFNAR2 | 0 | 0 |
| LINC00310 | 0 | 0 |
| PDE9A | 0 | 0 |
| TRAPPC10 | 0 | 0 |
| PTTG1IP | 0 | 0 |
| CYTH4 | 0 | 0 |
| ADSL | 0 | 0 |
| DGKK | 0 | 0 |
| PHF8 | 0 | 0 |
| FRMD8P1 | 0 | 0 |
| LOC643486 | 0 | 0 |
| FMR1NB | 0 | 0 |
| AVPR2 | 0 | 0 |

REFERENCES

1. Soiffer R, Hodi F S, Haluska F, Jung K, Gillessen S, Singer S, et al. Vaccination with irradiated, autologous melanoma cells engineered to secrete granulocyte-macrophage colony-stimulating factor by adenoviral-mediated gene transfer augments antitumor immunity in patients with metastatic melanoma. *J Clin Oncol* 2003 Sep. 1; 21(17): 3343-3350.
2. Andolfi G, Fousteri G, Rossetti M, Magnani C F, Jofra T, Locafaro G, et al. Enforced IL-10 expression confers type 1 regulatory T cell (Tr1) phenotype and function to human CD4(+) T cells. *Mol Ther* 2013 September; 20(9): 1778-1790.
3. Magnani C F, Tettamanti S, Maltese F, Turazzi N, Biondi A, Biagi E. Advanced targeted, cell and gene-therapy approaches for pediatric hematological malignancies: results and future perspectives. *Front Oncol* 2013; 3: 106.

4. Di Stasi A, Tey S K, Dotti G, Fujita Y, Kennedy-Nasser A, Martinez C, et al. Inducible apoptosis as a safety switch for adoptive cell therapy. *N Engl J Med* 2011 Nov. 3; 365(18): 1673-1683.
5. Gagliani N, Magnani C F, Huber S, Gianolini M E, Pala M, Licona-Limon P, et al. Coexpression of CD49b and LAG-3 identifies human and mouse T regulatory type 1 cells. *Nat Med* 2013 Jim; 19(6): 739-746.
6. Passerini L, Mel E R, Sartirana C, Fousteri G, Bondanza A, Naldini L, et al. CD4(+) T cells from IPEX patients convert into functional and stable regulatory T cells by FOXP3 gene transfer. *Sci Transl Med* 2013 Dec. 11; 5(215): 215ra174.
7. Morgan R A, Dudley M E, Wunderlich J R, Hughes M S, Yang J C, Sherry R M, et al. Cancer regression in patients after transfer of genetically engineered lymphocytes. *Science* 2006 Oct. 6; 314(5796): 126-129.
8. Robbins P F, Morgan R A, Feldman S A, Yang J C, Sherry R M, Dudley M E, et al. Tumor regression in patients with metastatic synovial cell sarcoma and melanoma using genetically engineered lymphocytes reactive with NY-ESO-1. *J Clin Oncol* 2011 Mar. 1; 29(7): 917-924.
9. Brentjens R J, Riviere I, Park J H, Davila M L, Wang X, Stefanski J, et al. Safety and persistence of adoptively transferred autologous CD19-targeted T cells in patients with relapsed or chemotherapy refractory B-cell leukemias. *Blood* 2011 Nov. 3; 118(18): 4817-4828.
10. Grupp S A, Kalos M, Barrett D, Aplenc R, Porter D L, Rheingold S R, et al. Chimeric antigen receptor-modified T cells for acute lymphoid leukemia. *N Engl J Med* 2013 Apr. 18; 368(16): 1509-1518.
11. Lee D W, Kochenderfer J N, Stetler-Stevenson M, Cui Y K, Delbrook C, Feldman S A, et al. T cells expressing CD19 chimeric antigen receptors for acute lymphoblastic leukaemia in children and young adults: a phase 1 dose-escalation trial. *Lancet* 2014 Oct. 10.
12. Maude S L, Frey N, Shaw P A, Aplenc R, Barrett D M, Bunin N J, et al. Chimeric antigen receptor T cells for sustained remissions in leukemia. *N Engl J Med* 2014 Oct. 16; 371(16): 1507-1517.
13. Oliveira G, Greco R, Lupo-Stanghellini M T, Vago L, Bonini C. Use of TK-cells in haploidentical hematopoietic stem cell transplantation. *Curr Opin Hematol* 2012 November; 19(6): 427-433.
14. Marin V, Cribioli E, Philip B, Tettamanti S, Pizzitola I, Biondi A, et al. Comparison of different suicide-gene strategies for the safety improvement of genetically manipulated T cells. *Hum Gene Ther Methods* 2012 December; 23(6): 376-386.
15. Kay M A, Glorioso J C, Naldini L. Viral vectors for gene therapy: the art of turning infectious agents into vehicles of therapeutics. *Nat Med* 2001 January; 7(1): 33-40.
16. Naldini L. Ex vivo gene transfer and correction for cell-based therapies. *Nat Rev Genet* 2011 May; 12(5): 301-315.
17. Silva G, Poirot L, Galetto R, Smith J, Montoya G, Duchateau P, et al. Meganucleases and other tools for targeted genome engineering: perspectives and challenges for gene therapy. *Curr Gene Ther* 2011 February; 11(1): 11-27.
18. Wilber A, Ulloa Montoya F, Hammer L, Moriarity B S, Geurts A M, Largaespada D A, et al. Efficient non-viral integration and stable gene expression in multipotent adult progenitor cells. *Stem Cells Int* 2009; 2011: 717069.
19. Hackett P B, Largaespada D A, Cooper L J. A transposon and transposase system for human application. *Mol Ther* 2010 April; 18(4): 674-683.
20. Neumann E, Schaefer-Ridder M, Wang Y, Hofschneider P H. Gene transfer into mouse lyoma cells by electroporation in high electric fields. *Embo J* 1982; 1(7): 841-845.
21. Yant S R, Wu X, Huang Y, Garrison B, Burgess S M, Kay M A. High-resolution genome-wide mapping of transposon integration in mammals. *Mol Cell Biol* 2005 March; 25(6): 2085-2094.
22. Nakazawa Y, Huye L E, Salsman V S, Leen A M, Ahmed N, Rollins L, et al. PiggyBac-mediated cancer immunotherapy using EBV-specific cytotoxic T cells expressing HER2-specific chimeric antigen receptor. *Mol Ther* 2011 December; 19(12): 2133-2143.
23. Wilson M H, Coates C J, George A L, Jr. PiggyBac transposon-mediated gene transfer in human cells. *Mol Ther* 2007 January; 15(1): 139-145.
24. Wu S C, Meir Y J, Coates C J, Handler A M, Pelczar P, Moisyadi S, et al. piggyBac is a flexible and highly active transposon as compared to sleeping beauty, Tol2, and Mos1 in mammalian cells. *Proc Natl Acad Sci USA* 2006 Oct. 10; 103(41): 15008-15013.
25. Magnani C F, Turazzi N, Benedicenti F, Paola Giordano Attianese G M, Tettamanti S, Montini E, et al. Stable Expression Of Chimeric Antigen Receptors (CARs) By Sleeping Beauty-Mediated Gene Transfer and Efficient Expansion Of Leukemia-Specific Cytokine-Induced Killer (CIK) Cells. *Blood* 2013 2013-11-15 00:00:00; 122(21): 1663-1663.
26. Singh H, Figliola M J, Dawson M J, Olivares S, Zhang L, Yang G, et al. Manufacture of clinical-grade CD19-specific T cells stably expressing chimeric antigen receptor using Sleeping Beauty system and artificial antigen presenting cells. *PLoS One* 2013; 8(5): e64138.
27. Singh H, Manuri P R, Olivares S, Dara N, Dawson M J, Huls H, et al. Redirecting specificity of T cell populations for CD19 using the Sleeping Beauty system. *Cancer Res* 2008 Apr. 15; 68(8): 2961-2971.
28. Lu P H, Negrin R S. A novel population of expanded human CD3+CD56+ cells derived from T cells with potent in vivo antitumor activity in mice with severe combined immunodeficiency. *J Immunol* 1994 Aug. 15; 153(4): 1687-1696.
29. Pievani A, Borleri G, Pende D, Moretta L, Rambaldi A, Golay J, et al. Dual-functional capability of CD3+CD56+ CIK cells, a T cell subset that acquires NK function and retains TCR-mediated specific cytotoxicity. *Blood* 2011 Sep. 22; 118(12): 3301-3310.
30. Schmidt-Wolf I G, Negrin R S, Kiem H P, Blume K G, Weissman I L. Use of a SCID mouse/human lymphoma model to evaluate cytokine-induced killer cells with potent antitumor cell activity. *J Exp Med* 1991 Jul. 1; 174(1): 139-149.
31. Field A C, Vink C, Gabriel R, Al-Subki R, Schmidt M, Goulden N, et al. Comparison of lentiviral and sleeping beauty mediated alphabeta T cell receptor gene transfer. *PLoS One* 2013; 8(6): e68201.
32. Kebriaei P, Huls H, Jena B, Munsell M, Jackson R, Lee D A, et al. Infusing CD19-directed T cells to augment disease control in patients undergoing autologous hematopoietic stem-cell transplantation for advanced B-lymphoid malignancies. *Hum Gene Ther* 2012 May; 23(5): 444-450.

33. Peng P D, Cohen C J, Yang S, Hsu C, Jones S, Zhao Y, et al. Efficient nonviral Sleeping Beauty transposon-based TCR gene transfer to peripheral blood lymphocytes confers antigen-specific antitumor reactivity. *Gene Ther* 2009 August; 16(8): 1042-1049.

34. Boch J, Scholze H, Schornack S, Landgraf A, Hahn S, Kay S, et al. Breaking the code of DNA binding specificity of TAL-type III effectors. *Science* 2009 Dec. 11; 326(5959): 1509-1512.

35. Christian M, Cermak T, Doyle E L, Schmidt C, Zhang F, Hummel A, et al. Targeting DNA double-strand breaks with TAL effector nucleases. *Genetics* 2010 October; 186(2): 757-761.

36. Cong L, Ran F A, Cox D, Lin S, Barretto R, Habib N, et al. Multiplex genome engineering using CRISPR/Cas systems. *Science* 2013 Feb. 15; 339(6121): 819-823.

37. Mali P, Yang L, Esvelt K M, Aach J, Guell M, DiCarlo J E, et al. RNA-guided human genome engineering via Cas9. *Science* 2013 Feb. 15; 339(6121): 823-826.

38. Ivics Z, Hackett P B, Plasterk R H, Izsvak Z. Molecular reconstruction of Sleeping Beauty, a Tc1-like transposon from fish, and its transposition in human cells. *Cell* 1997 Nov. 14; 91(4): 501-510.

39. Ding S, Wu X, Li G, Han M, Zhuang Y, Xu T. Efficient transposition of the piggyBac (PB) transposon in mammalian cells and mice. *Cell* 2005 Aug. 12; 122(3): 473-483.

40. Fraser M J, Ciszczon T, Elick T, Bauser C. Precise excision of TTAA-specific lepidopteran transposons piggyBac (IFP2) and tagalong (TFP3) from the baculovirus genome in cell lines from two species of Lepidoptera. *Insect Mol Biol* 1996 May; 5(2): 141-151.

41. Geurts A M, Yang Y, Clark K J, Liu G, Cui Z, Dupuy A J, et al. Gene transfer into genomes of human cells by the sleeping beauty transposon system. *Mol Ther* 2003 July; 8(1): 108-117.

42. Magnani C F, Alberigo G, Bacchetta R, Serafini G, Andreani M, Roncarolo M G, et al. Killing of myeloid APCs via HLA class I, CD2 and CD226 defines a novel mechanism of suppression by human Tr1 cells. *Eur J Immunol* 2011 June; 41(6): 1652-1662.

43. Wilber A, Frandsen J L, Geurts J L, Largaespada D A, Hackett P B, McIvor R S. RNA as a source of transposase for Sleeping Beauty-mediated gene insertion and expression in somatic cells and tissues. *Mol Ther* 2006 March; 13(3): 625-630.

44. Dotti G, Heslop H E. Current status of genetic modification of T cells for cancer treatment. *Cytotherapy* 2005; 7(3): 262-272.

45. Nicholson I C, Lenton K A, Little D J, Decorso T, Lee F T, Scott A M, et al. Construction and characterisation of a functional CD19 specific single chain Fv fragment for immunotherapy of B lineage leukaemia and lymphoma. *Mol Immunol* 1997 November-December; 34(16-17): 1157-1165.

46. Pizzitola I, Anjos-Afonso F, Rouault-Pierre K, Lassailly F, Tettamanti S, Spinelli O, et al. Chimeric antigen receptors against CD33/CD123 antigens efficiently target primary acute myeloid leukemia cells in vivo. *Leukemia* 2014 Feb. 7.

47. Tettamanti S, Marin V, Pizzitola I, Magnani C F, Giordano Attianese G M, Cribioli E, et al. Targeting of acute myeloid leukaemia by cytokine-induced killer cells redirected with a novel CD123-specific chimeric antigen receptor. *Br J Haematol* 2013 May; 161(3): 389-401.

48. Aiuti A, Biasco L, Scaramuzza S, Ferrua F, Cicalese M P, Baricordi C, et al. Lentiviral hematopoietic stem cell gene therapy in patients with Wiskott-Aldrich syndrome. *Science* 2013 Aug. 23; 341(6148): 1233151.

49. Biffi A, Montini E, Lorioli L, Cesani M, Fumagalli F, Plati T, et al. Lentiviral hematopoietic stem cell gene therapy benefits metachromatic leukodystrophy. *Science* 2013 Aug. 23; 341(6148): 1233158.

50. de Jong J, Akhtar W, Badhai J, Rust A G, Rad R, Hilkens J, et al. Chromatin landscapes of retroviral and transposon integration profiles. *PLoS Genet* 2014 April; 10(4): e1004250.

51. Vigdal T J, Kaufman C D, Izsvak Z, Voytas D F, Ivics Z. Common physical properties of DNA affecting target site selection of sleeping beauty and other Tc1/mariner transposable elements. *J Mol Biol* 2002 Oct. 25; 323(3): 441-452.

52. Sun Q, Woodcock J M, Rapoport A, Stomski F C, Korpelainen E I, Bagley C J, et al. Monoclonal antibody 7G3 recognizes the N-terminal domain of the human interleukin-3 (IL-3) receptor alpha-chain and functions as a specific IL-3 receptor antagonist. *Blood* 1996 Jan. 1; 87(1): 83-92.

53. Marin V, Dander E, Biagi E, Introna M, Fazio G, Biondi A, et al. Characterization of in vitro migratory properties of anti-CD19 chimeric receptor-redirected CIK cells for their potential use in B-ALL immunotherapy. *Exp Hematol* 2006 September; 34(9): 1219-1229.

54. Alter G, Malenfant J M, Altfeld M. CD107a as a functional marker for the identification of natural killer cell activity. *Journal of immunological methods* 2004 November; 294(1-2): 15-22.

55. Heeg K, Reimann J, Kabelitz D, Hardt C, Wagner H. A rapid colorimetric assay for the determination of IL-2-producing helper T cell frequencies. *Journal of immunological methods* 1985 Mar. 18; 77(2): 237-246.

56. van de Loosdrecht A A, Beelen R H, Ossenkoppele G J, Broekhoven M G, Langenhuijsen M M. A tetrazolium-based colorimetric MTT assay to quantitate human monocyte mediated cytotoxicity against leukemic cells from cell lines and patients with acute myeloid leukemia. *Journal of immunological methods* 1994 Sep. 14; 174(1-2): 311-320.

57. Schmidt M, Schwarzwaelder K, Bartholomae C, Zaoui K, Ball C, Pilz I, et al. High-resolution insertion-site analysis by linear amplification-mediated PCR (LAM-PCR). *Nat Methods* 2007 December; 4(12): 1051-1057.

58. van Dongen J J, Langerak A W, Bruggemann M, Evans P A, Hummel M, Lavender F L, et al. Design and standardization of PCR primers and protocols for detection of clonal immunoglobulin and T cell receptor gene recombinations in suspect lymphoproliferations: report of the BIOMED-2 Concerted Action BMH4-CT98-3936. *Leukemia* 2003 December; 17(12): 2257-2317.

59. Bene M C, Castoldi G, Knapp W, Ludwig W D, Matutes E, Orfao A, et al. Proposals for the immunological classification of acute leukemias. European Group for the Immunological Characterization of Leukemias (EGIL). *Leukemia* 1995 October; 9(10): 1783-1786.

60. Huang X, Guo H, Kang J, Choi S, Zhou T C, Tammana S, et al. Sleeping Beauty transposon-mediated engineering of human primary T cells for therapy of CD19+ lymphoid malignancies. *Mol Ther* 2008 March; 16(3): 580-9.

The invention claimed is:

1. A method of generating genetically modified cytokine induced killer cells expressing one or more T cell receptors (CIK-TCR) or chimeric antigen receptors (CIK-CAR), the method comprising the sequential steps of:
   (a) non-viral transfer of one or more nucleic acids or exogenous nucleic acids encoding T cell receptors or chimeric antigen receptors into a population of mononuclear cells in a cell culture;
   (b) addition of IFN-γ and irradiated peripheral blood mononuclear cells to the cell culture within about 0 and 1 day after the transfer of nucleic acids; and
   (c) addition of a stimulating agent and a cytokine to the cell culture after the transfer of nucleic acids; wherein the stimulating agent is an anti-CD3 antibody; wherein the cytokine is selected from the group consisting of IL-2, IL-7, IL-15, IL-21 and a combination thereof; and wherein the population of mononuclear cells in the cell culture comprises: peripheral blood mononuclear cells, bone marrow derived mononuclear cells, umbilical cord blood derived mononuclear cells, natural killer cells, hematopoietic stem cells, pluripotent embryonic stem cells or induced pluripotent stem cells or combinations thereof.

2. The method of claim 1, wherein the non-viral transfer of nucleic acids further comprises the use of: transposons, Zn-finger nucleases, integrases, clustered regularly interspaced short palindromic repeats, sequence-specific recombinase systems able to integrate nucleic acids by recombination between attachment sites, Sleeping Beauty, PiggyBac, TALEs, phiC31 or CRISPR/Cas or combinations thereof.

3. The method of claim 1, wherein said anti-CD3 antibody is OKT3.

4. The method of claim 1, wherein IFN-γ is added within about 2 hours or between 0 and about 2 hours after the transfer of nucleic acids.

5. The method of claim 1, wherein the non-viral transfer of nucleic acids is carried out by electroporation or nucleofection.

6. The method of claim 1, wherein one or more nucleic acids or exogenous nucleic acids are transferred in an amount from about 0.1 to about 100 μg.

7. The method of claim 1, wherein IFN-γ is added in an amount of from about 10 U/ml to about 10,000 U/ml or in an amount of about 1,000 U/ml.

8. The method of claim 1, wherein the stimulating agent is added in an amount of from about 5 ng/ml to about 100 μg/ml or in an amount of about 50 ng/ml.

9. The method of claim 1, wherein the stimulating agent is added to the cell culture once after the transfer of nucleic acids.

10. The method of claim 1, further comprising step (d) addition of one or more expanding agents to the cell culture after step (c).

11. The method of claim 10, wherein the one or more expanding agents are added to the cell culture at least once after step (c).

12. The method of claim 10, further comprising step (e) isolating the cells from the cell culture to obtain a cell population comprising the CIK modified cells.

13. The method of claim 2, wherein the nucleic acids encode for T cell receptors or chimeric antigen receptors that target CD19, CD123, CD20, CD23, CRLF2, CD44v6, CD33, CS1, CD38, Her2, EGFR and/or CA125.

14. The method of claim 1, wherein irradiated peripheral blood mononuclear cells are added to the cell culture within about 3 hours or between 0 to about 3 hours, or within about 2 hours or between 0 to about 2 hours after the transfer of nucleic acids.

15. The method of claim 3, wherein OKT3 is added to the cell culture within about 10 days or between 0 and about 10 days, within about 5 days or between 0 and about 5 days, or within about 1 day or between 0 and about 1 day after the transfer of nucleic acids.

16. The method of claim 1, wherein the cytokine is added to the cell culture within about 10 days or between 0 and 10 days or within about 1 day or between 0 and about 1 day after the transfer of the nucleic acids.

17. The method of claim 1, wherein irradiated peripheral blood mononuclear cells are added to the cell culture only once.

18. The method of claim 10, wherein the expanding agent is IL-2.

* * * * *